US012757624B2

(12) United States Patent
Min et al.

(10) Patent No.: US 12,757,624 B2
(45) Date of Patent: Oct. 6, 2026

(54) ORGANIC LIGHT EMITTING DIODE AND ORGANIC LIGHT EMITTING DEVICE INCLUDING THE SAME

(71) Applicant: LG Display Co., Ltd., Seoul (KR)

(72) Inventors: Hye-Li Min, Paju-si (KR); In-Ae Shin, Paju-si (KR); Gi-Hwan Lim, Paju-si (KR); Jun-Yun Kim, Paju-si (KR)

(73) Assignee: LG DISPLAY CO., LTD., Seoul (KR)

( * ) Notice: Subject to any disclaimer, the term of this patent is extended or adjusted under 35 U.S.C. 154(b) by 1035 days.

(21) Appl. No.: 17/962,247

(22) Filed: Oct. 7, 2022

(65) Prior Publication Data

US 2023/0157150 A1 May 18, 2023

(30) Foreign Application Priority Data

Nov. 18, 2021 (KR) ........................ 10-2021-0159515

(51) Int. Cl.
*H10K 85/30* (2023.01)
*C07D 209/86* (2006.01)
(Continued)

(52) U.S. Cl.
CPC ......... *H10K 85/322* (2023.02); *C07D 209/86* (2013.01); *C07F 5/027* (2013.01);
(Continued)

(58) Field of Classification Search
CPC ............. H10K 85/322; H10K 85/6572; H10K 50/131; H10K 2101/30; H10K 85/615;
(Continued)

(56) References Cited

U.S. PATENT DOCUMENTS 8,183,560 B2 * 5/2012 Ikeda .................. H10K 85/622 257/E51.026
2019/0062348 A1 2/2019 Sung et al.
2021/0143339 A1 5/2021 Yoon et al.

FOREIGN PATENT DOCUMENTS

KR 10-2081481 B1 2/2020
KR 10-2021-0046539 A 4/2021
KR 10-2021-0055898 A 5/2021

OTHER PUBLICATIONS

Machine translation of description of KR 1020210043539 A. (Year: 2021).*

(Continued)

*Primary Examiner* — Dawn L Garrett
(74) *Attorney, Agent, or Firm* — Birch, Stewart, Kolasch & Birch, LLP

(57) ABSTRACT

An organic light emitting diode (OLED) including at least one emitting material layer (EML) disposed between two electrodes and including plural delayed fluorescent materials having at least one carbazolyl moiety and BODIPY-based fluorescent material and an organic light emitting device including the OLED are discussed. The delayed fluorescent material and the fluorescent material can be included in the same emitting material layer or adjacently disposed emitting material layers. The OLED can lower its driving voltage and improve its luminous efficiency utilizing the advantages of the delayed fluorescent materials and the fluorescent material by adjusting energy levels among the delayed fluorescent materials and the fluorescent material.

21 Claims, 17 Drawing Sheets

D1

(51) Int. Cl.

| | |
|---|---|
| ***C07F 5/02*** | (2006.01) |
| ***C09K 11/06*** | (2006.01) |
| ***H10K 50/13*** | (2023.01) |
| ***H10K 85/60*** | (2023.01) |
| ***H10K 101/30*** | (2023.01) |

(52) U.S. Cl.
CPC .......... *C09K 11/06* (2013.01); *H10K 85/6572* (2023.02); *C09K 2211/1018* (2013.01); *H10K 50/131* (2023.02); *H10K 2101/30* (2023.02)

(58) Field of Classification Search
CPC .... H10K 85/636; H10K 85/654; H10K 50/11; H10K 2101/20; H10K 2101/40; H10K 85/6574; C07D 209/86; C07F 5/027; C07F 5/022; C09K 11/06; C09K 2211/1018
See application file for complete search history.

(56) References Cited

OTHER PUBLICATIONS

Wex, B., & Kaafarani, B. R. (2017). Perspective on carbazole-based organic compounds as emitters and hosts in TADF applications. Journal of Materials Chemistry C, 5(34), 8622-8653. (Year: 2017).*

* cited by examiner

ORGANIC LIGHT EMITTING DIODE AND ORGANIC LIGHT EMITTING DEVICE INCLUDING THE SAME

CROSS-REFERENCE TO RELATED APPLICATIONS

This application claims the benefit under 35 U.S.C. § 119(a) to Korean Patent Application No. 10-2021-0159515, filed in the Republic of Korea on Nov. 18, 2021, the entire contents of which are incorporated herein by reference into the present application.

BACKGROUND

Technical Field

The present disclosure relates to an organic light emitting diode, and more specifically, to an organic light emitting diode having excellent luminous properties and an organic light emitting device having the diode.

Discussion of the Related Art

As display devices have become larger, there exists a need for a flat display device with lower spacing occupation. Among the flat display devices, a display device using an organic light emitting diode (OLED) has come into the spotlight as a luminous display device replacing rapidly a liquid crystal display device (LCD).

The OLED can be formed as a thin film having a thickness less than 2000 Å and can be implement unidirectional or bidirectional images as electrode configurations. Also, the OLED can be formed on a flexible transparent substrate such as a plastic substrate so that OLED can implement a flexible or foldable display with ease. In addition, the OLED has advantages over LCD (liquid crystal display device), for example, the OLED can be driven at a lower voltage and has very high color purity.

In the OLED, when electrical charges are injected into an emitting material layer between an electron injection electrode (i.e., cathode) and a hole injection electrode (i.e., anode), electrical charges are recombined to form excitons, and then emit light as the recombined excitons are shifted to a stable ground state.

Fluorescent materials of the related art have shown low luminous efficiency because only the singlet excitons are involved in the luminescence process thereof. The phosphorescent materials in which triplet excitons as well as the singlet excitons are involved in the luminescence process have relatively high luminous efficiency compared to the fluorescent material. However, the metal complex as the representative phosphorescent material has too short luminous lifespan to be applicable into commercial devices.

SUMMARY OF THE DISCLOSURE

Accordingly, embodiments of the present disclosure are directed to an OLED and an organic light emitting device including the OLED that substantially obviates one or more of the problems due to the limitations and disadvantages of the related art.

An aspect of the present disclosure is to provide an OLED that can improve luminous efficiency, color purity and luminous lifespan and an organic light emitting device including the diode.

Additional features and aspects will be set forth in the description that follows, and in part will be apparent from the description, or can be learned by practice of the inventive concepts provided herein. Other features and aspects of the inventive concepts can be realized and attained by the structure particularly pointed out in the written description, or derivable therefrom, and the claims hereof as well as the appended drawings.

To achieve these and other aspects of the inventive concepts, as embodied and broadly described, an organic light emitting diode includes a first electrode; a second electrode facing the first electrode; and an emissive layer disposed between the first and second electrodes and including at least one emitting material layer, wherein the at least one emitting material layer includes a first compound, a second compound and a third compound, and wherein the first compound has the following structure of Formula 1 or a structure formed by linking two structures of Formula 1 via a direct or indirect bond, the second compound has the following structure of Formula 3 and the third compound has the following structure of Formula 5:

[Formula 1]

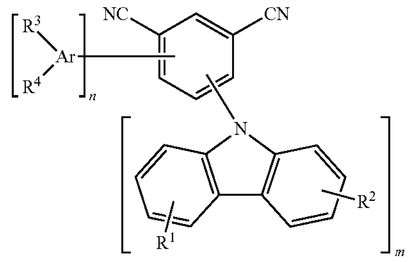

wherein, in Formula 1, each of $R^1$ and $R^2$ is independently hydrogen, deuterium, tritium, unsubstituted or substituted $C_1$-$C_{20}$ alkyl, an unsubstituted or substituted $C_6$-$C_{30}$ aromatic group or an unsubstituted or substituted $C_3$-$C_{30}$ hetero aromatic group;

each of $R^3$ and $R^4$ is independently an unsubstituted or substituted carbazolyl group;

Ar is an unsubstituted or substituted $C_6$-$C_{30}$ aromatic ring or an unsubstituted or substituted $C_3$-$C_{30}$ hetero aromatic group;

m is an integer of 1 to 4; and n is an integer of 0 to 1, wherein m plus n is an integer of 1 to 4,

[Formula 3]

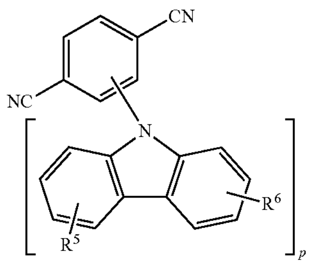

wherein, in Formula 3, each of $R^5$ and $R^6$ is independently hydrogen, deuterium, tritium, unsubstituted or substituted $C_1$-$C_{20}$ alkyl, an unsubstituted or substituted $C_6$-$C_{30}$ aromatic group or an unsubstituted or substituted $C_3$-$C_{30}$ hetero aromatic group, wherein at least one of $R^5$ and $R^6$ is an unsubstituted or substituted $C_1$-$C_{20}$ alkyl, an unsubstituted or substituted $C_6$-$C_{30}$ aromatic group or an unsubstituted or substituted $C_3$-$C_{30}$ hetero aromatic group; and p is an integer of 1 to 4,

[Formula 5]

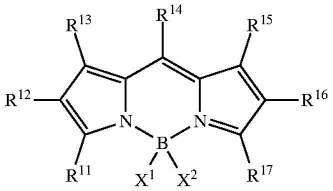

wherein, in Formula 5, each of $R^{11}$ to $R^{17}$ is independently hydrogen, deuterium, tritium, an unsubstituted or substituted $C_1$-$C_{20}$ alkyl, an unsubstituted or substituted $C_6$-$C_{30}$ aromatic group or an unsubstituted or substituted $C_3$-$C_{30}$ hetero aromatic group; and each of $X^1$ and $X^2$ is independently a halogen atom.

As an example, a Highest Occupied Molecular Orbital (HOMO) energy level of the first compound can be identical to or lower than a HOMO energy level of the second compound, and the HOMO energy level of the second compound can be identical to or lower than a HOMO energy level of the third compound.

For example, a HOMO energy level of the first compound and a HOMO energy level of the second compound can satisfy the following relationship in Equation (1), and the HOMO energy level of the second compound and a HOMO energy level of the third compound can satisfy the following relationship in Equation (2):

$$-0.3\text{ eV} \le HOMO^{DF1} - HOMO^{DF2} \le 0\text{ eV}; \quad (1)$$

$$-0.4\text{ eV} \le HOMO^{DF2} - HOMO^{FD} \le 0\text{ eV}, \quad (2)$$

wherein $HOMO^{DF1}$ indicates a HOMO energy level of the first compound, $HOMO^{DF2}$ indicates a HOMO energy level of the second compound and $HOMO^{FD}$ indicates a HOMO energy level of the third compound.

In another exemplar aspect, a Lowest Unoccupied Molecular Orbital (LUMO) energy level of the first compound can be identical to or higher than a LUMO energy level of the second compound, and the LUMO energy level of the second compound can be identical to or higher than a LUMO energy level of the third compound.

For example, a LUMO energy level of the first compound and a LUMO energy level of the second compound can satisfy the following relationship in Equation (3), and the LUMO energy level of the second compound and a LUMO energy level of the third compound can satisfy the following relationship in Equation (4):

$$0\text{ eV} \le LUMO^{DF1} - LUMO^{DF2} \le 0.3\text{ eV}; \quad (3)$$

$$0\text{ eV} \le LUMO^{DF2} - LUMO^{FD} \le 0.3\text{ eV}, \quad (4)$$

wherein $LUMO^{DF1}$ indicates a LUMO energy level of the first compound, $LUMO^{DF2}$ indicates a LUMO energy level of the second compound and $LUMO^{FD}$ indicates a LUMO energy level of the third compound.

In one exemplary aspect, the at least one emitting material layer can have a single-layered emitting material layer. The single-layered emitting material layer can further include a fourth compound.

Each of an excited singlet energy level and an excited triplet energy level of the fourth compound can be higher than each of an excited singlet energy level and an excited triplet energy level of the first compound, respectively.

Alternatively, the at least one emitting material layer includes a first emitting material layer disposed between the first and second electrodes and a second emitting material layer disposed between the first electrode and the first emitting material layer or between the first emitting material layer and the second electrode, and wherein the first emitting material layer includes the first compound and the second compound and the second emitting material layer includes the third compound.

The first emitting material layer can further include a fourth compound and the second emitting material layer can further include a fifth compound.

As an example, each of an excited singlet energy level and an excited triplet energy level of the fourth compound can be higher than each of an excited singlet energy level and an excited triplet energy level of the first compound, respectively, and an excited singlet energy level of the fifth compound can be higher than an excited singlet energy level of the third compound.

Optionally, when the at least one emitting material layer includes the first and second emitting material layers, the at least one emitting material layer can further include a third emitting material layer disposed oppositely to the second emitting material layer with respect to the first emitting material layer.

In one exemplary aspect, the emissive layer can include a single emitting unit. Alternatively, the emissive layer can include multiple emitting parts to form a tandem structure.

In another aspect, an organic light emitting device, such as an organic light emitting display device or an organic light emitting luminescent device comprises a substrate and the OLED disposed over the substrate, as described above.

It is to be understood that both the foregoing general description and the following detailed description are exemplary and explanatory and are intended to provide further explanation of the inventive concepts as claimed.

BRIEF DESCRIPTION OF THE DRAWING

The accompanying drawings, which are included to provide a further understanding of the disclosure, are incorporated in and constitute a part of this application, illustrate embodiments of the disclosure and together with the description serve to explain principles of the disclosure.

DETAILED DESCRIPTION OF THE EMBODIMENTS

Reference and discussions will now be made below in detail to aspects, embodiments and examples of the disclosure, some examples of which are illustrated in the accompanying drawings.

The present disclosure relates to an organic light emitting diode (OLED) into which first to third compounds having adjusted energy levels are applied in an identical EML or adjacently disposed EMLs and an organic light emitting device having the OLED. The OLED can be applied into an organic light emitting device such as an organic light emitting display device and an organic light emitting luminescent device. As an example, a display device applying the OLED will be described. All the components of each display device according to all embodiments of the present disclosure are operatively coupled and configured.

Figure 1:
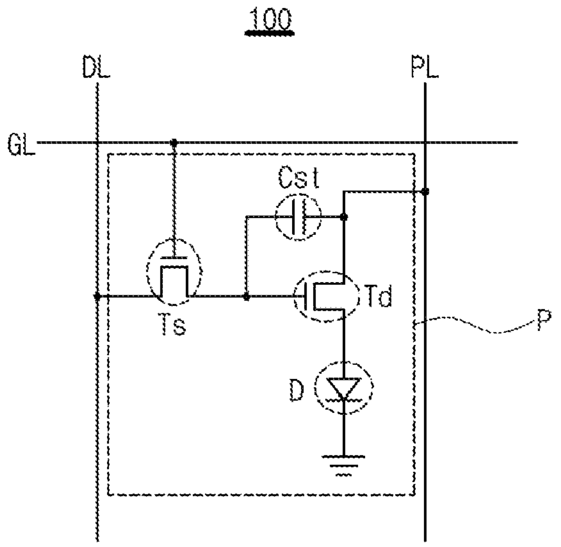
FIG. 1 is a schematic circuit diagram of an organic light emitting display device in accordance with the preset disclosure.
Figure 13:
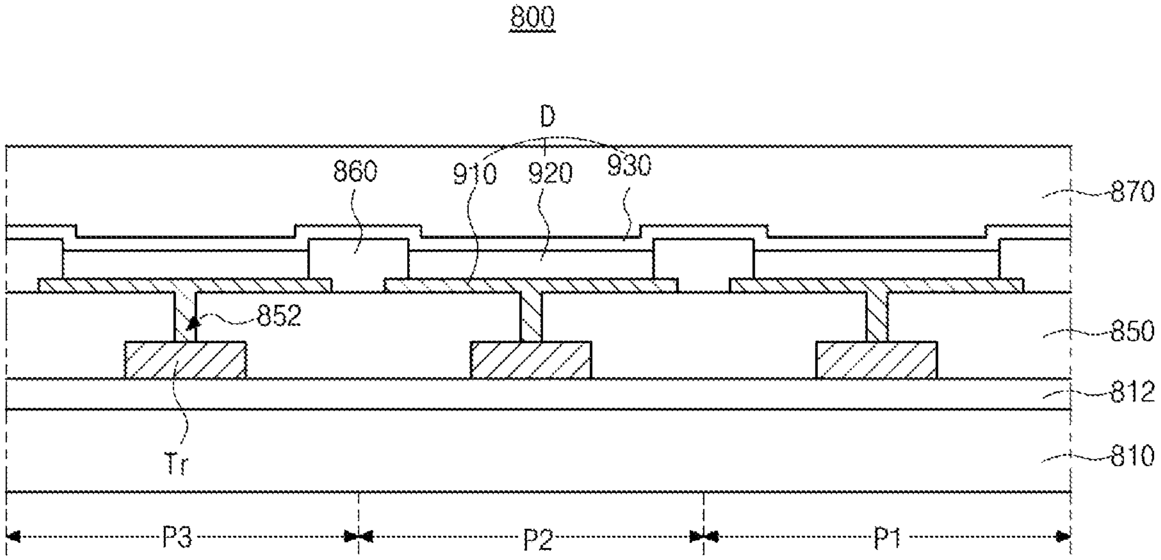
FIG. 13 is a schematic cross-sectional view illustrating an organic light emitting display device in accordance with another exemplary aspect of the present disclosure.

FIG. 1 is a schematic circuit diagram of an organic light emitting display device in accordance with the present disclosure. As illustrated in FIG. 1, a gate line GL, a data line DL and power line PL, each of which cross each other to define a pixel region P, in an organic light emitting display device 100. A switching thin film transistor Ts, a driving thin film transistor Td, a storage capacitor Cst and an organic light emitting diode D are formed within the pixel region P. The pixel region P can include a first pixel region P1, a second pixel region P2 and a third pixel region P3 (FIG. 13).

The switching thin film transistor Ts is connected to the gate line GL and the data line DL, and the driving thin film transistor Td and the storage capacitor Cst are connected between the switching thin film transistor Ts and the power line PL. The organic light emitting diode D is connected to the driving thin film transistor Td. When the switching thin film transistor Ts is turned on by a gate signal applied into the gate line GL, a data signal applied into the data line DL is applied into a gate electrode of the driving thin film transistor Td and one electrode of the storage capacitor Cst through the switching thin film transistor Ts.

The driving thin film transistor Td is turned on by the data signal applied into the gate electrode so that currents proportional to the data signal are supplied from the power line PL to the organic light emitting diode D through the driving thin film transistor Td. And then, the organic light emitting diode D emits light with a luminance proportional to the currents flowing through the driving thin film transistor Td. In this case, the storage capacitor Cst is charged with voltages proportional to the data signal so that the voltage of the gate electrode in the driving thin film transistor Td is kept constant during one frame. Therefore, the organic light emitting display device 100 can display a desired image.

Figure 2:
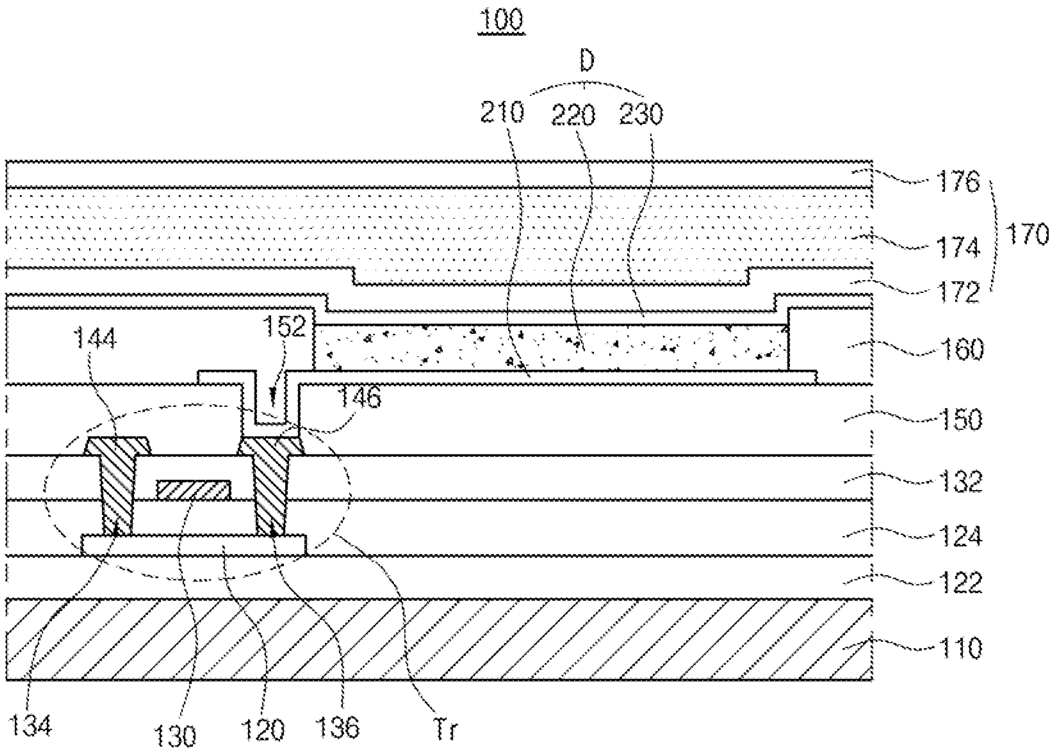
FIG. 2 is a schematic cross-sectional view illustrating an organic light emitting display device in accordance with an exemplary aspect of the present disclosure.

FIG. 2 is a schematic cross-sectional view of an organic light emitting display device 100 in accordance with an exemplary aspect of the present disclosure. All components of the organic light emitting device in accordance with all aspects of the present disclosure are operatively coupled and configured.

As illustrated in FIG. 2, the organic light emitting display device 100 includes a substrate 110, a thin-film transistor Tr on the substrate 110, and an organic light emitting diode (OLED) D over the substrate 110 and connected to the thin film transistor Tr.

The substrate 110 can include, but is not limited to, glass, thin flexible material and/or polymer plastics. For example, the flexible material can include, but is not limited to, polyimide (PI), polyethersulfone (PES), polyethylenenaphthalate (PEN), polyethylene terephthalate (PET), polycarbonate (PC) and combination thereof. The substrate 110, over which the thin film transistor Tr and the OLED D are arranged, form an array substrate.

A buffer layer 122 can be disposed over the substrate 110, and the thin film transistor Tr is disposed over the buffer layer 122. The buffer layer 122 can be omitted.

A semiconductor layer 120 is disposed over the buffer layer 122. In one exemplary aspect, the semiconductor layer 120 can include, but is not limited to, oxide semiconductor materials. In this case, a light-shield pattern can be disposed under the semiconductor layer 120, and the light-shield pattern can prevent light from being incident toward the semiconductor layer 120, and thereby, preventing the semiconductor layer 120 from being deteriorated by the light.

Alternatively, the semiconductor layer 120 can include, but is not limited to, polycrystalline silicon. In this case, opposite edges of the semiconductor layer 120 can be doped with impurities.

A gate insulating layer 124 made of an insulating material is disposed on the semiconductor layer 120. The gate insulating layer 124 can include, but is not limited to, an inorganic insulating material such as silicon oxide ($SiO_x$) or silicon nitride ($SiN_x$) ($0<x\leq 2$).

A gate electrode 130 made of a conductive material such as metal is disposed over the gate insulating layer 124 so as to correspond to a center of the semiconductor layer 120. While the gate insulating layer 124 is disposed over a whole area of the substrate 110 in FIG. 2, the gate insulating layer 124 can be patterned identically as the gate electrode 130.

An interlayer insulating layer 132 made of an insulating material is disposed on the gate electrode 130 with covering over an entire surface of the substrate 110. The interlayer insulating layer 132 can include, but is not limited to, an inorganic insulating material such as silicon oxide ($SiO_x$) or silicon nitride ($SiN_x$), or an organic insulating material such as benzocyclobutene or photo-acryl.

The interlayer insulating layer 132 has first and second semiconductor layer contact holes 134 and 136 that expose both sides of the semiconductor layer 120. The first and second semiconductor layer contact holes 134 and 136 are disposed over opposite sides of the gate electrode 130 with spacing apart from the gate electrode 130. The first and second semiconductor layer contact holes 134 and 136 are formed within the gate insulating layer 124 in FIG. 2. Alternatively, the first and second semiconductor layer contact holes 134 and 136 are formed only within the interlayer insulating layer 132 when the gate insulating layer 124 is patterned identically as the gate electrode 130.

A source electrode 144 and a drain electrode 146, which are made of conductive material such as a metal, are disposed on the interlayer insulating layer 132. The source electrode 144 and the drain electrode 146 are spaced apart from each other with respect to the gate electrode 130, and contact both sides of the semiconductor layer 120 through the first and second semiconductor layer contact holes 134 and 136, respectively.

The semiconductor layer 120, the gate electrode 130, the source electrode 144 and the drain electrode 146 constitute the thin film transistor Tr, which acts as a driving element. The thin film transistor Tr in FIG. 2 has a coplanar structure in which the gate electrode 130, the source electrode 144 and the drain electrode 146 are disposed over the semiconductor layer 120. Alternatively, the thin film transistor Tr can have an inverted staggered structure in which a gate electrode is disposed under a semiconductor layer and a source and drain electrodes are disposed over the semiconductor layer. In this case, the semiconductor layer can include amorphous silicon.

The gate line GL and the data line DL, which cross each other to define the pixel region P, and the switching element Ts, which is connected to the gate line GL and the data line DL, can be further formed in the pixel region P of FIG. 1. The switching element Ts is connected to the thin film transistor Tr, which is a driving element. Besides, the power line PL is spaced apart in parallel from the gate line GL or the data line DL, and the thin film transistor Tr can further include a storage capacitor Cst configured to constantly keep voltage of the gate electrode 130 for one frame.

A passivation layer 150 is disposed on the source and drain electrodes 144 and 146 over the whole substrate 110. The passivation layer 150 has a flat top surface and a drain contact hole 152 that exposes the drain electrode 146 of the thin film transistor Tr. While the drain contact hole 152 is disposed on the second semiconductor layer contact hole 136, it can be spaced apart from the second semiconductor layer contact hole 136.

The OLED D includes a first electrode 210 for example disposed on the passivation layer 150 and connected to the drain electrode 146 of the thin film transistor Tr. The OLED D further includes an emissive layer 220 and a second electrode 230 each of which is disposed sequentially on the first electrode 210.

The first electrode 210 is disposed in each pixel region. The first electrode 210 can be an anode and include a conductive material having a relatively high work function value. For example, the first electrode 210 can include, but is not limited to, a transparent conductive oxide (TCO).

In one exemplary aspect, when the organic light emitting display device 100 is a bottom-emission type, the first electrode 210 can have a single-layered structure of a transparent conductive material. Alternatively, when the organic light emitting display device 100 is a top-emission type, a reflective electrode or a reflective layer can be disposed under the first electrode 210. For example, the reflective electrode or the reflective layer can include, but is not limited to, silver (Ag) or aluminum-palladium-copper (APC) alloy. In the OLED D of the top-emission type, the first electrode 210 can have a triple-layered structure of ITO/Ag/ITO or ITO/APC/ITO.

In addition, a bank layer 160 is disposed on the passivation layer 150 in order to cover edges of the first electrode 210. The bank layer 160 exposes a center of the first electrode 210 corresponding to the pixel region P.

The emissive layer 220 is disposed on the first electrode 210. In one exemplary aspect, the emissive layer 220 can have a single-layered structure of an emitting material layer (EML). Alternatively, the emissive layer 220 can have a multiple-layered structure of a hole injection layer (HIL), a hole transport layer (HTL), an electron blocking layer (EBL), an EML, a hole blocking layer (HBL), an electron transport layer (ETL) and/or an electron injection layer (EIL) (see, FIGS. 3, 6, 9 and 12). In one aspect, the emissive layer 220 can have one emitting part. Alternatively, the emissive layer 220 can have multiple emitting parts to form a tandem structure.

The second electrode 230 is disposed over the substrate 110 above which the emissive layer 220 is disposed. The second electrode 230 can be disposed over a whole display area and can include a conductive material with a relatively low work function value compared to the first electrode 210. The second electrode 230 can be a cathode. When the organic light emitting display device 100 is a top-emission type, the second electrode 230 is thin so as to have light-transmissive (semi-transmissive) property.

In addition, an encapsulation film 170 can be disposed over the second electrode 230 in order to prevent outer moisture from penetrating into the OLED D. The encapsulation film 170 can have, but is not limited to, a laminated structure of a first inorganic insulating film 172, an organic insulating film 174 and a second inorganic insulating film 176.

Moreover, the organic light emitting display device 100 can have a polarizer in order to decrease external light reflection. For example, the polarizer can be a circular polarizer. When the organic light emitting display device 100 is a bottom-emission type, the polarizer can be disposed under the substrate 110. Alternatively, when the organic light emitting display device 100 is a top-emission type, the polarizer can be disposed over the encapsulation film 170. In addition, a cover window can be attached to the encapsulation film 170 or the polarizer. In this case, the substrate 110 and the cover window can have a flexible property, thus the organic light emitting display device 100 can be a flexible display device.

Figure 3:
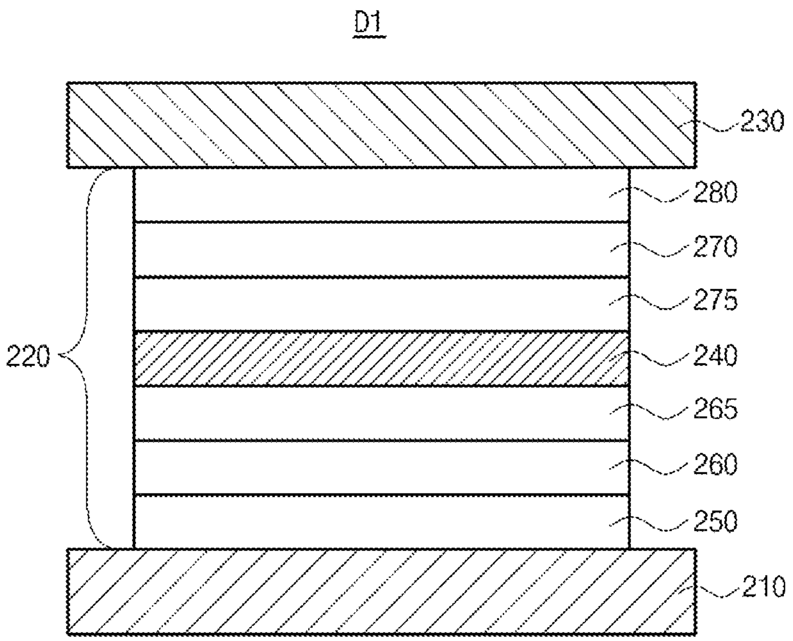
FIG. 3 is a schematic cross-sectional view illustrating an organic light emitting diode (OLED) in accordance with an exemplary aspect of the present disclosure.

Now, we will describe the OLED in more detail. FIG. 3 is a schematic cross-sectional view illustrating an OLED in accordance with an exemplary aspect of the present disclosure. As illustrated in FIG. 3, the OLED D1 comprises first and second electrodes 210 and 230 facing each other, and an emissive layer 220 having single emitting part disposed between the first and second electrodes 210 and 230. The organic light emitting display device 100 includes a red pixel region, a green pixel region and a blue pixel region, and the OLED D1 can be disposed in the red pixel region.

The emissive layer 220 includes an EML 240 disposed between the first and second electrodes 210 and 230. Also, the emissive layer 220 can include at least one of an HTL 260 disposed between the first electrode 210 and the EML 240 and an ETL 270 disposed between the second electrode 230 and the EML 240. In addition, the emissive layer 220 can further include at least one of an HIL 250 disposed between the first electrode 210 and the HTL 260 and an EIL 280 disposed between the second electrode 230 and the ETL 270. Alternatively, the emissive layer 220 can further include an EBL 265 disposed between the HTL 260 and the EML 240 and/or an HBL 275 disposed between the EML 240 and the ETL 270.

The first electrode 210 can be an anode that provides holes into the EML 240. The first electrode 210 can include, but is not limited to, a conductive material having a relatively high work function value, for example, a transparent conductive oxide (TCO). In an exemplary aspect, the first electrode 210 can include, but is not limited to, indium tin oxide (ITO), indium zinc oxide (IZO), indium tin zinc oxide (ITZO), tin oxide (SnO), zinc oxide (ZnO), cerium doped indium oxide (ICO), aluminum doped zinc oxide (Al: ZnO, AZO), and the like.

The second electrode 230 can be a cathode that provides electrons into the EML 240. The second electrode 230 can include, but is not limited to, a conductive material having a relatively low work function values, i.e., a highly reflective material such as Al, Mg, Ca, Ag, alloy thereof, combination thereof, and the like.

The EML 240 can include a first compound (Compound 1) DF1, a second compound (Compound 2) DF2, a third compound (Compound 3) FD and, optionally a fourth compound (Compound 4) H. For example, each of the first and second compounds DF1 and DF2 can be delayed fluorescent material, the third compound FD can be fluorescent material, and the fourth compound H can be host.

When holes and electrons meet each other to form excitons in the EML 240, singlet exciton with a paired spin state and triplet exciton with an unpaired spin state are generated in a ratio of 1:3 by spin arrangement. Since the conventional fluorescent materials can utilize only the singlet excitons, they exhibit low luminous efficiency. The phosphorescent materials can utilize the triplet excitons as well as the singlet excitons, while they show too short luminous lifespan to be applicable to commercial devices.

Figure 5:
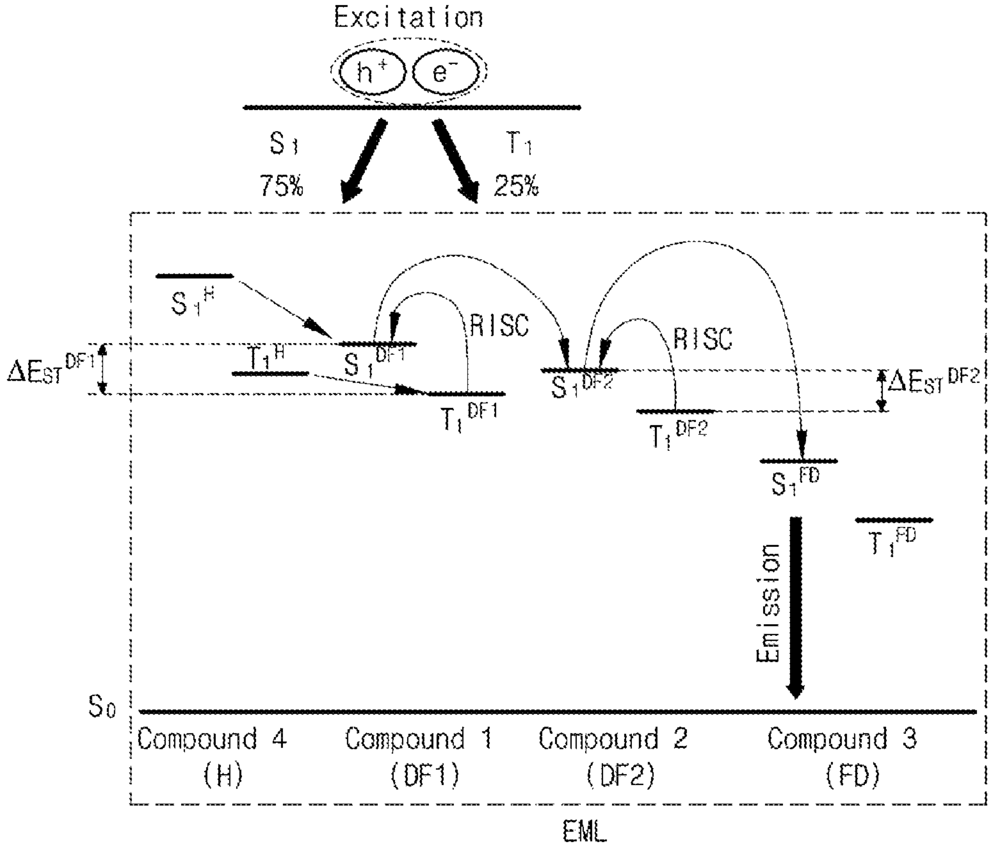
FIG. 5 is a schematic diagram illustrating luminous mechanism by singlet and triplet energy levels among luminous material in an EML in accordance with an exemplary aspect of the present disclosure.

Each of the first and second compounds DF1 and DF2 can be delayed fluorescent material having thermally activated delayed fluorescence (TADF) properties that can solve the problems accompanied by the conventional art fluorescent and/or phosphorescent materials. The delayed fluorescent material has very narrow energy level bandgap $\Delta E_{ST}^{DF1}$ or $\Delta E_{ST}^{DF2}$ between a singlet energy level $S_1^{DF1}$ or $S_1^{DF2}$ and a triplet energy level $T_1^{DF1}$ or $T_1^{DF2}$ (FIG. 5). Accordingly, the excitons of singlet energy level $S_1^{DF1}$ or $S_1^{DF2}$ as well as the excitons of triplet energy level $T_1^{DF1}$ or $S_1^{DF2}$ in the first and second compounds DF1 and DF2 of the delayed fluorescent material can be transferred to an intermediate energy level state, i.e. ICT (intramolecular charge transfer) state ($S_1 \rightarrow ICT \leftarrow T_1$), and then the intermediate state excitons can be shifted to a ground state ($ICT \rightarrow S_0$).

Since the delayed fluorescent material includes the electron acceptor moiety is spaced apart from the electron donor moiety within the molecule, dipole moment intra-molecular conformation exists in a highly polarized state. The dipole moment in a highly polarized state allows a Highest Occupied Molecular Orbital (HOMO) to interact little with a Lowest Unoccupied Molecular Orbital (LUMO) and to have ICT property in which triplet exciton energy and singlet exciton energy can be transferred therebetween.

The delayed fluorescent material must has an energy level bandgap $\Delta E_{ST}^{DF1}$ or $\Delta E_{ST}^{DF2}$ (FIG. 5) equal to or less than about 0.3 eV, for example, from about 0.05 to about 0.3 eV, between the singlet energy level $S_1^{DF1}$ or $S_1^{DF2}$ and the triplet energy level $T_1^{DF1}$ or $T_1^{DF2}$ so that exciton energy in both the singlet energy level $S_1^{DF1}$ or $S_1^{DF2}$ and the triplet energy level $T_1^{DF1}$ or $T_1^{DF2}$ can be transferred to the ICT state. The material having little energy level bandgap $\Delta E_{ST}$ between the singlet energy level $S_1$ and the triplet energy level $T_1$ can exhibit common fluorescence with Inter system Crossing (ISC) in which the excitons of singlet energy level $S_1$ can be shifted to its ground state $S_0$, as well as delayed fluorescence with Reverse Inter System Crossing (RISC) in which the excitons of triplet energy level $T_1$ can be converted upwardly to the excitons of singlet energy level $S_1$, and then the exciton of singlet energy level $S_1$ transferred from the triplet energy level $T_1$ can be transferred to the ground state $S_0$.

In other words, in the first and second compounds DF1 and DF2 of the delayed fluorescent material, exciton of 25% singlet energy level $S_1^{DF1}$ or $S_1^{DF2}$ as well as exciton of 75% triplet energy level $T_1^{DF1}$ or $T_1^{DF1}$ is transferred to the ICT state, and then excitons at ICT state drop to its ground state $S_0$ with light emission. The delayed fluorescent material exhibit an internal quantum efficiency of 100% in theory, it can implement luminous efficiency as the prior art phosphorescent material.

The first compound DF1 included in the EML 240 can be delayed fluorescent material where a benzene ring is substituted with two cyano groups linked at meta-position and 1 to 4 carbazolyl groups. The first compound DF1 having the delayed fluorescent property can have the following structure of Formula 1 or a structure formed by linking two structures of Formula 1 via a direct or indirect bond:

[Formula 1]

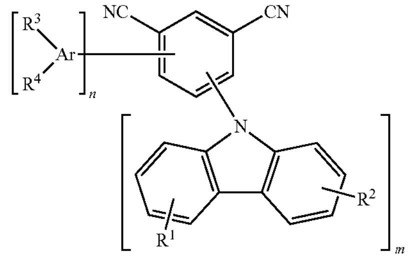

wherein, in Formula 1, each of $R^1$ and $R^2$ is independently hydrogen, deuterium, tritium, unsubstituted or substituted $C_1$-$C_{20}$ alkyl, an unsubstituted or substituted $C_6$-$C_{30}$ aromatic group or an unsubstituted or substituted $C_3$-$C_{30}$ hetero aromatic group;

each of $R^3$ and $R^4$ is independently an unsubstituted or substituted carbazolyl group;

Ar is an unsubstituted or substituted $C_6$-$C_{30}$ aromatic ring or an unsubstituted or substituted $C_3$-$C_{30}$ hetero aromatic group;

m is an integer of 1 to 4; and n is an integer of 0 to 1, wherein m plus n is an integer of 1 to 4.

As used herein, substituent in the term "substituted" includes, but is not limited to, deuterium, tritium, unsubstituted or deuterium or halogen-substituted $C_1$-$C_{20}$ alkyl, unsubstituted or deuterium or halogen-substituted $C_1$-$C_{20}$ alkoxy, halogen, cyano, —$CF_3$, a hydroxyl group, a carboxylic group, a carbonyl group, an amino group, a $C_1$-$C_{10}$ alkyl amino group, a $C_6$-$C_{30}$ aryl amino group, a $C_3$-$C_{30}$ hetero aryl amino group, a $C_6$-$C_{30}$ aryl group, a $C_3$-$C_{30}$ hetero aryl group, a nitro group, a hydrazyl group, a sulfonate group, a $C_1$-$C_{20}$ alkyl silyl group, a $C_6$-$C_{30}$ aryl silyl group and a $C_3$-$C_{30}$ hetero aryl silyl group.

For example, each of the $C_6$-$C_{30}$ aromatic group, the $C_3$-$C_{30}$ hetero aromatic group, the $C_6$-$C_{20}$ aromatic ring and the $C_3$-$C_{20}$ hetero aromatic ring of $R^1$, $R^2$ or Ar in Formula 1 can be independently unsubstituted or substituted with, but is not limited to, at least one of $C_1$-$C_{20}$ alkyl, cyano, $C_6$-$C_{20}$ aryl and $C_3$-$C_{20}$ hetero aryl.

As used herein, the term "aromatic" or "aryl" is well known in the art. The term includes monocyclic rings linked covalently or fused-ring polycyclic groups. As used herein, the term $C_6$-$C_{30}$ aromatic group or the $C_6$-$C_{20}$ aromatic ring can include independently, but is not limited to, $C_6$-$C_{30}$ aryl, $C_7$-$C_{30}$ aryl alkyl, $C_6$-$C_{30}$ aryl oxy, $C_6$-$C_{30}$ aryl amino, $C_7$-$C_{30}$ aryl ester and $C_8$-$C_{30}$ vinyl aryl. The aromatic group, the aromatic ring and/or the aryl can be unsubstituted or substituted with at least one of $C_1$-$C_{20}$ alkyl, $C_6$-$C_{30}$ aryl and/or $C_3$-$C_{30}$ hetero aryl.

As an example, the $C_6$-$C_{30}$ aromatic group and/or the $C_6$-$C_{30}$ aryl group, which can constitute $R^1$ and/or $R^2$ in Formula 1, can include independently, but is not limited to, a non-fused or fused aryl group such as phenyl, biphenyl, terphenyl, naphthyl, anthracenyl, pentalenyl, indenyl, indeno-indenyl, heptalenyl, biphenylenyl, indacenyl, phenalenyl, phenanthrenyl, benzo-phenanthrenyl, dibenzo-phenanthrenyl, azulenyl, pyrenyl, fluoranthenyl, triphenylenyl, chrysenyl, tetraphenylenyl, tetracenyl, pleiadenyl, picenyl, pentaphenylenyl, pentacenyl, fluorenyl, indeno-fluorenyl and spiro-fluorenyl.

As used herein, the term "hetero aromatic" or "hetero aryl" refers to a heterocycles including hetero atoms selected from N, O and S in a ring where the ring system is an aromatic ring. The term includes monocyclic rings linked covalently or fused-ring polycyclic groups. As used herein, the term $C_3$-$C_{30}$ hetero aromatic group or the $C_3$-$C_{20}$ hetero aromatic ring can include independently, but is not limited to, $C_3$-$C_{30}$ hetero aryl, $C_4$-$C_{30}$ hetero aryl alkyl, $C_3$-$C_{30}$ hetero aryl oxy, $C_3$-$C_{30}$ hetero aryl amino, $C_4$-$C_{30}$ hetero aryl ester and $C_5$-$C_{30}$ hetero vinyl aryl. The hetero aromatic group, the hetero aromatic ring and/or the hetero aryl can be unsubstituted or substituted with at least one of $C_1$-$C_{20}$ alkyl, $C_6$-$C_{30}$ aryl and/or $C_3$-$C_{30}$ hetero aryl.

As an example, the $C_3$-$C_{30}$ hetero aromatic group and/or the $C_3$-$C_{30}$ hetero aryl group, which can constitute $R^1$ and/or $R^2$ in Formula 1, can include independently, but is not limited to, an unfused or fused hetero aryl group such as pyrrolyl, pyridinyl, pyrimidinyl, pyrazinyl, pyridazinyl, triazinyl, tetrazinyl, imidazolyl, pyrazolyl, indolyl, iso-indolyl, indazolyl, indolizinyl, pyrrolizinyl, carbazolyl, benzo-carbazolyl, dibenzo-carbazolyl, indolo-carbazolyl, indeno-carbazolyl, benzo-furo-carbazolyl, benzo-thieno-carbazolyl, carbolinyl, quinolinyl, iso-quinolinyl, phthalazinyl, quinoxalinyl, cinnolinyl, quinazolinyl, quinolizinyl, purinyl, benzo-quinolinyl, benzo-iso-quinolinyl, benzo-quinazolinyl, benzo-quinoxalinyl, acridinyl, phenazinyl, phenoxazinyl, phenothiazinyl, phenanthrolinyl, perimidinyl, phenanthridinyl, pteridinyl, naphthyridinyl, furanyl, pyranyl, oxazinyl, oxazolyl, oxadiazolyl, triazolyl, dioxanyl, benzo-furanyl, dibenzo-furanyl, thiopyranyl, xanthenyl, chromenyl, iso-chromenyl, thiazinyl, thiophenyl, benzo-thiophenyl, dibenzo-thiophenyl, difuro-pyrazinyl, benzo-furo-dibenzo-furanyl, benzothieno-benzo-thiophenyl, benzothieno-dibenzo-thiophenyl, benzothieno-benzo-furanyl, benzothieno-dibenzo-furanyl, N-substituted spiro-fluorenyl, spiro-fluoreno-acridinyl and spiro-fluoreno-xanthenyl.

In one exemplary aspect, m of the number of an electron donor moiety of the first compound DF1 having the structure of Formula 1 can be, but is not limited to, an integer of 2 to 4, for example, 2 or 4, and n can be, but is not limited to, 0 or 1. As an example, each of $R^1$ and $R^2$ can be independently, but is not limited to, hydrogen, deuterium, tritium, $C_1$-$C_5$ alkyl (e.g. methyl, ethyl, t-butyl) or $C_6$-$C_{20}$ aryl (e.g. phenyl). Each of $R^3$ and $R^4$ can be independently, but is not limited to, carbazolyl unsubstituted or substituted with at least one, for example, at least two of $C_1$-$C_5$ alkyl (e.g. methyl, ethyl, t-butyl) and/or $C_6$-$C_{20}$ aryl (e.g. phenyl). Ar in Formula 1 can be, but is not limited to, a $C_6$-$C_{15}$ aromatic ring (e.g. benzene ring) unsubstituted or substituted with at least one cyano group, for example, 1-3 cyano groups.

As an example, the first compound DF1 can be selected from, but is not limited to, an organic compound having the following structure of Formula 2:

[Formula 2]

1-1

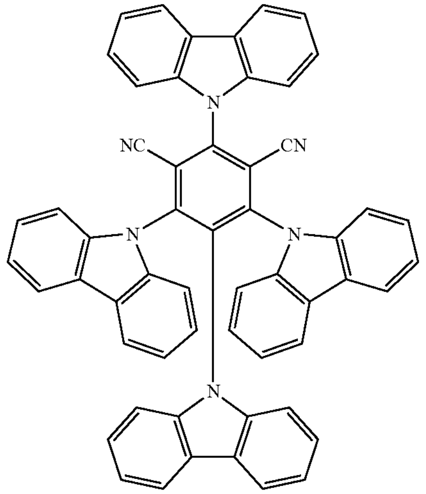

1-2
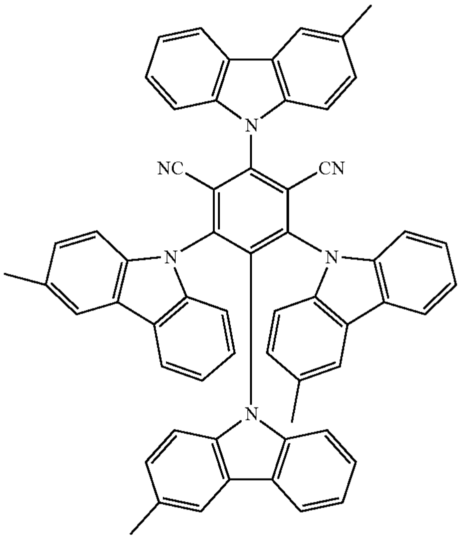
1-3
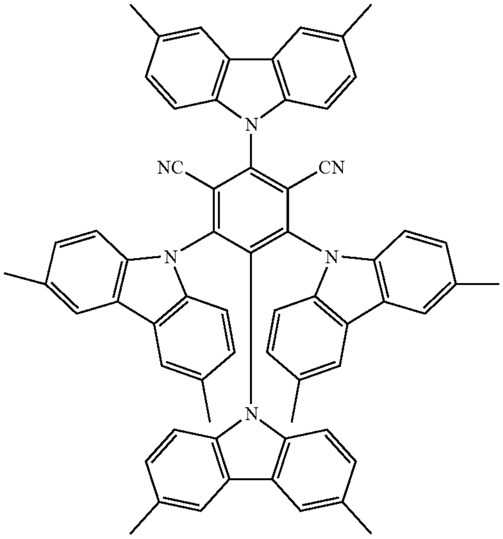
1-4
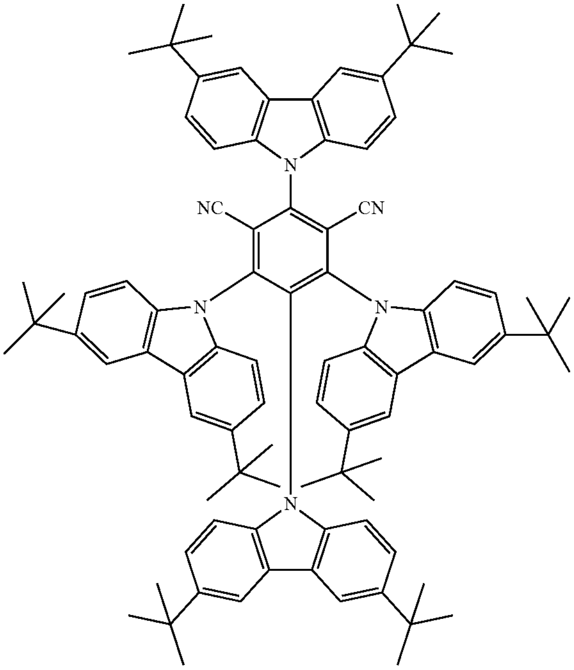
1-5
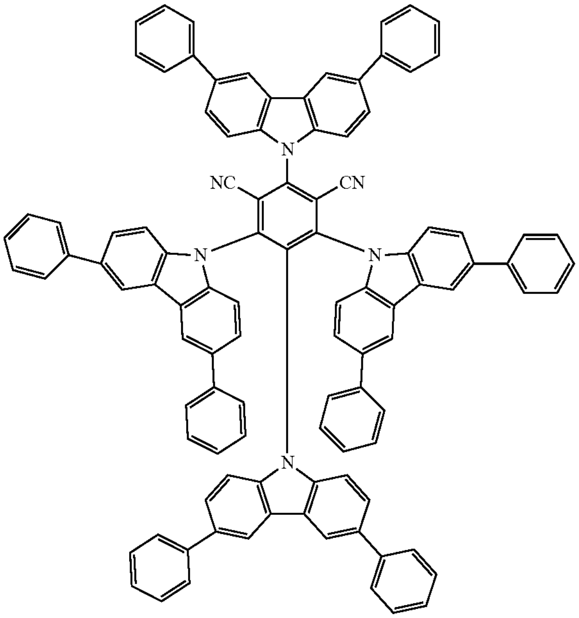

-continued
1-6
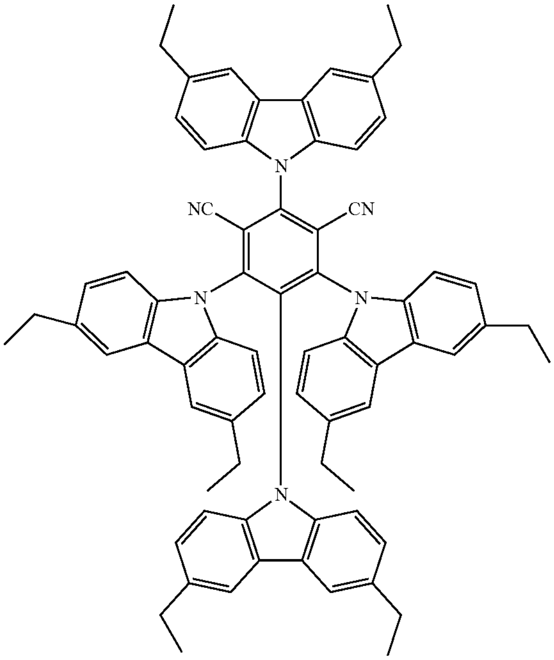
1-7
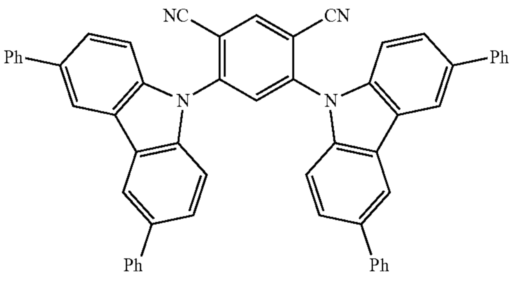
1-8
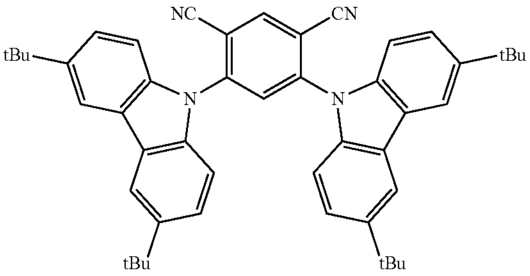
-continued
1-9
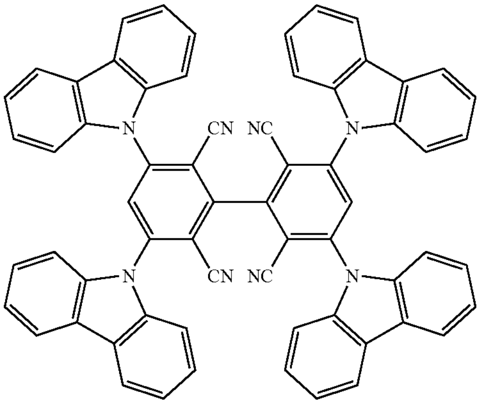
1-10
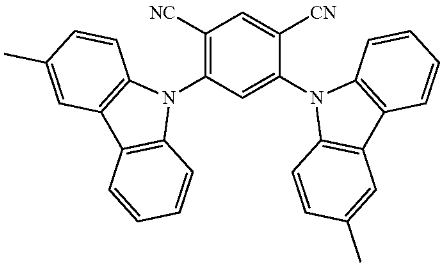
1-11
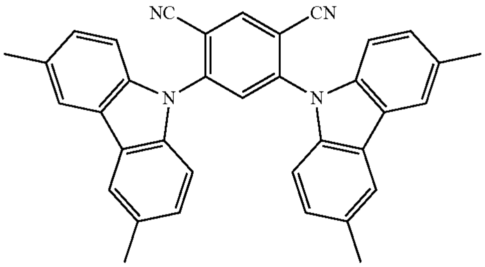
1-12
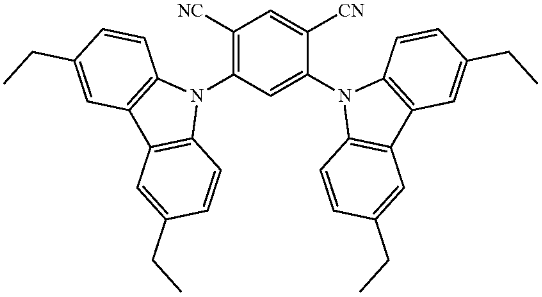

-continued 1-13

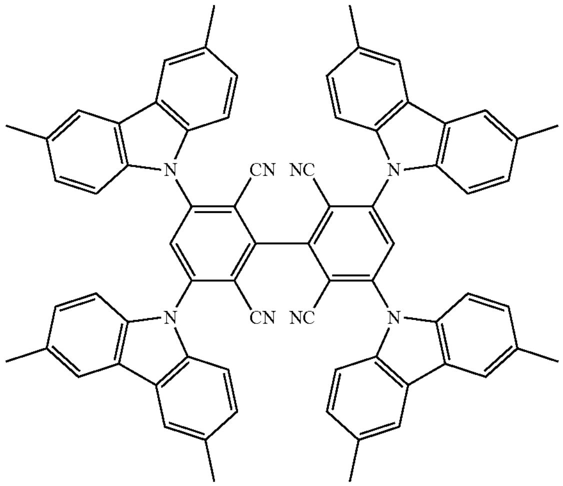

1-14

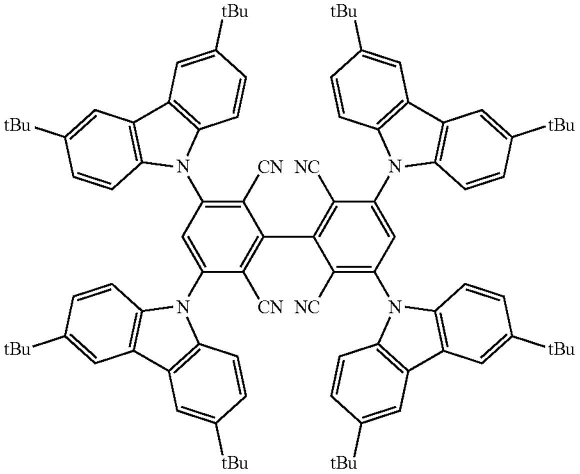

1-15

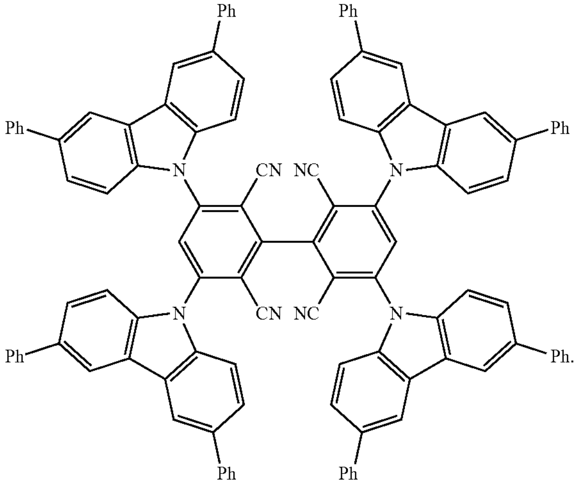

The second compound DF2 can be delayed florescent material where a benzene ring is substituted with two cyano groups linked at para position and 1 to 4 carbazolyl groups. The second compound DF2 having the delayed fluorescent property can have the following structure of Formula 3:

[Formula 3]

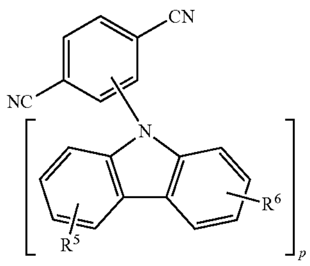

wherein, in Formula 3, each of $R^5$ and $R^6$ is independently hydrogen, deuterium, tritium, unsubstituted or substituted $C_1$-$C_{20}$ alkyl, an unsubstituted or substituted $C_6$-$C_{30}$ aromatic group or an unsubstituted or substituted $C_3$-$C_{30}$ hetero aromatic group, wherein at least one of $R^5$ and $R^6$ is an unsubstituted or substituted $C_1$-$C_{20}$ alkyl, an unsubstituted or substituted $C_6$-$C_{30}$ aromatic group or an unsubstituted or substituted $C_3$-$C_{30}$ hetero aromatic group; and p is an integer of 1 to 4.

As an example, each of the $C_6$-$C_{30}$ aromatic group and the $C_3$-$C_{30}$ hetero aromatic group of $R^5$ and $R^6$ can be independently unsubstituted or substituted with at least one of $C_1$-$C_{20}$ alkyl, $C_6$-$C_{20}$ aryl and $C_3$-$C_{20}$ hetero aryl.

In one exemplary aspect, p of the number of an electron donor moiety of the second compound DF2 having the structure of Formula 3 can be, but is not limited to, an integer of 2 to 4, for example, 2 or 4. As an example, each of $R^5$ and $R^6$ can be independently, but is not limited to, hydrogen, deuterium, tritium, $C_1$-$C_5$ alkyl (e.g. methyl, ethyl, t-butyl) or $C_6$-$C_{20}$ aryl (e.g. phenyl). For example, the second compound DF2 can be selected from, but is not limited to, an organic compound having the following structure of Formula 4:

2-1

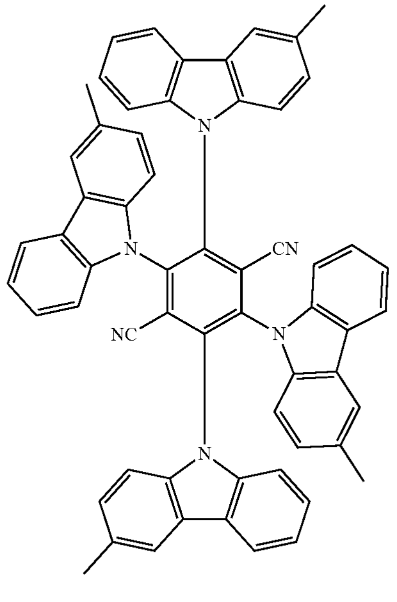

-continued
2-2
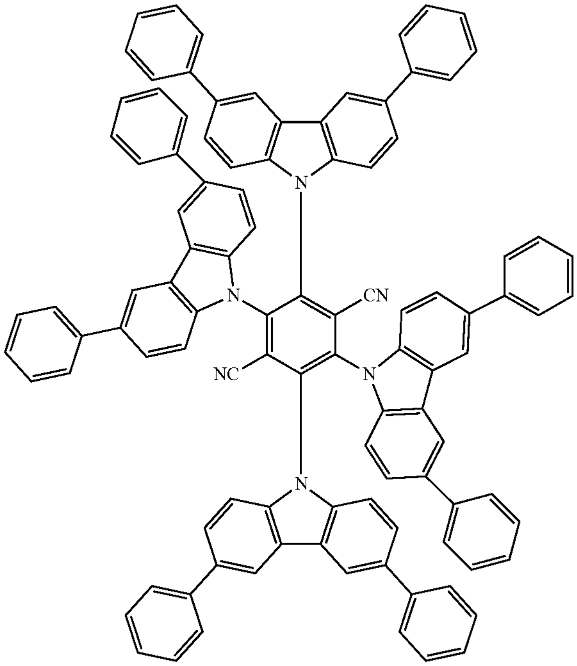
2-3
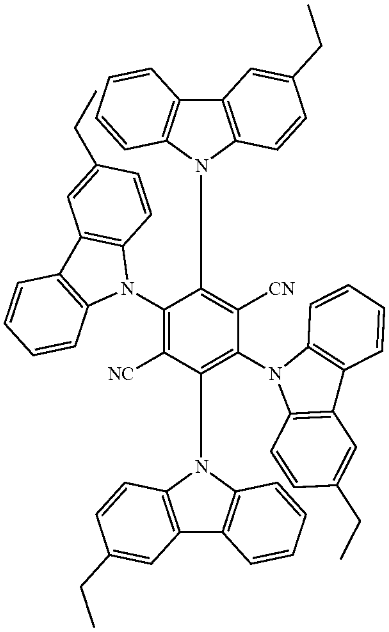
-continued
2-1
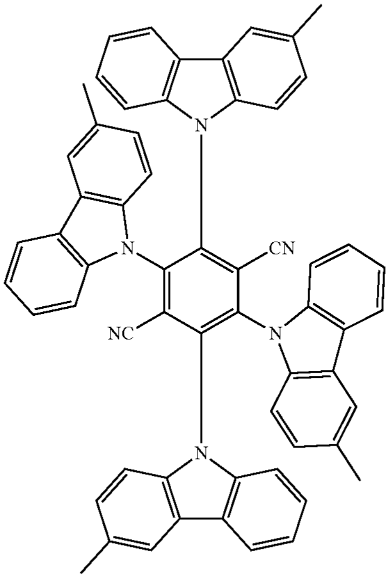
2-2
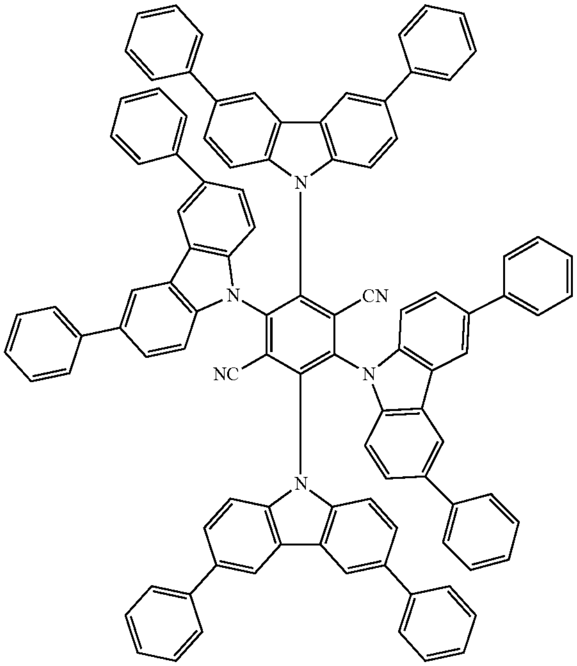

-continued
2-3
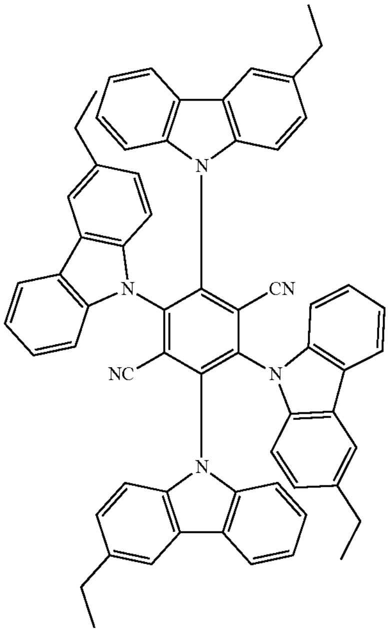
2-7
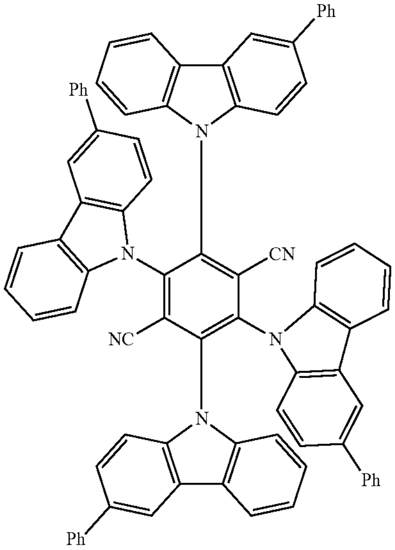
-continued
2-8
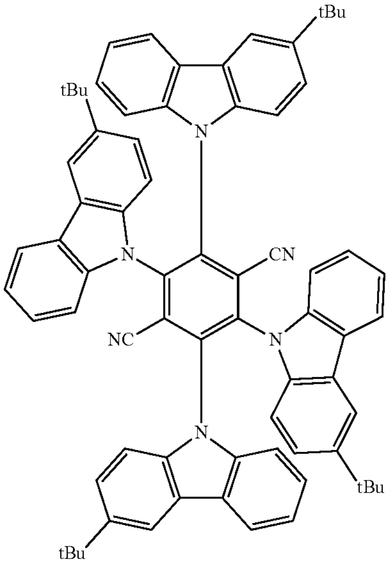
2-9
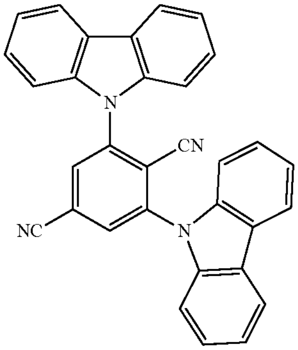
2-10
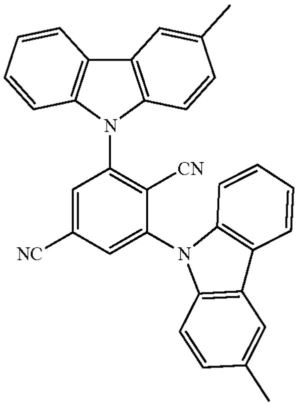

-continued
2-11
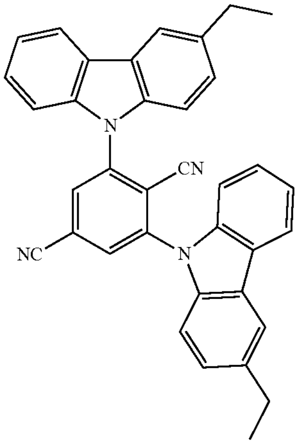
2-12
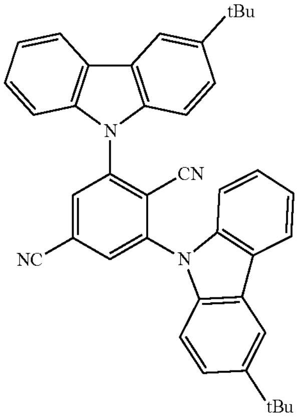
2-13
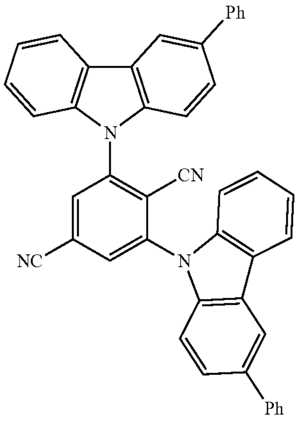
-continued
2-14
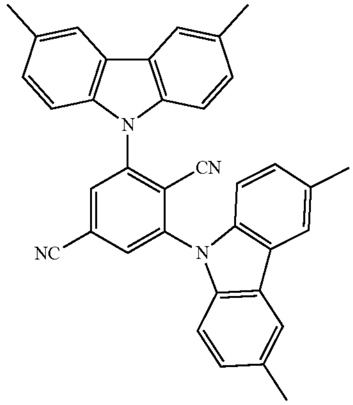
2-15
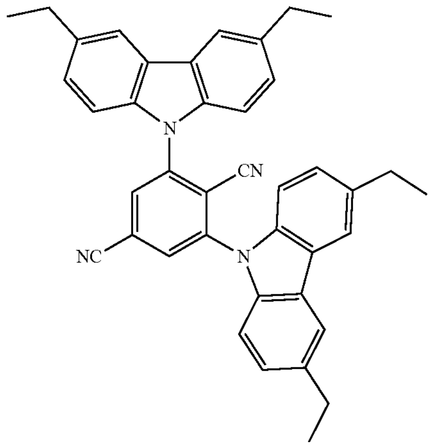
2-16
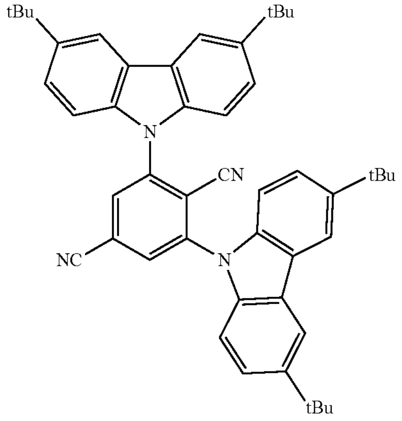

-continued 2-17

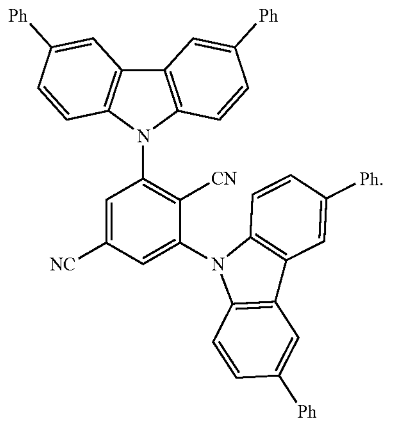

The organic compound having the structure of Formulae 1 to 4 has delayed fluorescent property as well as a singlet exciton energy level, a triplet exciton energy level, a HOMO energy level and a LUMO energy level appropriate for transferring efficiently exciton energies to the third compound FD, as described below.

The first and second compounds DF1 and DF2 of the delayed fluorescent material has little energy bandgap $\Delta E_{ST}^{DF1}$ or $\Delta E_{ST}^{DF2}$ between the excited singlet energy level $S_1^{DF1}$ or $S_1^{DF2}$ and the excited triplet energy level $T_1^{DF1}$ or $T_1^{DF2}$ of equal to or less than about 0.3 eV (FIG. 7) and shows excellent quantum efficiency because the excited triplet exciton energies of the first and second compounds DF1 and DF2 are converted to the excited singlet exciton of the third compound FD by RISC.

Each of the first and second compounds DF1 and DF2 having the structure of Formulae 1 to 4 has a distorted chemical conformation due to the binding structure between the electron donor moiety and the electron acceptor moiety. Since the first and second compounds DF1 and DF2 utilize triplet excitons, addition charge transfer transition (CT transition) is induced in the first and second compounds DF1 and DF2. Each of the first and second compounds DF1 and DF2 having the structure of Formulae 1 to 4 has wide full-width at half maximum (FWHM) so that they have limitation in color purity due to the luminous properties caused by the CT luminous mechanism.

The EML 240 includes the third compound FD of the fluorescent material in order to maximize the luminous property of the first and second compounds DF1 and DF2 of the delayed fluorescent material and to implement hyper-fluorescence. As described above, each of the first and second compounds DF1 and DF2 of the delayed fluorescent material can utilize both the singlet exciton energy and the triplet exciton energy. When the EML 240 includes the third compound FD of the fluorescent material having proper energy levels compared to each of the first and second compounds DF1 and DF2 of the delayed fluorescent material, the third compound FD can absorb exciton energies released from the first compound DF1 via the second compound DF2, and then the third compound FD can generate 100% singlet excitons utilizing the absorbed exciton energies with maximizing its luminous efficiency.

The singlet exciton energy of the first and second compounds DF1 and DF2, which includes the singlet exciton energy of the first and second compounds DF1 and DF2 converted from its own triplet exciton energy and initial singlet exciton energy of the first and second compounds DF1 and DF2 in the EML 240, is transferred to the third compound FD of the fluorescent material in the same EML 240 via Forster resonance energy transfer (FRET) mechanism, and the ultimate emission is occurred at the third compound FD. Organic material having an absorption spectrum widely overlapped with a photoluminescence spectrum of the first and second compounds DF1 and DF2, particularly, the second compound DF2, can be used as the third compound FD so that the exciton energy generated at the first and second compounds DF1 and DF2 can be efficiently transferred to the third compound FD. Since the third compound FD emits light with singlet excitons shifted from the excited state to the ground state, not CT luminous mechanism, it has narrow FWHM for improving color purity thereof.

The third compound FD in the EML 240 can be red fluorescent material. For example, the third compound FD can be an organic compound having a BODIPY (boron-dipyrromethene)-based fluorescent material with narrow FWHM. As an example, the third compound of BODIPY-based fluorescent material can have the following structure of Formula 5:

[Formula 5]

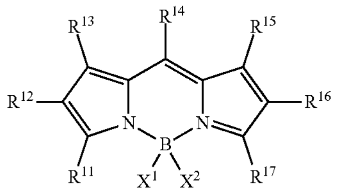

wherein, in Formula 5, each of $R^{11}$ to $R^{17}$ is independently hydrogen, deuterium, tritium, an unsubstituted or substituted $C_1$-$C_{20}$ alkyl, an unsubstituted or substituted $C_6$-$C_{30}$ aromatic group or an unsubstituted or substituted $C_3$-$C_{30}$ hetero aromatic group; and each of $X^1$ and $X^2$ is independently a halogen atom.

As an example, each of the $C_6$-$C_{30}$ aromatic group and the $C_3$-$C_{30}$ hetero aromatic group of $R^{11}$ to $R^{17}$ can be independently unsubstituted or substituted with at least one of $C_1$-$C_{20}$ alkyl, $C_1$-$C_{20}$ alkoxy, $C_6$-$C_{20}$ aryl and $C_3$-$C_{20}$ hetero aryl.

In an exemplary aspect, at least two, for example, three or four, among $R^{11}$ to $R^{17}$ in Formula 5 can be the unsubstituted or substituted $C_6$-$C_{30}$ aromatic group or the unsubstituted or substituted $C_3$-$C_{30}$ hetero aromatic group as the third compound FD emitting red wavelength light. As an example, each of $R^{11}$, $R^{13}$, $R^{14}$, $R^{15}$ and $R^{17}$ in Formula 5 can be independently unsubstituted or substituted $C_6$-$C_{30}$ aryl or unsubstituted or substituted $C_3$-$C_{30}$ hetero aryl, and each of $R^{12}$ and $R^{16}$ in Formula 5 can be independently hydrogen, deuterium, tritium or unsubstituted or substituted $C_1$-$C_{10}$ alkyl. In an exemplary aspect, the third compound FD can be selected from, but is not limited to, an organic compound having the following structure of Formula 6:

[Formula 6]
3-1
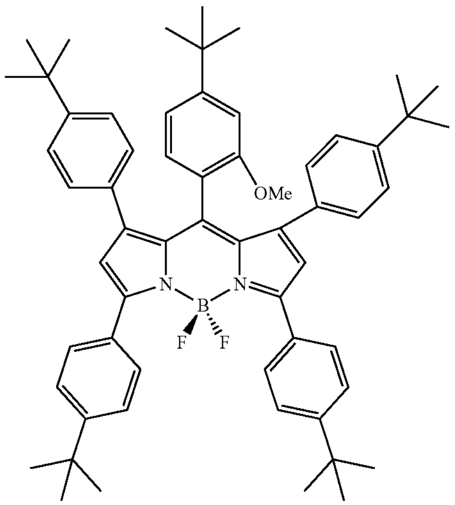
3-2
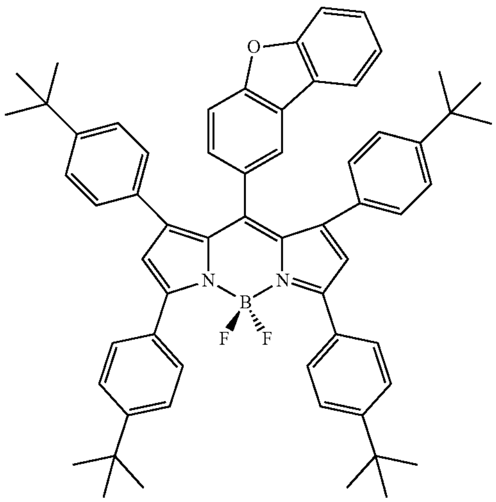
3-3
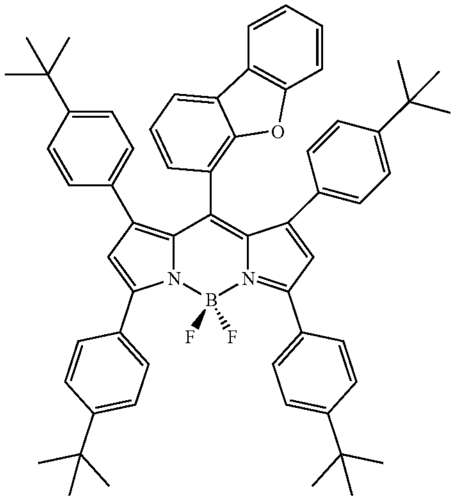
-continued
3-4
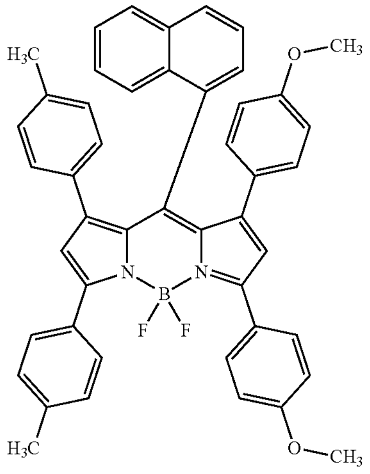
3-5
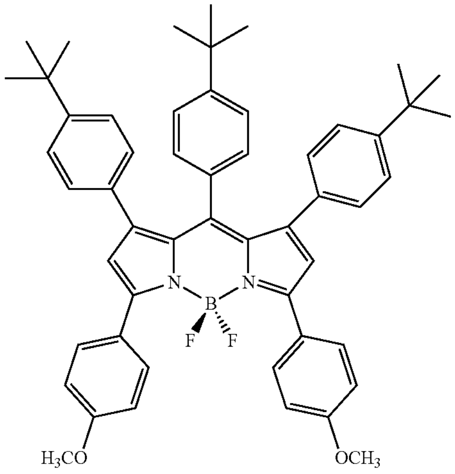
3-6
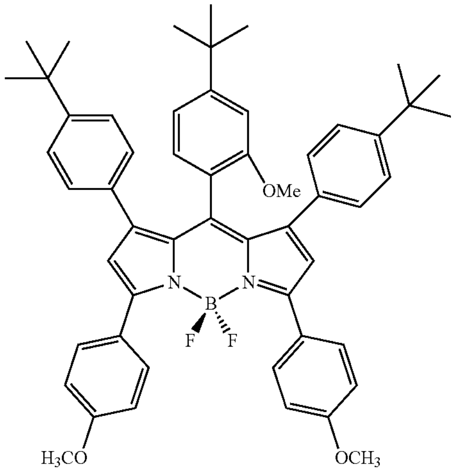

-continued
3-7
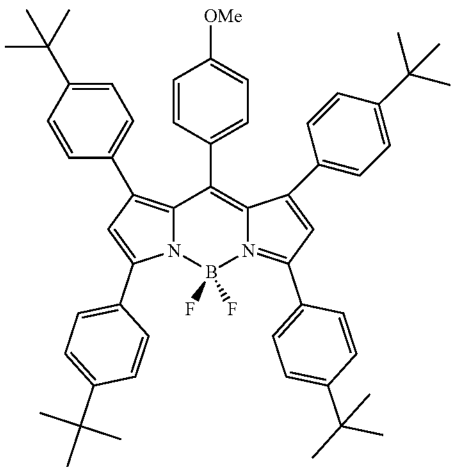
3-8
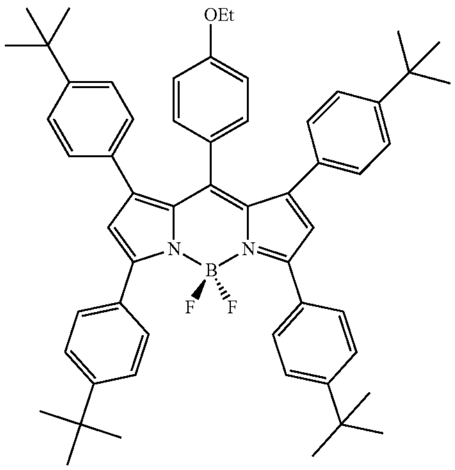
3-9
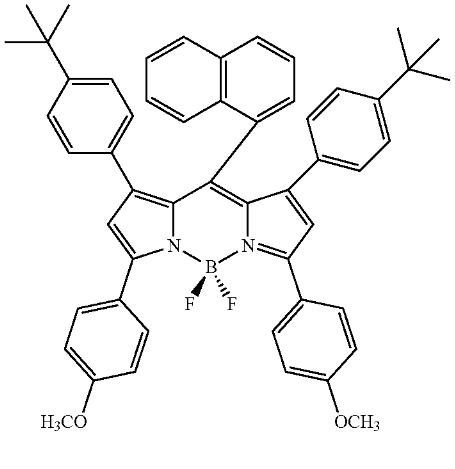
-continued
3-10
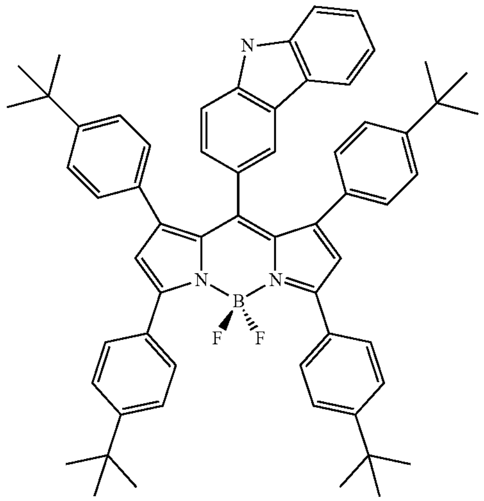
3-11
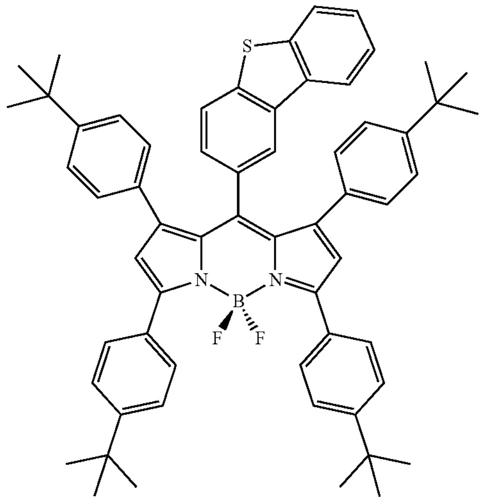
3-12
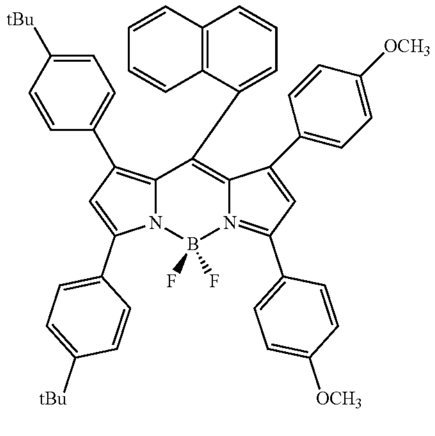

-continued 3-13

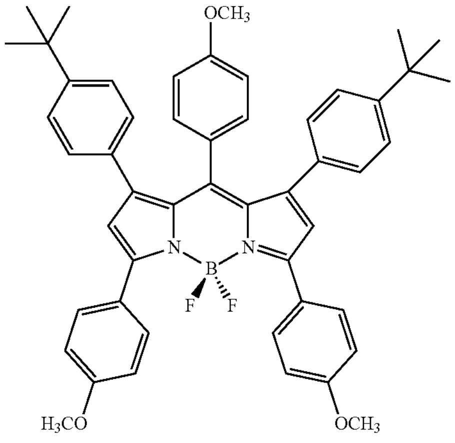

3-14

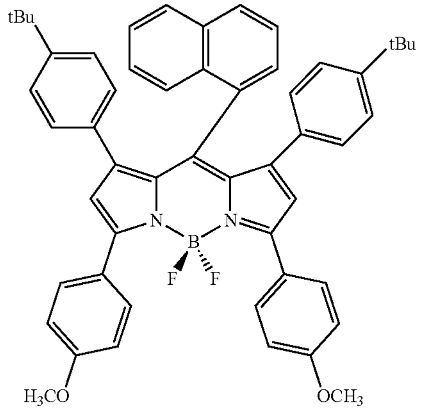

3-15

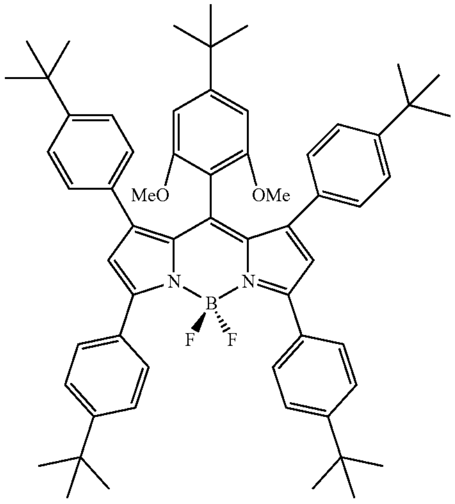

The fourth compound H in the EML 240 can include any organic compound having wider energy level bandgap between a HOMO energy level and a LUMO energy level compared to the first and second compounds DF1 and DF2 and/or the third compound FD. As an example, when the EML 240 includes the fourth compound H of the host, the first compound DF1 can be a first dopant, the second compound DF2 can be a second dopant, and the third compound FD can be a third dopant.

In an exemplary aspect, the fourth compound H, which can be included in the EML 240, can include, but is not limited to, 4,4'-bis(N-carbazolyl)-1,1'-biphenyl (CBP), 3,3'-bis(N-carbazolyl)-1,1'-biphenyl (mCBP), 1,3-Bis(carbazol-9-yl)benzene (mCP), 9-(3-(9H-carbazol-9-yl)phenyl)-9H-carbazole-3-carbonitrile (mCP-CN), Oxybis(2,1-phenylene))bis(diphenylphosphine oxide (DPEPO), 2,8-bis (diphenylphosphoryl)dibenzothiophene (PPT), 1,3,5-Tri[(3-pyridyl)-phen-3-yl]benzene (TmPyPB), 2,6-Di(9H-carbazol-9-yl)pyridine (PYD-2Cz), 2,8-di(9H-carbazol-9-yl)dibenzothiophene (DCzDBT), 3',5'-Di(carbazol-9-yl)-[1,1'-bipheyl]-3,5-dicarbonitrile (DCzTPA), 4'-(9H-carbazol-9-yl)biphenyl-3,5-dicarbonitrile(4'-(9H-carbazol-9-yl) biphenyl-3,5-dicarbonitrile (pCzB-2CN), 3'-(9H-carbazol-9-yl)biphenyl-3,5-dicarbonitrile (mCzB-2CN), Diphenyl-4-triphenylsilylphenyl-phosphine oxide (TSPO1), 9-(9-phenyl-9H-carbazol-6-yl)-9H-carbazole (CCP), 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole, 9-(6-(9H-carbazol-9-yl)pyridin-3-yl)-9H-3,9'-bicabazole and combination thereof.

For example, the fourth compound H can have the following structure of Formula 7:

[Formula 7]

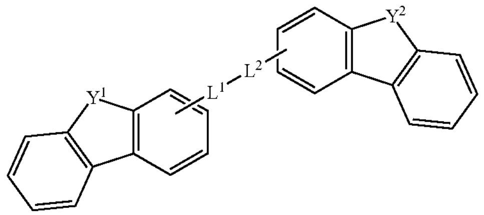

wherein, in Formula 7, each of $Y^1$ and $Y^2$ is independently $CR^{21}R^{22}$, N, O or S, when each of $Y^1$ and $Y^2$ is independently $CR^{21}R^{22}$, O or S, each of $L_1$ and $L_2$ is linked to a benzene ring of each fused ring, respectively, when each of $Y^1$ and $Y^2$ is independently N, each of $L_1$ and $L_2$ is linked to each of $Y^1$ and $Y_2$ of each fused ring, respectively; and each of $R^{21}$ and $R^{22}$ is independently hydrogen, deuterium, tritium or unsubstituted or substituted $C_1$-$C_{10}$ alkyl; and each of $L^1$ and $L^2$ is independently a single bond, unsubstituted or substituted $C_6$-$C_{20}$ arylene or unsubstituted or substituted $C_3$-$C_{20}$ hetero arylene, wherein at least one of $L^1$ and $L^2$ is not a single bond.

As an example, each of $Y^1$ and $Y^2$ can be independently N, O or S and each of $L^1$ and $L^2$ can be independently a single bond, phenylene, dibenzofuranylene or dibenzothiophenylene. The fourth compound H having the structure of Formula 7 can be selected from, but is not limited to, an organic compound having the following structure of Formula 8:

[Formula 8]

4-1

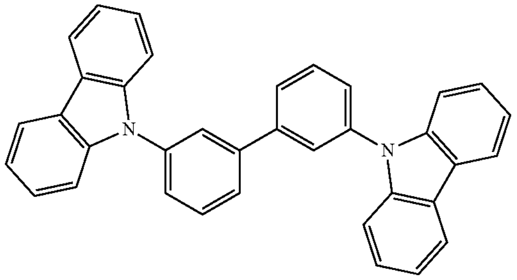

4-2

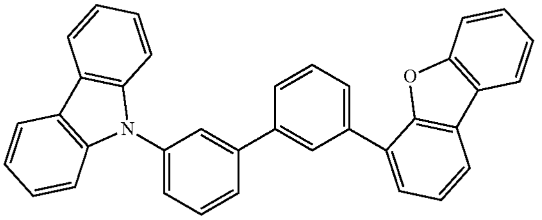

4-3

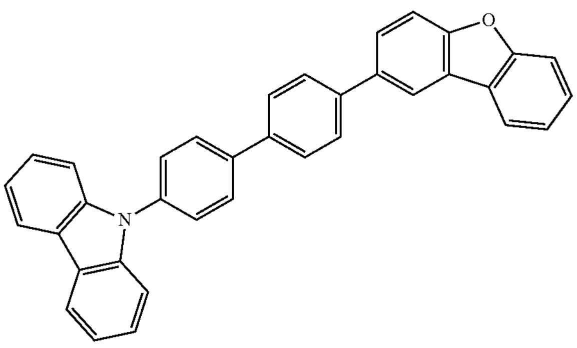

4-4

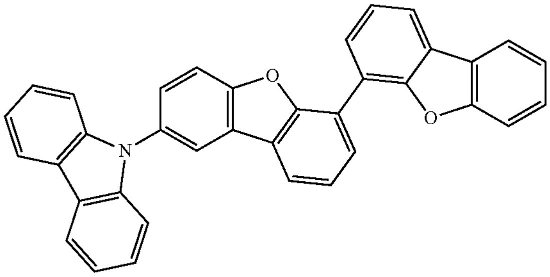

4-5

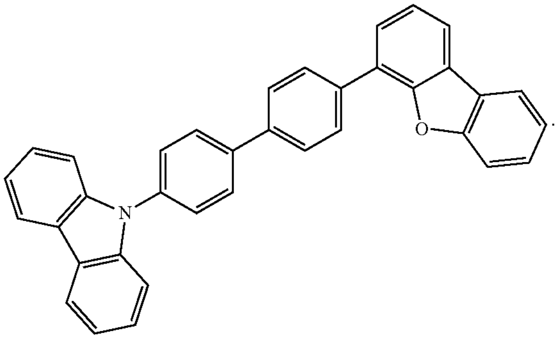

.

In an exemplary aspect, when the EML 240 includes the first to fourth compounds DF1, DF2, FD and H, the contents of the fourth compound H in the EML 240 can be larger than the contents of the first and/or second compounds DF1 and DF2 in the EML 240, and the contents of each of the first and second compounds DF1 and DF2 in the EML 240 can be larger than the contents of the third compound FD in the EML 240. When the contents of the first and second compounds DF1 and DF2 is larger than the contents of the third compound FD, exciton energy can be effectively transferred from the first and second compounds DF1 and DF2 to the third compound FD via FRET mechanism. For example, the contents of the fourth compound H in the EML 240 can be about 45 wt % to about 60 wt %, for example, about 45 wt % to about 55 wt %, the contents of each of the first and second compounds DF1 and DF2 in the EML 240 can be about 10 wt % to about 40 wt %, and the contents of the third compound FD in the EML 240 can be about 0.1 wt % to about 5 wt %, for example, about 0.1 wt % to about 2 wt %, but is not limited thereto.

In one exemplary aspect, HOMO energy levels and/or LUMO energy levels among the fourth compound H of the host, the first and second compounds DF1 and DF2 of the delayed fluorescent material and the third compound FD of the fluorescent material must be properly adjusted. For example, the host must induce the triplet excitons generated at the delayed fluorescent material to be involved in the luminescence process without quenching as non-radiative recombination in order to implement hyper fluorescence. To this end, the energy levels among the fourth compound H of the host, the first and second compounds DF1 and DF2 of the delayed fluorescent material and the third compound FD of the fluorescent material should be adjusted.

Figure 4:
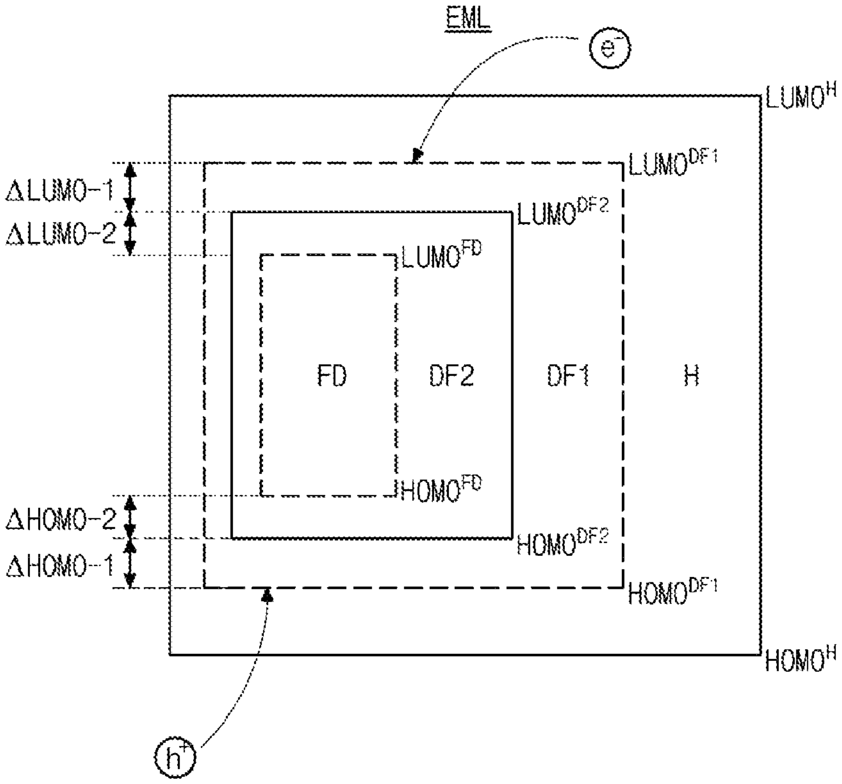
FIG. 4 is a schematic diagram illustrating a state in which excitons are transferred to efficiently to a third compound by adjusting HOMO and LUMO energy levels among first to fourth compounds of luminous materials in an EML in accordance with an exemplary aspect of the present disclosure.

FIG. 4 is a schematic diagram illustrating a state in which excitons are transferred to efficiently to a third compound by adjusting HOMO and LUMO energy levels among first to fourth compounds of luminous materials in an EML in accordance with an exemplary aspect of the present disclosure. As illustrated in FIG. 4, the HOMO energy level HOMO$^{H}$ of the fourth compound H of the host can be lower than the HOMO energy level HOMO$^{DF1}$ of the first compound DF1 of the first delayed fluorescent material, and the LUMO energy level LUMO$^{H}$ of the fourth compound H can be higher than the LUMO energy level LUMO$^{DF1}$ of the first compound DF1. In other words, the energy level bandgap between the HOMO energy level HOMO$^{H}$ and the LUMO energy level LUMO$^{H}$ of the fourth compound H can be wider than the energy level bandgap between the HOMO energy level HOMO$^{DF1}$ and the LUMO energy level LUMO$^{DF1}$ of the first compound DF1.

As an example, an energy level bandgap ($|HOMO^{H}-HOMO^{DF1}|$) between the HOMO energy level (HOMO$^{H}$) of the fourth compound H and the HOMO energy level (HOMO$^{DF1}$) of the first compound DF1, or an energy level bandgap ($|LUMO^{H}-LUMO^{DF}|$) between the LUMO energy level (LUMO$^{H}$) of the fourth compound H and the LUMO energy level (LUMO$^{DF1}$) of the first compound DF1 can be equal to or less than about 0.5 eV, for example, between about 0.1 eV to about 0.5 eV. In this case, the charges can be transported efficiently from the fourth compound H to the first compound DF1 and thereby enhancing the ultimate luminous efficiency in the OLED D1.

The HOMO energy level HOMO$^{DF1}$ of the first compound DF1 can be identical to or lower than the HOMO energy level HOMO$^{DF2}$ of the second compound DF2. The HOMO energy level HOMO$^{DF2}$ of the second compound DF2 can be identical to or lower than the HOMO energy level $HOMO^{FD}$ of the third compound FD. As an example, an energy level bandgap ΔHOMO-1 between the HOMO energy level $HOMO^{DF1}$ of the first compound DF1 and the HOMO energy level $HOMO^{DF2}$ of the second compound DF2 can satisfy the following relationship in Equation (1), and an energy level bandgap ΔHOMO-2 between the HOMO energy level $HOMO^{DF2}$ of the second compound DF2 and the HOMO energy level $HOMO^{FD}$ of the third compound FD can satisfy the following relationship in Equation (2):

$$-0.3\text{ eV} \le HOMO^{DF1} - HOMO^{DF2} \le 0\text{ eV}; \quad (1)$$

$$-0.4\text{ eV} \le HOMO^{DF2} - HOMO^{FD} \le 0\text{ eV}. \quad (2)$$

In another exemplary aspect, the LUMO energy level $LUMO^{DF1}$ of the first compound DF1 can be identical to or higher than the LUMO energy level $LUMO^{DF2}$ of the second compound DF2. The LUMO energy level $LUMO^{DF2}$ of the second compound DF2 can be identical to or lower than the LUMO energy level $LUMO^{FD}$ of the third compound FD. As an example, an energy level bandgap ΔLUMO-1 between the LUOMO energy level $LUMO^{DF1}$ of the first compound DF1 and the LUMO energy level $LUMO^{DF2}$ of the second compound DF2 can satisfy the following relationship in Equation (3), and an energy level bandgap ΔLUMO-2 between the LUMO energy level $LUMO^{DF2}$ of the second compound DF2 and the LUMO energy level $LUMO^{FD}$ of the third compound FD can satisfy the following relationship in Equation (4):

$$0\text{ eV} \le LUMO^{DF1} - LUMO^{DF2} \le 0.3\text{ eV}; \quad (3)$$

$$0\text{ eV} \le LUMO^{DF2} - LUMO^{FD} \le 0.3\text{ eV}. \quad (4)$$

For example, the HOMO energy levels $HOMO^{DF1}$, $HOMO^{DF2}$ and $HOMO^{FD}$ of the first to third compounds DF1, DF2 and FD satisfy the relationship in Equation (1) and (2) and/or the LUMO energy levels $LUMO^{DF1}$, $LUMO^{DF2}$ and $LUMO^{FD}$ of the first to third compounds DF1, DF2 and FD satisfy the relationship in Equation (3) and (4), holes and electrons injected into the EML 240 can be transferred to the first compound DF1 having excellent luminous efficiency. Accordingly, the first compound DF1, which utilizes both initial singlet exciton energy and another singlet exciton energy transferred from its triplet exciton energy by RISC, can implement 100% internal quantum efficiency. The singlet exciton generated at the first compound DF1 can be finally transferred efficiently to the third compound FD via the second compound DF2.

On the other hand, when the HOMO energy level $HOMO^{DF1}$ of the first compound DF1 is higher than the HOMO energy level $HOMO^{DF2}$ of the second compound, and/or the HOMO energy level $HOMO^{DF2}$ of the second compound DF2 is higher than the HOMO energy level $HOMO^{FD}$ of the third compound, holes injected into the EML 240 are trapped in the second compound DF2 and/or the third compound FD, not the first compound DF1. In addition, when the LUMO energy level $LUMO^{DF1}$ of the first compound DF1 is lower than the LUMO energy level $LUMO^{DF2}$ of the second compound, and/or the LUMO energy level $LUMO^{DF2}$ of the second compound DF2 is lower than the LUMO energy level $LUMO^{FD}$ of the third compound, electrons injected into the EML 240 are trapped in the second compound DF2 and/or the third compound FD, not the first compound DF1. The holes and electrons trapped in the third compound FD, which can utilizes only the singlet excitons, are recombined directly in the third compound FD with forming excitons and emitting light. In this case, the triplet exciton energies do not contribute the ultimate light emission with quenching so that the luminous efficiency in the EML 240 is deteriorated.

In addition, the holes trapped in the second compound DF2 and the electrons trapped in the third compound FD, or the holes trapped in the third compound FD and the electrons trapped in the second compound DF2 can form an exciplex. In this case, since the triplet exciton energies are quenching, the luminous efficiency in the EML 240 can be reduced. In addition, as the energy bandgap between the LUMO energy level and the HOMO energy level forming the exciplex becomes too narrow, light of longer wavelength is emitted. As the second compound DF2 and the third compound FD emit light simultaneously, the FWHM of the emitted light becomes wider, and therefore, the color purity of the emitted light becomes deteriorated.

An energy level bandgap between the HOMO energy level $HOMO^{DF1}$ and the LUMO energy level $LUMO^{DF1}$ of the first compound DF1 can be wider than an energy level bandgap between the HOMO energy level $HOMO^{DF2}$ and the LUMO energy level $LUMO^{DF2}$ of the second compound DF2. The energy level bandgap between the HOMO energy level $HOMO^{DF2}$ and the LUMO energy level $LUMO^{DF2}$ of the second compound DF2 can be wider than an energy level bandgap between the HOMO energy level $HOMO^{FD}$ and the LUMO energy level $LUMO^{FD}$ of the third compound FD. In this case, the exciton energies generated in the first compound DF1 can be transferred to the third compound FD via the second compound DF2 so that the OLED D1 in which the third compound FD emits ultimately can enhance its luminous efficiency and luminous lifespan with great.

Now, we will describe the luminous mechanism in the EML 240. FIG. 5 is a schematic diagram illustrating luminous mechanism by singlet and triplet energy levels among luminous materials in an EML in accordance with one exemplary aspect of the present disclosure. As schematically illustrated in FIG. 5, the singlet energy level $S_1^H$ of the fourth compound H, which can be the host in the EML 240, is higher than the singlet energy level $S_1^{DF1}$ of the first compound DF having the delayed fluorescent property. In addition, the triplet energy level $T_1^H$ of the fourth compound H can be higher than the triplet energy level $T_1^{DF1}$ of the first compound DF1. As an example, the triplet energy level $T_1^H$ of the fourth compound H can be higher than the triplet energy level $T_1^{DF1}$ of the first compound DF1 by at least about 0.2 eV, for example, at least about 0.3 eV such as at least about 0.5 eV.

When the triplet energy level $T_1^H$ and/or the singlet energy level $S_1^H$ of the fourth compound H is not high enough than the triplet energy level $T_1^{DF1}$ and/or the singlet energy level $S_1^{DF1}$ of the first compound DF1, the excitons at the triplet energy level $T_1^{DF1}$ of the first compound DF1 can be reversely transferred to the triplet energy level $T_1^H$ of the fourth compound H. In this case, the triplet exciton reversely transferred to the fourth compound H where the triplet exciton cannot be emitted is quenched as non-emission so that the triplet exciton energy of the first compound DF1 having the delayed fluorescent property cannot contribute to luminescence.

As an example, each of the first and second compounds DF1 and DF2 having the delayed fluorescent property can have the energy level bandgap $\Delta E_{ST}^{DF1}$ or $\Delta E_{ST}^{DF1}$ between the singlet energy level $S_1^{DF1}$ or $S_1^{DF2}$ and the triplet energy level $T_1^{DF1}$ or $T_1^{DF2}$ equal to or less than about 0.3 eV, for example between about 0.05 eV and about 0.3 eV.

In addition, the singlet exciton energy, which is generated at the first compound DF1 of the first delayed fluorescent material for example converted to ICT complex by RISC in the EML 240, should be efficiently transferred to the third compound FD of the fluorescent material via the second compound DF2 of the second delayed fluorescent material so as to implement OLED D1 having high luminous efficiency and high color purity.

To this end, the singlet energy level $S_1^{DF1}$ of the first compound DF1 is higher than the singlet energy level $S_1^{DF2}$ of the second compound DF. Optionally, the triplet energy level $T_1^{DF1}$ of the first compound DF1 can be higher than the triplet energy level $T_1^{DF2}$ of the second compound DF2. Also, the singlet energy level $S_1^{DF2}$ of the second compound DF2 of the second delayed fluorescent material is higher than the singlet energy level $S_1^{FD}$ of the third compound FD of the fluorescent material. Optionally, the triplet energy level $T_1^{DF2}$ of the second compound DF2 can be higher than the triplet energy level $T_1^{FD}$ of the third compound FD.

Returning to FIG. 3, the HIL 250 is disposed between the first electrode 210 and the HTL 260 and improves an interface property between the inorganic first electrode 210 and the organic HTL 260. In one exemplary aspect, the HIL 250 can include, but is not limited to, 4,4'4"-Tris(3-methylphenylamino)triphenylamine (MTDATA), 4,4',4"-Tris(N,N-diphenyl-amino)triphenylamine (NATA), 4,4',4"-Tris(N-(naphthalene-1-yl)-N-phenyl-amino)triphenylamine (1T-NATA), 4,4',4"-Tris(N-(naphthalene-2-yl)-N-phenyl-amino) triphenylamine (2T-NATA), Copper phthalocyanine (CuPc), Tris(4-carbazoyl-9-yl-phenyl)amine (TCTA), N,N'-Diphenyl-N,N'-bis(1-naphthyl)-1,1'-biphenyl-4,4"-diamine (NPB; NPD), 1,4,5,8,9,11-Hexaazatriphenylenehexacarbonitrile (Dipyrazino[2,3-f: 2'3'-h]quinoxaline-2,3,6,7,10,11-hexacarbonitrile; HAT-CN), 1,3,5-tris[4-(diphenylamino)phenyl] benzene (TDAPB), poly(3,4-ethylenedioxythiphene)polystyrene sulfonate (PEDOT/PSS), N-(biphenyl-4-yl)-9,9-dimethyl-N-(4-(9-phenyl-9H-carbazol-3-yl)phenyl)-9H-fluoren-2-amine and combination thereof. The HIL 250 can be omitted in compliance with a structure of the OLED D1.

The HTL 260 is disposed between the HIL 250 and the EML 240. In one exemplary aspect, the HTL 260 can include, but is not limited to, N,N'-Diphenyl-N,N'-bis(3-methylphenyl)-1,1'-biphenyl-4,4'-diamine (TPD), NPB, 4,4'-bis(carbazol-9-yl)biphenyl (CBP), Poly[N,N'-bis(4-butylphenyl)-N,N'-bis(phenyl)-benzidine] (Poly-TPD), Poly [(9,9-dioctylfluorenyl-2,7-diyl)-co-(4,4'-(N-(4-sec-butylphenyl)diphenylamine))] (TFB), Di-[4-(N,N-di-p-tolyl-amino)-phenyl]cyclohexane (TAPC), 5-Di(9H-carbazol-9-yl)-N,N-diphenylaniline (DCDPA), N-(biphenyl-4-yl)-9,9-dimethyl-N-(4-(9-phenyl-9H-carbazol-3-yl)phenyl)-9H-fluoren-2-amine, N-(biphenyl-4-yl)-N-(4-(9-phenyl-9H-carbazol-3-yl)phenyl)biphenyl-4-amine and combination thereof.

The ETL 270 and the EIL 280 can be laminated sequentially between the EML 240 and the second electrode 230. The ETL 270 includes material having high electron mobility so as to provide electrons stably with the EML 240 by fast electron transportation. In one exemplary aspect, the ETL 270 can include, but is not limited to, any one of oxadiazole-containing compounds, triazole-containing compounds, phenanthroline-containing compounds, benzoxazole-containing compounds, benzothiazole-containing compounds, benzimidazole-containing compounds, triazine-containing compounds, and the like.

As an example, the ETL 270 can include, but is not limited to, tris-(8-hydroxyquinoline aluminum ($Alq_3$), 2-biphenyl-4-yl-5-(4-t-butylphenyl)-1,3,4-oxadiazole (PBD), spiro-PBD, lithium quinolate (Liq), 1,3,5-Tris(N-phenylbenzimidazol-2-yl)benzene (TPBi), Bis(2-methyl-8-quinolinolato-N1,O8)-(1,1'-biphenyl-4-olato)aluminum (BAlq), 4,7-diphenyl-1,10-phenanthroline (Bphen), 2,9-Bis(naphthalene-2-yl)4,7-diphenyl-1,10-phenanthroline (NBphen), 2,9-Dimethyl-4,7-diphenyl-1,10-phenaathroline (BCP), 3-(4-Biphenyl)-4-phenyl-5-tert-butylphenyl-1,2,4-triazole (TAZ), 4-(Naphthalen-1-yl)-3,5-diphenyl-4H-1,2,4-triazole (NTAZ), 1,3,5-Tri(p-pyrid-3-yl-phenyl)benzene (TpPyPB), 2,4,6-Tris(3'-(pyridin-3-yl)biphenyl-3-yl)1,3,5-triazine (TmPPPyTz), Poly[9,9-bis(3'-(N,N-dimethyl)-N-ethylammonium)-propyl)-2,7-fluorene]-alt-2,7-(9,9-dioctylfluorene)] (PFNBr), tris(phenylquinoxaline) (TPQ), diphenyl[4-(triphenylsilyl)phenyl]phosphine oxide (TSPO1) and combination thereof.

The EIL 280 is disposed between the second electrode 230 and the ETL 270, and can improve physical properties of the second electrode 230 and therefore, can enhance the luminous lifespan of the OLED D1. In one exemplary aspect, the EIL 280 can include, but is not limited to, an alkali metal halide or an alkaline earth metal halide such as LiF, CsF, NaF, $BaF_2$ and the like, and/or an organic metal compound such as lithium quinolate, lithium benzoate, sodium stearate, and the like.

When holes are transferred to the second electrode 230 via the EML 240 and/or electrons are transferred to the first electrode 210 via the EML 240, the OLED D1 can have short lifespan and reduced luminous efficiency. In order to prevent these phenomena, the OLED D1 in accordance with this aspect of the present disclosure can have at least one exciton blocking layer adjacent to the EML 240.

For example, the OLED D1 of the exemplary aspect includes the EBL 265 between the HTL 260 and the EML 240 so as to control and prevent electron transfers. In one exemplary aspect, the EBL 265 can comprise, but is not limited to, TCTA, Tris[4-(diethylamino)phenyl]amine, N-(biphenyl-4-yl)-9,9-dimethyl-N-(4-(9-phenyl-9H-carbazol yl)phenyl)-9H-fluorene-2-amine, TAPC, MTDATA, mCP, mCBP, CuPc, N,N'-bis[4-(bis(3-methylphenyl)amino) phenyl]-N,N'-diphenyl-[1,1'-biphenyl]-4,4'-diamine (DNTPD), TDAPB, 3,6-bis(N-carbazolyl)-N-phenyl-carbazole and combination thereof.

In addition, the OLED D1 can further include the HBL 275 as a second exciton blocking layer between the EML 240 and the ETL 270 so that holes cannot be transferred from the EML 240 to the ETL 270. In one exemplary aspect, the HBL 275 can comprise, but is not limited to, any one of oxadiazole-containing compounds, triazole-containing compounds, phenanthroline-containing compounds, benzoxazole-containing compounds, benzothiazole-containing compounds, benzimidazole-containing compounds, and triazine-containing compounds each of which can be used in the ETL 270.

For example, the HBL 275 can include a compound having a relatively low HOMO energy level compared to the HOMO energy level of the luminescent materials in EML 240. The HBL 275 can include, but is not limited to, BCP, BAlq, $Alq_3$, PBD, spiro-PBD, Liq, Bis-4,5-(3,5-di-3-pyridylphenyl)-2-methylpyrimidine (B3PYMPM), bis[2-(diphenylphosphino)phenyl] ether oxide (DPEPO), 9-(6-(9H-carbazol-9-yl)pyridine-3-yl)-9H-3,9'-bicarbazole and combination thereof.

In the above aspect, the first and second compounds DF1 and DF2 having the delayed fluorescent property and the third compound FD having the fluorescent property are included within the same EML. Unlike that aspect, the first compound and the second compound are included in separate EMLs.

Figure 6:
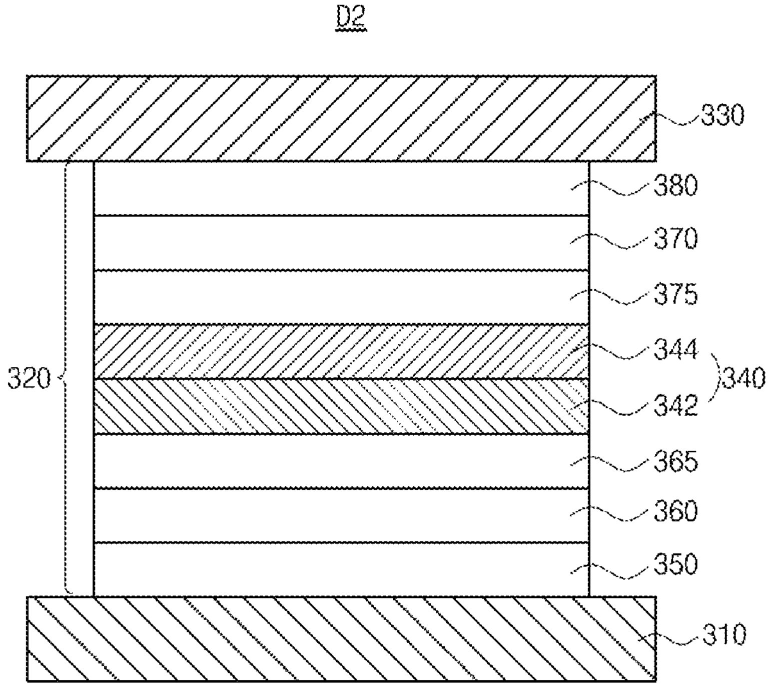
FIG. 6 is a schematic cross-sectional view illustrating an OLED in accordance with another exemplary aspect of the present disclosure.
Figure 7:
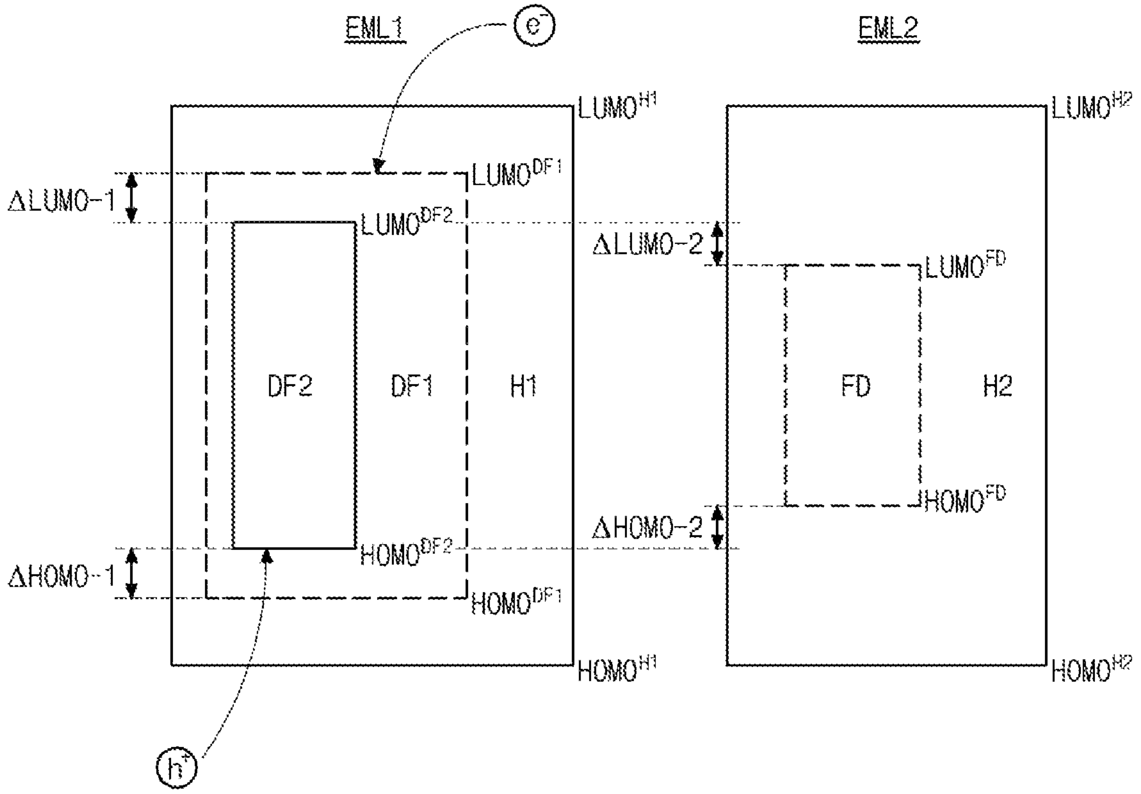
FIG. 7 is a schematic diagram illustrating a state in which excitons are transferred to efficiently to a third compound by adjusting HOMO and LUMO energy levels among first to fifth compounds of luminous materials in an EML in accordance with an another exemplary aspect of the present disclosure.
Figure 8:
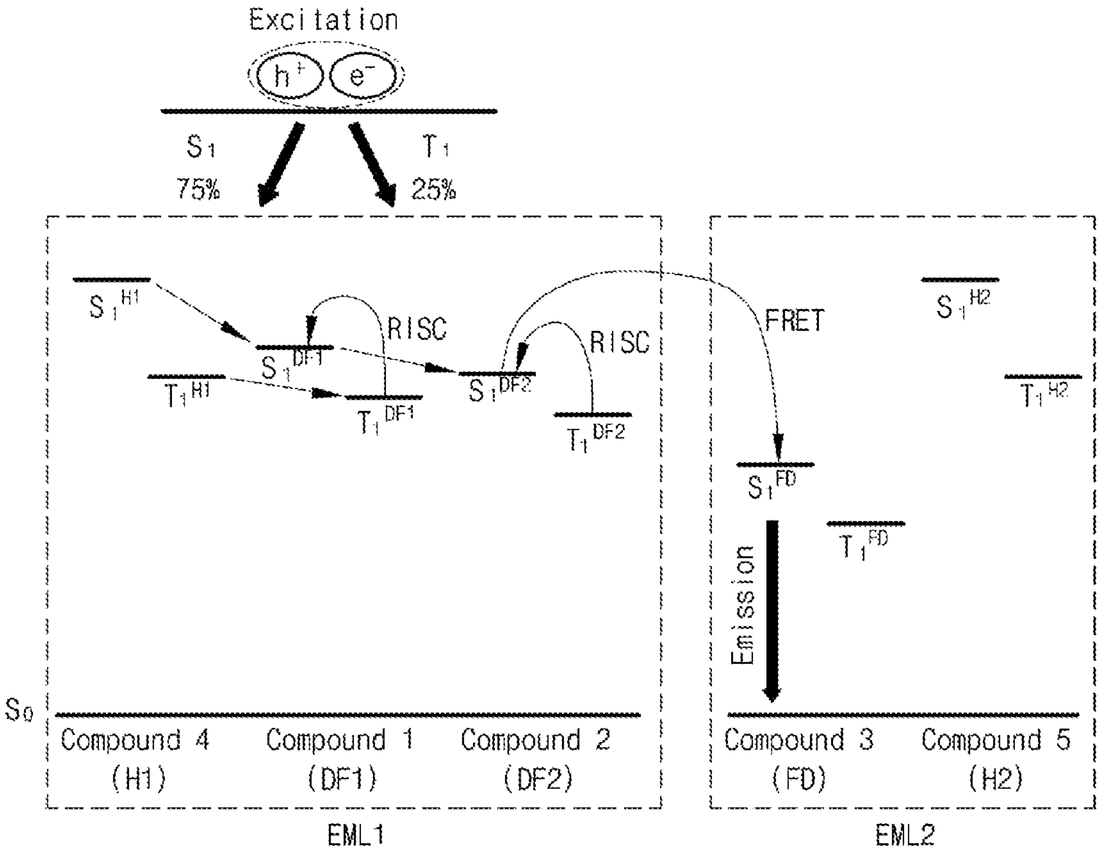
FIG. 8 is a schematic diagram illustrating luminous mechanism by singlet and triplet energy levels among luminous materials in EMLs in accordance with another exemplary aspect of the present disclosure.

FIG. 6 is a schematic cross-sectional view illustrating an OLED in accordance with another exemplary aspect of the present disclosure. FIG. 7 is a schematic diagram illustrating a state in which excitons are transferred to efficiently to a third compound by adjusting HOMO and LUMO energy levels among first to fifth compounds of luminous materials in an EML in accordance with an another exemplary aspect of the present disclosure. FIG. 8 is a schematic diagram illustrating luminous mechanism by singlet and triplet energy levels among luminous materials in EMLs in accordance with another exemplary aspect of the present disclosure.

As illustrated in FIG. 6, the OLED D2 includes first and second electrodes 310 and 330 facing each other and an emissive layer 320 having single emitting part disposed between the first and second electrodes 310 and 330. The organic light emitting display device 100 (FIG. 2) includes a red pixel region, a green pixel region and a blue pixel region, and the OLED D2 can be disposed in the red pixel region.

In one exemplary aspect, the emissive layer 320 includes an EML 340. Also, the emissive layer 320 can include at least one of an HTL 360 disposed between the first electrode 310 and the EML 340 and an ETL 370 disposed between the second electrode 330 and the EML 340. Also, the emissive layer 320 can further comprise at least one of an HIL 350 disposed between the first electrode 310 and the HTL 360 and an EIL 380 disposed between the second electrode 330 and the ETL 370. Alternatively, the emissive layer 320 can further comprise an EBL 365 disposed between the HTL 360 and the EML 340 and/or an HBL 375 disposed between the EML 340 and the ETL 370. The configuration of the first and second electrodes 310 and 330 as well as other layers except the EML 340 in the emissive layer 320 can be substantially identical to the corresponding electrodes and layers in the OLED D1.

The EML 340 includes a first EML (EML1, lower EML, first layer) 342 disposed between the EBL 365 and the HBL 375 and a second EML (EML2, upper EML, second layer) 344 disposed between the EML1 342 and the HBL 375. Alternatively, the EML2 344 can be disposed between the EBL 365 and the EML1 342.

One of the EML1 342 and the EML2 344 includes the first and second compounds (first and second dopants) DF1 and DF2 of the delayed fluorescent material, and the other of the EML1 342 and the EML2 344 includes the third compound (third dopant) FD of the fluorescent material. Also, each of the EML1 342 and the EML2 344 includes a fourth compound (Compound 4) H1 of a first host and a fifth compound (Compound 5) H2 of a second host, respectively. As an example, the EML1 342 can include the first and second compounds DF1 and DF2 and the EML2 344 can include the third compound FD.

The first compound DF1 in the EML1 242 can include delayed fluorescent material having the structure of Formulae 1 to 2. The second compound DF2 can include delayed fluorescent material having the structure of Formulae 3 to 4. The triplet exciton energy of each of the first and second compounds DF1 and DF2 having delayed fluorescent property can be converted upwardly to its own singlet exciton energy via RISC mechanism. While each of the first and second compounds DF1 and DF2 has high internal quantum efficiency, but it has poor color purity due to its wide FWHM.

The EML2 344 includes the third compound FD of the florescent material. The third compound FD can include the BODIPY-based organic compound having the structure of Formulae 5 to 6. The third compound FD of the fluorescent material having the structure of Formulae 5 to 6 has relatively narrow FWHM (e.g. equal to or less than about 35 nm) compared to the FWHM of the first and second compounds DF1 and DF2. While the third compound FD has an advantage in terms of color purity, but its quantum efficiency is limited since its triplet exciton cannot be involved in participate in the luminescence process.

However, in this exemplary aspect, the singlet exciton energy as well as the triplet exciton energy of the first and second compounds DF1 and DF2 having the delayed fluorescent property in the EML1 342 can be transferred to the third compound FD in the EML2 344 disposed adjacently to the EML1 342 by FRET mechanism, and the ultimate light emission occurs in the third compound FD within the EML2 344.

In other words, the triplet exciton energy of the first compound DF1 is converted upwardly to its own singlet exciton energy in the EML1 342 by RISC mechanism. Then, both the initial singlet exciton energy and the converted singlet exciton energy of the first compound DF1 is transferred to the singlet exciton energy of the third compound FD in the EML2 344 through the second compound DF2. The third compound FD in the EML2 344 can emit light using the triplet exciton energy as well as the singlet exciton energy.

As the singlet exciton energies generated at the first and second compounds DF1 and DF2 included in the EML1 342 is efficiently transferred to the third compound FD in the EML2 244, the OLED D2 can implement hyper fluorescence. In this case, while the first and second compounds DF1 and DF2 having the delayed fluorescent property only act as transferring exciton energy to the third compound FD, substantial light emission is occurred in the EML2 344 including the third compound FD. The OLED D2 can enhance its luminous efficiency as well as its color purity owing to narrow FWHM.

The fourth compound H1 can be identical to or different from the fifth compound H2. For example, each of the fourth compound H1 and the fifth compound H2 can include, but is not limited to, the organic compound having the structure of Formulae 7 to 8.

Similar to the first aspect, the HOMO energy level $HOMO^{DF1}$ of the first compound DF1 can be identical to or lower than the HOMO energy level $HOMO^{DF2}$ of the second compound DF2. The HOMO energy level $HOMO^{DF2}$ of the second compound DF2 can be identical to or lower than the HOMO energy level $HOMO^{FD}$ of the third compound FD. Alternatively, the LUMO energy level $LUMO^{DF1}$ of the first compound DF1 can be identical to or higher than the LUMO energy level $LUMO^{DF2}$ of the second compound DF2. The LUMO energy level $LUMO^{DF2}$ of the second compound DF2 can be identical to or higher than the LUMO energy level $HOMO^{FD}$ of the third compound FD.

As an example, the energy bandgap ΔHOMO-1 between the HOMO energy level $HOMO^{DF1}$ of the first compound and the HOMO energy level $HOMO^{DF2}$ of the second compound DF2 can satisfy the relationship in Equation (1), and/or the energy level bandgap ΔHOMO-2 between the HOMO energy level $HOMO^{DF2}$ of the second compound DF2 and the HOMO energy level $HOMO^{FD}$ of the third compound FD can satisfy the relationship in Equation (2). Alternatively, the energy level bandgap ΔLUMO-1 between the LUOMO energy level $LUMO^{DF1}$ of the first compound DF1 and the LUMO energy level $LUMO^{DF2}$ of the second compound DF2 can satisfy the relationship in Equation (3), and/or the energy level bandgap ΔLUMO-2 between the LUMO energy level $LUMO^{DF2}$ of the second compound DF2 and the LUMO energy level $LUMO^{FD}$ of the third compound FD can satisfy the relationship in Equation (4). Accordingly, holes and electrons injected into the EML 340 are transferred to the first compound DF1, and then, the first compound DF1 utilizing both the singlet and triplet exciton energies can transfer exciton energies to the third compound FD via the second compound DF2.

Also, an energy level bandgap ($|HOMO^{H}-HOMO^{DF1}|$) between the HOMO energy levels ($HOMO^{H1}$ and $HOMO^{H2}$) of the fourth and fifth compounds H1 and H2 and the HOMO energy level ($HOMO^{DF1}$) of the first compound DF1, or an energy level bandgap ($|LUMO^{H}-LUMO^{DF1}|$) between the LUMO energy levels ($LUMO^{H1}$ and $LUMO^{H2}$) of the fourth and fifth compounds H1 and H2 and the LUMO energy level ($LUMO^{DF1}$) of the first compound DF1 can be equal to or less than about 0.5 eV.

Also, each of the exciton energies generated in each of the fourth compound H1 in the EML1 342 and the fifth compound H2 in the EML2 344 should be transferred primarily to the first compound DF1 of the first delayed florescent material and then to the third compound FD of the fluorescent material in order to realize efficient light emission. As illustrated in FIG. 8, each of the singlet energy levels $S_1^{H1}$ and $S_1^{H2}$ of the fourth and fifth compounds H1 and H2 is higher than the singlet energy level $S_1^{DF1}$ of the first compound DF1. In addition, each of the triplet energy levels $T_1^{H1}$ and $T_1^{H2}$ of the fourth and fifth compounds H1 and H2 can be higher than the triplet energy level $T_1^{DF1}$ of the first compound DF1. For example, the triplet energy levels $T_1^{H1}$ and $T_1^{H2}$ of the fourth and fifth compound H1 and H2 can be higher than the triplet energy level $T_1^{DF1}$ of the first compound DF1 by at least about 0.2 eV, for example, by at least 0.3 eV such as by at least 0.5 eV.

Also, the singlet energy level $S_1^{H2}$ of the fifth compound H2 of the second host is higher than the singlet energy level $S_1^{FD}$ of the third compound FD of the fluorescent material. Optionally, the triplet energy level $T_1^{H2}$ of the fifth compound H2 can be higher than the triplet energy level $T_1^{FD}$ of the third compound FD. In this case, the singlet exciton energy generated at the fifth compound H2 can be transferred to the singlet energy of the third compound FD.

In addition, the exciton energy, which is generated at the first compound DF1 having the delayed fluorescent property for example converted to ICT complex by RISC in the EML1 342, should be efficiently transferred to the third compound FD of the fluorescent material in the EML2 344. To this end, the singlet energy level $S_1^{DF1}$ and/or the triplet energy level $T_1^{DF1}$ of the first compound DF1 in the EML1 342 is higher than the singlet energy level $S_1^{DF2}$ and/or the triplet energy level $T_1^{DF2}$. In addition, the singlet energy level $S_1^{DF2}$ of the second compound DF2 is higher than the singlet energy level $S_1^{FD}$ of the third compound FD in the EML2 344. Optionally, the triplet energy level $T_1^{DF2}$ of the second compound DF2 can be higher than the triplet energy level $T_1^{FD}$ of the third compound FD.

Each of the contents of the fourth and fifth compounds H1 and H2 in the EML1 342 and the EML2 344 can be larger than or identical to each of the contents of the first and second compounds DF1 and DF2 and the third compound FD in the same layer, respectively. Also, each of the contents of the first and second compounds DF1 and DF2 in the EML1 342 can be larger than the contents of the third compound FD in the EML2 344. In this case, exciton energy is efficiently transferred from the first and second compound DF1 and DF2 in the EML1 342 to the third compound FD in the EML2 344 via FRET mechanism.

As an example, the EML1 342 can include each of the first and second compounds DF1 and DF2 between about 10 wt % and about 40 wt %. The EML2 344 can include the third compound FD between about 1 wt % and about 10 wt %, for example, about 1 wt % and 5 wt %.

In one exemplary aspect, when the EML2 344 is disposed adjacently to the HBL 375, the fifth compound H2 in the EML2 344 can be the same material as the HBL 375. In this case, the EML2 344 can have a hole blocking function as well as an emission function. In other words, the EML2 344 can act as a buffer layer for blocking holes. In one aspect, the HBL 375 can be omitted where the EML2 344 can be a hole blocking layer as well as an emitting material layer.

In another exemplary aspect, when the EML2 344 is disposed adjacently to the EBL 365, the fifth compound H2 in the EML2 344 can be the same as the EBL 365. In this case, the EML2 344 can have an electron blocking function as well as an emission function. In other words, the EML2 344 can act as a buffer layer for blocking electrons. In one aspect, the EBL 365 can be omitted where the EML2 344 can be an electron blocking layer as well as an emitting material layer.

Figure 9:
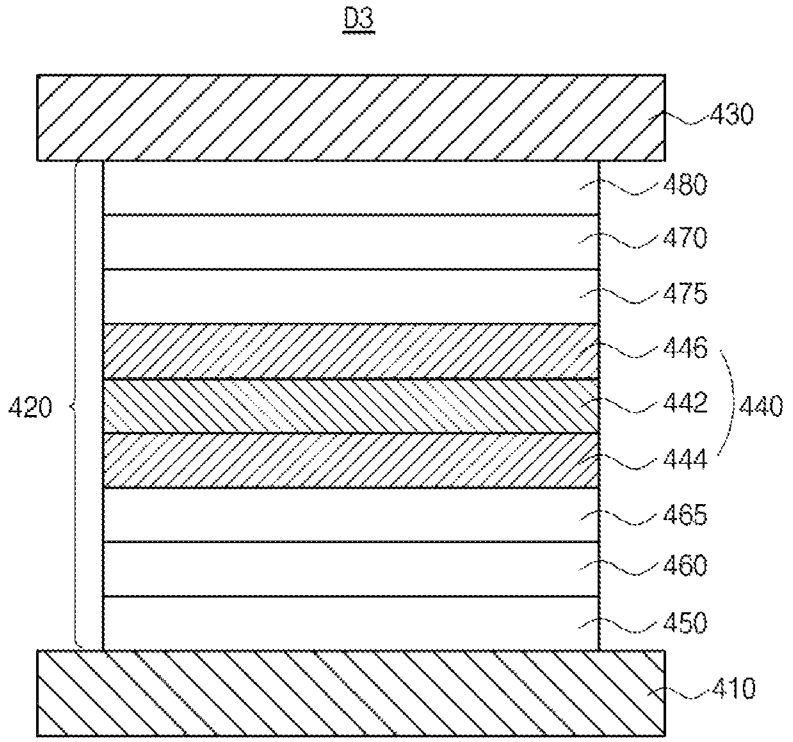
FIG. 9 is a schematic cross-sectional view illustrating an OLED in accordance with still another exemplary aspect of the present disclosure.
Figure 10:
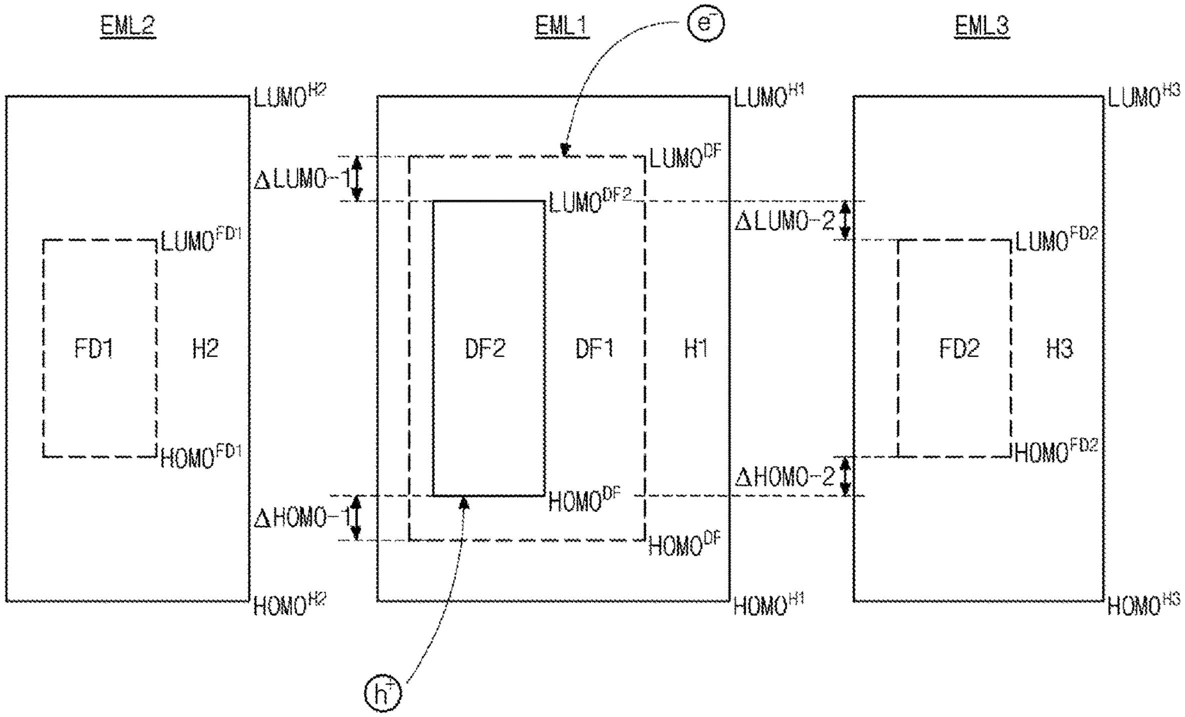
FIG. 10 is a schematic diagram illustrating a state in which excitons are transferred to efficiently to third and sixth compounds by adjusting HOMO and LUMO energy levels among first to seventh compounds of luminous materials in an EML in accordance with still another exemplary aspect of the present disclosure.
Figure 11:
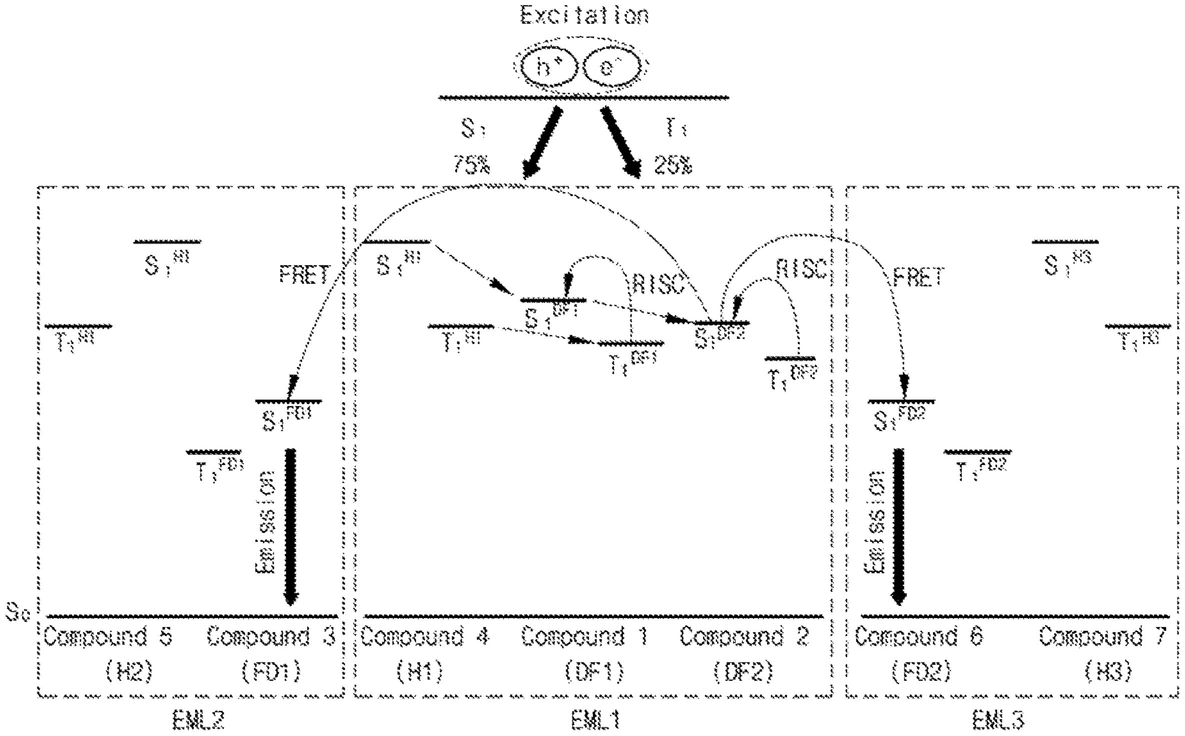
FIG. 11 is a schematic diagram illustrating luminous mechanism by singlet and triplet energy levels among luminous materials in EMLs in accordance with still another exemplary aspect of the present disclosure.

An OLED having a triple-layered EML will be explained. FIG. 9 is a schematic cross-sectional view illustrating an OLED in accordance with still another exemplary aspect of the present disclosure. FIG. 10 is a schematic diagram illustrating a state in which excitons are transferred to efficiently to third and sixth compounds by adjusting HOMO and LUMO energy levels among first to seventh compounds of luminous materials in an EML in accordance with still another exemplary aspect of the present disclosure. FIG. 11 is a schematic diagram illustrating luminous mechanism by singlet and triplet energy levels among luminous materials in EMLs in accordance with still another exemplary aspect of the present disclosure.

As illustrated in FIG. 9, the OLED D3 includes first and second electrodes 410 and 430 facing each other and an emissive layer 420 disposed between the first and second electrodes 410 and 430. The organic light emitting display device 100 (FIG. 2) includes a red pixel region, a green pixel region and a blue pixel region, and the OLED D3 can be disposed in the red pixel region.

In one exemplary aspect, the emissive layer 420 having single emitting part includes a triple-layered EML 440. The emissive layer 420 can include at least one of an HTL 460 disposed between the first electrode 410 and the EML 440 and an ETL 470 disposed between the second electrode 430 and the EML 440. Also, the emissive layer 420 can further include at least one of an HIL 450 disposed between the first electrode 410 and the HTL 460 and an EIL 480 disposed between the second electrode 430 and the ETL 470. Alternatively, the emissive layer 420 can further include an EBL 465 disposed between the HTL 460 and the EML 440 and/or an HBL 475 disposed between the EML 440 and the ETL 470. The configurations of the first and second electrodes 410 and 430 as well as other layers except the EML 440 in the emissive layer 420 is substantially identical to the corresponding electrodes and layers in the OLEDs D1 and D2.

The EML 440 includes a first EML (EML1, middle EML, first layer) 442, a second EML (EML2, lower EML, second layer) 444 and a third EML (EML3, upper EML, third layer) 446. The EML1 442 is disposed between the EBL 465 and the HBL 475, the EML2 444 is disposed between the EBL 465 and the EML1 442 and the EML3 446 is disposed between the EML1 442 and the HBL 475.

The EML1 442 includes the first and second compounds (first and second dopants) DF1 and DF2 of the delayed fluorescent material. Each of the EML2 444 and the EML3 446 includes the third compound (third dopant) FD1 and a sixth compound (Compound 6, fourth dopant) FD2 each of which is the fluorescent material, respectively. Also, each of the EML1 442, the EML2 444 and the EML3 446 includes the fourth compound H1 of the first host, the fifth compound H2 of the second host and a seventh compound (Compound 7) H3 of a third host, respectively.

In accordance with this aspect, both the singlet energy as well as the triplet energy of the first and second compounds DF1 and DF2 of the delayed fluorescent material in the EML1 442 can be transferred to the third and sixth compounds FD1 and FD2 of the fluorescent materials each of which is included in the EML2 444 and EML3 446 disposed adjacently to the EML1 442 by FRET energy transfer mechanism. Accordingly, the ultimate emission occurs in the third and sixth compounds FD1 and FD2 in the EML2 444 and the EML3 446.

In other words, the triplet exciton energy of the first compound DF1 having the delayed fluorescent property in the EML1 442 is converted upwardly to its own singlet exciton energy by RISC mechanism, then the singlet exciton energy including the initial and converted singlet exciton energy of the first and second compounds DF1 and DF2 included in the EML1 442 is transferred to the singlet exciton energy of the third and sixth compounds FD1 and FD2 in the EML2 444 and the EML3 446 because each of the first and second compounds DF1 and DF2 has the singlet energy level $S_1^{DF1}$ or $S_1^{DF2}$ higher than each of the singlet energy levels $S_1^{FD1}$ and $S_1^{FD2}$ of the second and fifth compounds FD1 and FD2 (FIG. 11).

Both the third and sixth compounds FD1 and FD2 included in the EML2 444 and EML3 446 can emit light using the singlet exciton energy as well as the triplet exciton energy transferred from the first and second compounds DF1 and DF2. Each of the third and sixth compounds FD1 and FD2 has relatively narrow FWHM (e.g. equal to or less than about 35 nm) compared to the FWHM of the first and second compounds DF1 and DF2. In this aspect, the OLED D3 can improve its quantum efficiency as well as its color purity due to narrow FWHM. The ultimate emission occurs in the EML2 444 and the EML3 446 each of which includes the third compound FD1 and the sixth compound FD2, respectively.

The first compound DF1 includes the organic compound having the structure of Formulae 1 to 2, and the second compound DF2 includes the organic compound having the structure of Formulae 3 to 4. Each of the third and sixth compounds FD1 and FD2 of the fluorescent material includes independently the organic compound having the structure of Formulae 5 to 6. The fourth compound H1, the fifth compound H2 and the seventh compound H3 can be identical to or different from each other. For example, each of the fourth compound H1, the fifth compound H2 and the seventh compound H3 can independently include, but is not limited to, the organic compound having the structure of Formulae 7 to 8, respectively.

Similar to the first and second aspects, the HOMO energy level $HOMO^{DF1}$ of the first compound DF1 can be identical to or lower than the HOMO energy level $HOMO^{DF2}$ of the second compound DF2. The HOMO energy level $HOMO^{DF2}$ of the second compound DF2 can be identical to or lower than the HOMO energy levels $HOMO^{FD1}$ and $HOMO^{FD2}$ of the third and sixth compounds FD1 and FD2. Alternatively, the LUMO energy level $LUMO^{DF1}$ of the first compound DF1 can be identical to or higher than the LUMO energy level $LUMO^{DF2}$ of the second compound DF2. The LUMO energy level $LUMO^{DF2}$ of the second compound DF2 can be identical to or higher than the LUMO energy level $HOMO^{FD1}$ and $LUMO^{FD2}$ of the third and sixth compounds FD1 and FD2.

As an example, the energy bandgap ΔHOMO-1 between the HOMO energy level $HOMO^{DF1}$ of the first compound and the HOMO energy level $HOMO^{DF2}$ of the second compound DF2 can satisfy the relationship in Equation (1), and/or the energy level bandgap ΔHOMO-2 between the HOMO energy level $HOMO^{DF2}$ of the second compound DF2 and the HOMO energy level $HOMO^{FD1}$ and $HOMO^{FD2}$ of the third and sixth compounds FD1 and FD2 can satisfy the relationship in Equation (2). Alternatively, the energy level bandgap ΔLUMO-1 between the LUOMO energy level $LUMO^{DF1}$ of the first compound DF1 and the LUMO energy level $LUMO^{DF2}$ of the second compound DF2 can satisfy the relationship in Equation (3), and/or the energy level bandgap ΔLUMO-2 between the LUMO energy level $LUMO^{DF2}$ of the second compound DF2 and the LUMO energy level $LUMO^{FD1}$ and $LUMO^{FD2}$ of the third and sixth compounds FD1 and FD2 can satisfy the relationship in Equation (4).

Also, an energy level bandgap ($|HOMO^{H}-HOMO^{DF1}|$) between the HOMO energy levels ($HOMO^{H1}$, $HOMO^{H2}$ and $HOMO^{H3}$) of the fourth, fifth and seventh compounds H1, H2 and H3 and the HOMO energy level ($HOMO^{DF1}$) of the first compound DF1, or an energy level bandgap ($|LUMO^{H}-LUMO^{DF}|$) between the LUMO energy levels ($LUMO^{H1}$, $LUMO^{H2}$ and $LUMO^{H3}$) of the fourth, fifth and seventh compounds H1, H2 and H3 and the LUMO energy level (LUMO') of the first compound DF1 can be equal to or less than about 0.5 eV.

The singlet and triplet energy levels among the luminous materials should be properly adjusted in order to implement efficient luminescence. Referring to FIG. 11, each of the singlet energy levels $S_1^{H1}$, $S_1^{H2}$ and $S_1^{H3}$ of the fourth fifth and seventh compounds H1, H2 and H3 of the first to third hosts is higher than the singlet energy level $S_1^{DF1}$ of the first compound DF1. Also, each of the triplet energy levels $T_1^{H1}$, $T_1^{H2}$ and $T_1^{H}$ of the fourth, fifth and seventh compounds H1, H2 and H3 can be higher than the triplet energy level $T_1^{DF1}$ of the first compound DF1.

In addition, the singlet exciton energy, which is generated at the first compound DF1 having the delayed fluorescent property for example converted to ICT complex by RISC in the EML1 442, should be efficiently transferred to each of third and sixth compounds FD1 and FD2 of the fluorescent material in the EML2 444 and the EML3 446 via the second compound DF2. To this end, the singlet energy level $S_1^{DF1}$ and/or the triplet energy level $T_1^{DF1}$ of the first compound DF1 in the EML1 442 is higher than the singlet energy level $S_1^{DF2}$ and/or the triplet energy level $T_1^{DF2}$ of the second compound DF2. In addition, the singlet energy level $S_1^{DF2}$ of the second compound DF2 is higher than the singlet energy levels $S_1^{FD1}$ and $S_1^{FD2}$ of the third and sixth compounds FD1 and FD2 in the EML2 444 and the EML 446. Optionally, the triplet energy level $T_1^{DF2}$ of the second compound DF2 can be higher than the triplet energy levels $T_1^{FD1}$ and $T_1^{FD2}$ of the third and sixth compounds FD1 and FD2.

In addition, exciton energy transferred to each of the third and sixth compounds FD1 and FD2 from the first and second compounds DF1 and DF2 should not be transferred to each of the fifth and seventh compounds H2 and H3 in order to realize efficient luminescence. To this end, each of the singlet energy levels $S_1^{H2}$ and $S_1^{H3}$ of the fifth and seventh compounds H2 and H3, each of which can be the second host and the third host, is higher than each of the singlet energy levels $S_1^{FD1}$ and $S_1^{FD2}$ of the third and sixth compounds FD1 and FD2 of the fluorescent material, respectively. Optionally, each of the triplet energy levels $T_1^{H2}$ and $T_1^{H3}$ of the fifth and seventh compounds H2 and H3 is higher than each of the triplet energy levels $T_1^{FD1}$ and $T_1^{FD2}$ of the third and sixth compounds FD1 and FD2, respectively.

The contents of the first and second compounds DF1 and DF2 in the EML1 442 can be larger than each of the contents of the third and sixth compounds FD1 and FD2 in the EML2 444 or the EML3 446. In this case, exciton energy can be transferred sufficiently from the first and second compounds DF1 and DF2 in the EML1 442 to each of the second and fifth compounds FD1 and FD2 in the EML2 444 and the EML3 446 via FRET mechanism. As an example, the EML1 442 can include the first and second compounds DF1 and DF2 between about 1 wt % and about 50 wt %, for example, about 10 wt % and about 40 wt %. Each of the EML2 444 and the EML3 446 can include the third and sixth compound FD1 and FD2 between about 1 wt % and about 10 wt %, for example, about 1 wt % and 5 wt %.

In one exemplary aspect, when the EML2 444 is disposed adjacently to the EBL 465, the fifth compound H2 in the EML2 444 can be the same material as the EBL 465. In this case, the EML2 444 can have an electron blocking function as well as an emission function. In other words, the EML2 444 can act as a buffer layer for blocking electrons. In one aspect, the EBL 465 can be omitted where the EML2 444 can be an electron blocking layer as well as an emitting material layer.

When the EML3 446 is disposed adjacently to the HBL 475, the seventh compound H3 in the EML3 446 can be the same material as the HBL 475. In this case, the EML3 446 can have a hole blocking function as well as an emission function. In other words, the EML3 446 can act as a buffer layer for blocking holes. In one aspect, the HBL 475 can be omitted where the EML3 446 can be a hole blocking layer as well as an emitting material layer.

In still another exemplary aspect, the fifth compound H2 in the EML2 444 can be the same material as the EBL 465 and the seventh compound H3 in the EML3 446 can be the same material as the HBL 475. In this aspect, the EML2 444 can have an electron blocking function as well as an emission function, and the EML3 446 can have a hole blocking function as well as an emission function. In other words, each of the EML2 444 and the EML3 446 can act as a buffer layer for blocking electrons or hole, respectively. In one aspect, the EBL 465 and the HBL 475 can be omitted where the EML2 444 can be an electron blocking layer as well as an emitting material layer and the EML3 446 can be a hole blocking layer as well as an emitting material layer.

Figure 12:
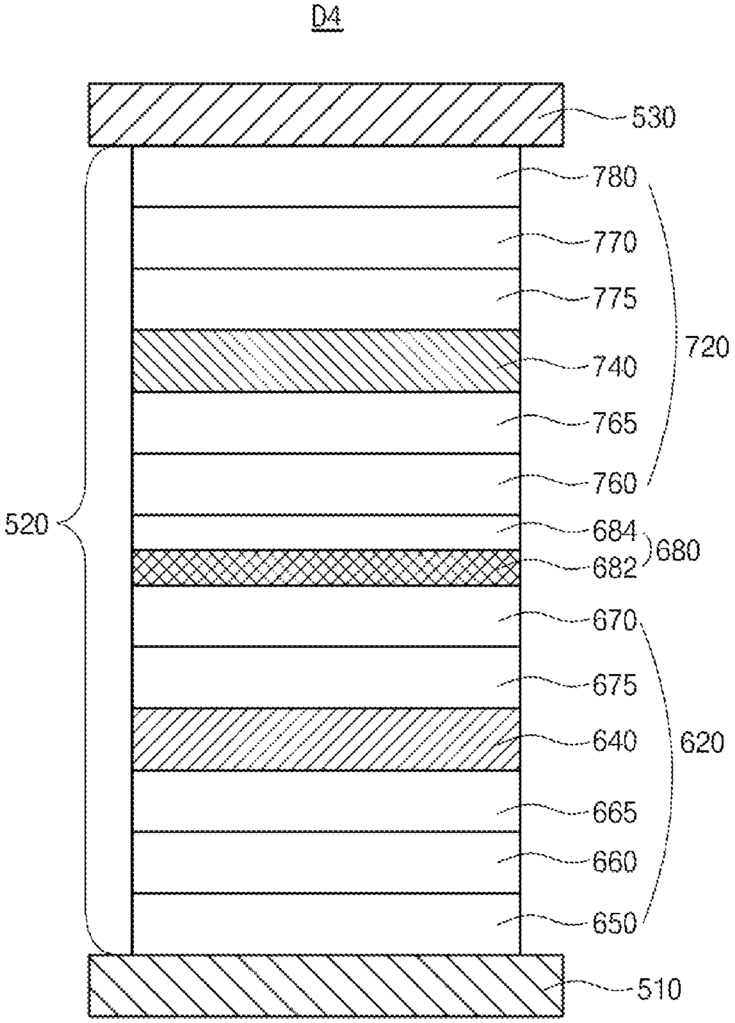
FIG. 12 is a schematic cross-sectional view illustrating an OLED in accordance with still another exemplary aspect of the present disclosure.

In an alternative aspect, an OLED can include multiple emitting parts. FIG. 12 is a schematic cross-sectional view illustrating an OLED in accordance with still another exemplary aspect of the present disclosure.

As illustrated in FIG. 12, the OLED D4 includes first and second electrodes 510 and 530 facing each other and an emissive layer 520 with two emitting parts disposed between the first and second electrodes 510 and 530. The organic light emitting display device 100 (FIG. 1) includes a red pixel region, a green pixel region and a blue pixel region, and the OLED D4 can be disposed in the red and/or green pixel regions. The first electrode 510 can be an anode and the second electrode 530 can be a cathode.

The emissive layer 520 includes a first emitting part 620 including a first EML (EML1) 640, and a second emitting part 720 including a second EML (EML2) 740. Also, the emissive layer 520 can further include a charge generation layer (CGL) 680 disposed between the first emitting part 620 and the second emitting part 720.

The CGL 680 is disposed between the first and second emitting parts 620 and 720 so that the first emitting part 620, the CGL 680 and the second emitting part 720 are sequentially disposed on the first electrode 510. In other words, the first emitting part 620 is disposed between the first electrode 510 and the CGL 680 and the second emitting part 720 is disposed between the second electrode 530 and the CGL 680.

The first emitting part 620 includes the EML1 640. The first emitting part 620 can further includes at least one of an HIL 650 disposed between the first electrode 510 and the EML1 640, a first HTL (HTL1) 660 disposed between the HIL 650 and the EML1 640 and a first ETL (ETL1) 670 disposed between the EML1 640 and the CGL 680. Alternatively, the first emitting part 620 can further include a first EBL (EBL1) 665 disposed between the HTL1 660 and the EML1 640 and/or a first HBL (HBL1) 675 disposed between the EML1 640 and the ETL1 670.

The second emitting part 720 includes the EML2 740. The second emitting part 720 can further include at least one of a second HTL (HTL2) 760 disposed between the CGL 680 and the EML2 740, a second ETL (ETL2) 770 disposed between the EML2 740 and the second electrode 530 and an EIL 780 disposed between the ETL2 770 and the second electrode 530. Alternatively, the second emitting part 720 can further include a second EBL (EBL2) 765 disposed between the HTL2 760 and the EML2 740 and/or a second HBL (HBL2) 775 disposed between the EML2 740 and the ETL2 770.

The CGL 680 is disposed between the first emitting part 620 and the second emitting part 720. The first emitting part 620 and the second emitting part 720 are connected via the CGL 680. The CGL 680 can be a PN-junction CGL that junctions an N-type CGL (N-CGL) 682 with a P-type CGL (P-CGL) 684.

The N-CGL 682 is disposed between the ETL1 670 and the HTL2 760 and the P-CGL 684 is disposed between the N-CGL 682 and the HTL2 760. The N-CGL 682 transports electrons to the EML1 640 of the first emitting part 620 and the P-CGL 684 transport holes to the EML2 740 of the second emitting part 720.

In this aspect, each of the EML1 640 and the EML2 740 can be a red emitting material layer. For example, at least one of the EML1 640 and the EML2 740 can include the first and second compounds DF1 and DF2 of the delayed fluorescent material, the third compound FD of the fluorescent material, and optionally the fourth compound H of the host.

As an example, when the EML1 640 and/or the EML2 740 includes the first to fourth compounds DF1, DF2, FD and H, the contents of the fourth compound H can be larger than each of the contents of the first and second compounds DF1 and DF2, and each of the contents of the first and second compounds DF1 and DF2 can be larger than the contents of the third compound FD. In this case, exciton energy can be transferred efficiently from the first and second compounds DF1 and DF2 to the third compound FD.

As an example, the contents of the fourth compound H in the EML1 640 and/or the EML2 740 can be between about 45 wt % and about 60 wt %, for example, about 45 wt % and about 55 wt %, each of the content of the first and second compounds DF1 and DF2 in the EML1 640 and/or the EML2 740 can be between about 10 wt % and about 40 wt %, and the contents of the third compound FD in the EML1 640 and/or the EML2 740 can be between about 0.1 wt % and about 5 wt %, for example, about 0.1 wt % and about 2 wt %, but is not limited thereto.

In one exemplary aspect, the EML2 740 can include the first to third compounds DF1, DF2 and FD, and optionally the first compound H as the same as the EML1 640. Alternatively, the EML2 740 can include another compound for example different from at least one of the first to third compounds DF1, DF2 and FD in the EML1 640, and thus the EML2 740 can emit light different from the light emitted from the EML1 640 or can have different luminous efficiency different from the luminous efficiency of the EML1 640.

In FIG. 12, each of the EML1 640 and the EML2 740 has a single-layered structure. Alternatively, each of the EML1 640 and the EML2 740, each of which can include the first to third compounds, can have a double-layered structure (FIG. 6) or a triple-layered structure (FIG. 9), respectively.

In the OLED D4, the singlet exciton energy of the first and second compounds DF1 and DF2 of the delayed fluorescent material is transferred to the third compound FD of fluorescent material, and the ultimate emission is occurred at the third compound FD. Accordingly, the OLED D4 can improve its luminous efficiency and color purity. In addition, the first compound DF1 having the structure of Formulae 1 to 2, the second compound DF2 having the structure of Formulae 3 to 4 and the third compound FD having the structure of Formulae 5 to 6 are included in the at least EML1 640, the luminous efficiency and color purity of the OLED D4 can be further enhanced. Moreover, since the OLED D4 has a double stack structure of a red emitting material layer, the OLE4 D4 can further improve its color sense or optimize its luminous efficiency.

FIG. 13 is a schematic cross-sectional view illustrating an organic light emitting display device in accordance with another exemplary aspect of the present disclosure. As illustrated in FIG. 13, an organic light emitting display device 800 includes a substrate 810 that defines first to third pixel regions P1, P2 and P3, a thin film transistor Tr disposed over the substrate 810 and an OLED D disposed over the thin film transistor Tr and connected to the thin film transistor Tr. As an example, the first pixel region P1 can be a green pixel region, the second pixel region P2 can be a red pixel region and the third pixel region P3 can be a red pixel region.

The substrate 810 can be a glass substrate or a flexible substrate. For example, the flexible substrate can be any one of a PI substrate, a PES substrate, a PEN substrate, a PET substrate and a PC substrate. A buffer layer 812 is disposed over the substrate 810 and the thin film transistor Tr is disposed over the buffer layer 812. The buffer layer 812 can be omitted. As illustrated in FIG. 2, the thin film transistor Tr includes a semiconductor layer, a gate electrode, a source electrode and a drain electrode and acts as a driving element.

A passivation layer 850 is disposed over the thin film transistor Tr. The passivation layer 850 has a flat top surface and includes a drain contact hole 852 that exposes a drain electrode of the thin film transistor Tr.

The OLED D is disposed over the passivation layer 850, and includes a first electrode 910 for example connected to the drain electrode of the thin film transistor Tr, and an emissive layer 920 and a second electrode 930 each of which is disposed sequentially on the first electrode 910. The OLED D is disposed in each of the first to third pixel regions P1, P2 and P3 and emits different light in each pixel region. For example, the OLED D in the first pixel region P1 can emit blue light, the OLED D in the second pixel region P2 can emit green light and the OLED D in the third pixel region P3 can emit red light.

The first electrode 910 is separately formed for each of the first to third pixel regions P1, P2 and P3, and the second electrode 930 corresponds to the first to third pixel regions P1, P2 and P3 and is formed integrally.

The first electrode 910 can be one of an anode and a cathode, and the second electrode 930 can be the other of the anode and the cathode. In addition, one of the first electrode 910 and the second electrode 930 can be a transmissive (or semi-transmissive) electrode and the other of the first electrode 910 and the second electrode 930 can be a reflective electrode.

For example, the first electrode 910 can be an anode and can include conductive material having a relatively high work function value, i.e., a transparent conductive oxide layer of transparent conductive oxide (TCO). The second electrode 930 can be a cathode and can include conductive material having relatively low work function value, i.e., a metal material layer of low-resistant metal. For example, the first electrode 910 can include any one of ITO, IZO, ITZO, SnO, ZnO, ICO and AZO, and the second electrode 930 can include Al, Mg, Ca, Ag, alloy thereof (e.g. Mg—Ag) or combination thereof.

When the organic light emitting display device 800 is a bottom-emission type, the first electrode 910 can have a single-layered structure of a transparent conductive oxide layer. Alternatively, when the organic light emitting display device 900 is a top-emission type, a reflective electrode or a reflective layer can be disposed under the first electrode 910. For example, the reflective electrode or the reflective layer can include, but is not limited to, Ag or APC alloy. In the OLED D of the top-emission type, the first electrode 910 can have a triple-layered structure of ITO/Ag/ITO or ITO/APC/ITO. Also, the second electrode 930 is thin so as to have light-transmissive (or semi-transmissive) property.

A bank layer 860 is disposed on the passivation layer 850 in order to cover edges of the first electrode 910. The bank layer 860 corresponds to each of the first to third pixel regions P1, P2 and P3 and exposes a center of the first electrode 910.

An emissive layer 920 is disposed on the first electrode 910. In one exemplary aspect, the emissive layer 920 can have a single-layered structure of an EML. Alternatively, the emissive layer 920 can include at least one of an HIL, an HTL, and an EBL disposed sequentially between the first electrode 910 and the EML and/or an HBL, an ETL and an EIL disposed sequentially between the EML and the second electrode 930.

In one exemplary aspect, the EML of the emissive layer 930 in the third pixel region P3 of the red pixel region can include the first compound DF1 of the first delayed fluorescent material having the structure of Formulae 1 to 2, the second compound DF2 of the second delayed fluorescent material having the structure of Formulae 3 to 4, the third compound FD of the fluorescent material having the structure of Formula 5 to 6, and optionally the fourth compound H of the host having the structure of Formulae 7 to 8.

An encapsulation film 870 is disposed over the second electrode 930 in order to prevent outer moisture from penetrating into the OLED D. The encapsulation film 970 can have, but is not limited to, a triple-layered structure of a first inorganic insulating film, an organic insulating film and a second inorganic insulating film.

The organic light emitting display device 800 can have a polarizer in order to decrease external light reflection. For example, the polarizer can be a circular polarizer. When the organic light emitting display device 800 is a bottom-emission type, the polarizer can be disposed under the substrate 810. Alternatively, when the organic light emitting display device 800 is a top emission type, the polarizer can be disposed over the encapsulation film 870.

Figure 14:
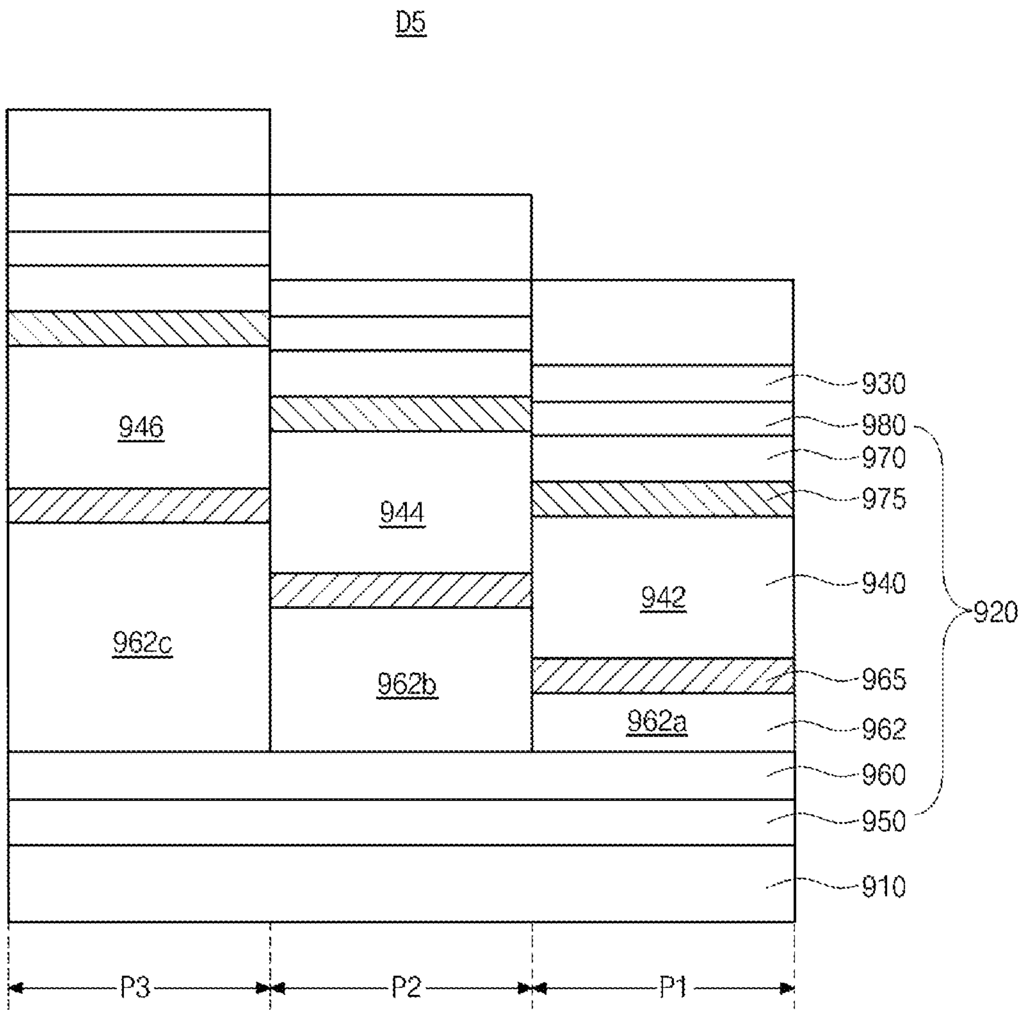
FIG. 14 is a schematic cross-sectional view illustrating an OLED in accordance with still another exemplary aspect of the present disclosure.

FIG. 14 is a schematic cross-sectional view illustrating an OLED in accordance with still another exemplary aspect of the present disclosure. As illustrated in FIG. 14, the OLED D5 includes a first electrode 910, a second electrode 930 facing the first electrode 910 and an emissive layer 920 disposed between the first and second electrodes 910 and 930.

The first electrode 910 can be an anode and the second electrode 930 can be a cathode. As an example, the first electrode 910 can be a reflective electrode and the second electrode 930 can be a transmissive (or semi-transmissive) electrode.

The emissive layer 920 includes an EML 940. The emissive layer 920 can include at least one of an HTL 960 disposed between the first electrode 910 and the EML 940 and an ETL 970 disposed between the EML 940 and the second electrode 930. Also, the emissive layer 920 can further include at least one of an HIL 950 disposed between the first electrode 910 and the HTL 960 and an EIL 980 disposed between the ETL 970 and the second electrode 930. In addition, the emissive layer 920 can further include at least one of an EBL 965 disposed between the HTL 960 and the EML 940 and an HBL 975 disposed between the EML 940 and the ETL 970.

In addition, the emissive layer 920 can further include an auxiliary hole transport layer (auxiliary HTL) 962 disposed between the HTL 960 and the EBL 965. The auxiliary HTL 962 can include a first auxiliary HTL 962*a* located in the first pixel region P1, a second auxiliary HTL 962*b* located in the second pixel region P2 and a third auxiliary HTL 962*c* located in the third pixel region P3.

The first auxiliary HTL 962*a* has a first thickness, the second auxiliary HTL 962*b* has a second thickness and the third auxiliary HTL 962*c* has a third thickness. The first thickness is less than the second thickness and the second thickness is less than the third thickness. Accordingly, the OLED D5 has a micro-cavity structure.

Owing to the first to third auxiliary HTLs 962*a*, 962*b* and 962*c* having different thickness to each other, the distance between the first electrode 910 and the second electrode 930 in the first pixel region P1 emitting light in the first wavelength range (blue light) is smaller than the distance between the first electrode 910 and the second electrode 930 in the second pixel region P2 emitting light in the second wavelength range (green light), which is longer than the first wavelength range. The distance between the first electrode 910 and the second electrode 930 in the second pixel region P2 is smaller than the distance between the first electrode 910 and the second electrode 932 in the third pixel region P3 emitting light in the third wavelength range (red light), which is longer than the second wavelength range. Accordingly, the OLED D5 has improved luminous efficiency.

In FIG. 14, the first auxiliary HTL 962*a* is located in the first pixel region P1. Alternatively, the OLED D5 can implement the micro-cavity structure without the first auxiliary HTL 962*c*. In addition, a capping layer can be disposed over the second electrode 930 in order to improve out-coupling of the light emitted from the OLED D5.

The EML 940 includes a first EML (EML1) 942 located in the first pixel region P1, a second EML (EML2) 944 located in the second pixel region P2 and a third EML (EML3) 946 located in the third pixel region P3. Each of the EML1 942, the EML2 944 and the EML3 946 can be a blue EML, a green EML and a red EML, respectively.

In one exemplary aspect, the EML3 946 in the third pixel region P3 can include the first compound DF1 of the first delayed fluorescent material having the structure of Formulae 1 to 2, the second compound DF2 of the second delayed fluorescent material having the structure of Formulae 3 to 4, the third compound FD of the fluorescent material having the structure of Formulae 5 to 6, and optionally, the fourth compound H of the host. In this case, the EML3 946 can have a single-layered structure, a double-layered structure (FIG. 6) or a triple-layered structure (FIG. 6). In the EML3 946, the contents of the fourth compound H can be larger than each of the first and second compounds DF1 and DF2, and each of the contents of the first and second compounds DF1 and DF2 can be larger than the contents of the third compound FD.

The EML1 942 in the first pixel region P1 can include host and blue dopant. For example, the host in the EML1 942 can include the fourth compound H, and the blue dopant can include at least one of blue phosphorescent material, blue fluorescent material and blue delayed fluorescent material.

The EML2 944 in the second pixel region P2 can include host and green dopant. For example, the host in the EML1 944 can include the fourth compound H, and the green dopant can include at least one of green phosphorescent material, green fluorescent material and green delayed fluorescent material.

The OLED D5 emits blue light, green light and red light in each of the first to third pixel regions P1, P2 and P3 so that the organic light emitting display device 800 (FIG. 13) can implement a full-color image.

The organic light emitting display device 800 can further include a color filter layer corresponding to the first to third pixel regions P1, P2 and P3 for improving color purity of the light emitted from the OLED D. As an example, the color filter layer can comprise a first color filter layer (blue color filter layer) corresponding to the first pixel region P1, the second color filter layer (green color filter layer) corresponding to the second pixel region P2 and the third color filter layer (red color filter layer) corresponding to the third pixel region P3.

When the organic light emitting display device 800 is a bottom-emission type, the color filter layer can be disposed between the OLED D and the substrate 810. Alternatively, when the organic light emitting display device 800 is a top-emission type, the color filter layer can be disposed over the OLED D.

Figure 15:
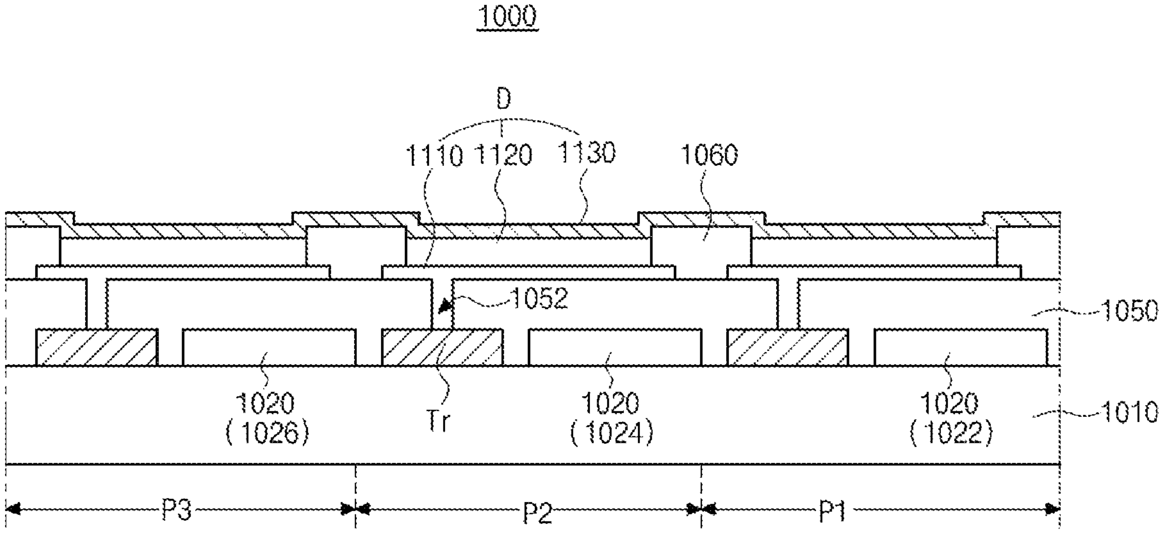
FIG. 15 is a schematic cross-sectional view illustrating an organic light emitting display device in accordance with still another exemplary aspect of the present disclosure.

FIG. 15 is a schematic cross-sectional view illustrating an organic light emitting display device in accordance with still another exemplary aspect of the present disclosure. As illustrated in FIG. 15, the organic light emitting display device 1000 includes a substrate 1010 defining a first pixel region P1, a second pixel region P2 and a third pixel region P3, a thin film transistor Tr disposed over the substrate 1010, an OLED D disposed over the thin film transistor Tr and connected to the thin film transistor Tr and a color filter layer 1020 corresponding to the first to third pixel regions P1, P2 and P3. As an example, the first pixel region P1 can be a blue pixel region, the second pixel region P2 can be a green pixel region and the third pixel region P3 can be a red pixel region.

The substrate 1010 can be a glass substrate or a flexible substrate. For example, the flexible substrate can be any one of a PI substrate, a PES substrate, a PEN substrate, a PET substrate and a PC substrate. The thin film transistor Tr is located over the substrate 1010. Alternatively, a buffer layer can be disposed over the substrate 1010 and the thin film transistor Tr can be disposed over the buffer layer. As illustrated in FIG. 2, the thin film transistor Tr includes a semiconductor layer, a gate electrode, a source electrode and a drain electrode and acts as a driving element.

The color filter layer 1020 is located over the substrate 1010. As an example, the color filter layer 1020 can include a first color filter pattern 1022 corresponding to the first pixel region P1, a second color filter pattern 1024 corresponding to the second pixel region P2 and a third color filter pattern 1026 corresponding to the third pixel region P3. The first color filter pattern 1022 can be a blue color filter pattern, the second color filter pattern 1024 can be a green color filter pattern and the third color filter pattern 1026 can be a red color filter pattern. For example, the first color filter pattern 1022 can include at least one of blue dye or green pigment, the second color filter pattern 1024 can include at least one of green dye or red pigment and the third color filter pattern 1026 can include at least one of red dye or blue pigment.

A passivation layer 1050 is disposed over the thin film transistor Tr and the color filter layer 1020. The passivation layer 1050 has a flat top surface and includes a drain contact hole 1052 that exposes a drain electrode of the thin film transistor Tr.

The OLED D is disposed over the passivation layer 1050 and corresponds to the color filter layer 1020. The OLED D includes a first electrode 1110 for example connected to the drain electrode of the thin film transistor Tr, and an emissive layer 1120 and a second electrode 1130 each of which is disposed sequentially on the first electrode 1110. The OLED D emits white light in the first to third pixel regions P1, P2 and P3.

The first electrode 1110 is separately formed for each of the first to third pixel regions P1, P2 and P3, and the second electrode 1130 corresponds to the first to third pixel regions P1, P2 and P3 and is formed integrally. The first electrode 1110 can be one of an anode and a cathode, and the second electrode 1130 can be the other of the anode and the cathode. In addition, the first electrode 1110 can be a transmissive (or semi-transmissive) electrode and the second electrode 1130 can be a reflective electrode.

For example, the first electrode 1110 can be an anode and can include conductive material having a relatively high work function value, i.e., a transparent conductive oxide layer of transparent conductive oxide (TCO). The second electrode 1130 can be a cathode and can include conductive material having relatively low work function value, i.e., a metal material layer of low-resistant metal. For example, the transparent conductive oxide layer of the first electrode 1110 can include any one of ITO, IZO, ITZO, SnO, ZnO, ICO and AZO, and the second electrode 1130 can include Al, Mg, Ca, Ag, alloy thereof (e.g., Mg—Ag) or combination thereof.

The emissive layer 1120 is disposed on the first electrode 1110. The emissive layer 1120 includes at least two emitting parts emitting different colors. Each of the emitting part can have a single-layered structure of an EML. Alternatively, each of the emitting parts can include at least one of an HIL, an HTL, an EBL, an HBL, an ETL and an EIL. In addition, the emissive layer 1120 can further comprise a CGL disposed between the emitting parts.

At least one of the at least two emitting parts can include the first compound DF1 of the first delayed fluorescent material having the structure of Formulae 1 to 2, the second compound DF2 of the second delayed fluorescent material having the structure of Formulae 3 to 4, the third compound FD of the BODIPY-based fluorescent material having the structure of Formulae 5 to 6, and optionally the fourth compound H of the host having the structure of Formulae 7 to 8.

A bank layer 1060 is disposed on passivation layer 1050 in order to cover edges of the first electrode 1110. The bank layer 1060 corresponds to each of the first to third pixel regions P1, P2 and P3 and exposes a center of the first electrode 1110. As described above, since the OLED D emits white light in the first to third pixel regions P1, P2 and P3, the emissive layer 1120 can be formed as a common layer without being separated in the first to third pixel regions P1, P2 and P3. The bank layer 1060 is formed to prevent current leakage from the edges of the first electrode 1110, and the bank layer 1060 can be omitted.

Moreover, the organic light emitting display device 1000 can further include an encapsulation film disposed on the second electrode 1130 in order to prevent outer moisture from penetrating into the OLED D. In addition, the organic light emitting display device 1000 can further comprise a polarizer disposed under the substrate 1010 in order to decrease external light reflection.

In the organic light emitting display device 1000 in FIG. 15, the first electrode 1110 is a transmissive electrode, the second electrode 1130 is a reflective electrode, and the color filter layer 1020 is disposed between the substrate 1010 and the OLED D. For example, the organic light emitting display device 1000 is a bottom-emission type. Alternatively, the first electrode 1110 can be a reflective electrode, the second electrode 1120 can be a transmissive electrode (or semi-transmissive electrode) and the color filter layer 1020 can be disposed over the OLED D in the organic light emitting display device 1000.

In the organic light emitting display device 1000, the OLED D located in the first to third pixel regions P1, P2 and P3 emits white light, and the white light passes through each of the first to third pixel regions P1, P2 and P3 so that each of a blue color, a green color and a red color is displayed in the first to third pixel regions P1, P2 and P3, respectively.

A color conversion film can be disposed between the OLED D and the color filter layer 1020. The color conversion film corresponds to the first to third pixel regions P1, P2 and P3, and includes a blue color conversion film, a green color conversion film and a red color conversion film each of which can convert the white light emitted from the OLED D into blue light, green light and red light, respectively. For example, the color conversion film can include quantum dots. Accordingly, the organic light emitting display device 1000 can further enhance its color purity. Alternatively, the color conversion film can displace the color filter layer 1020.

Figure 16:
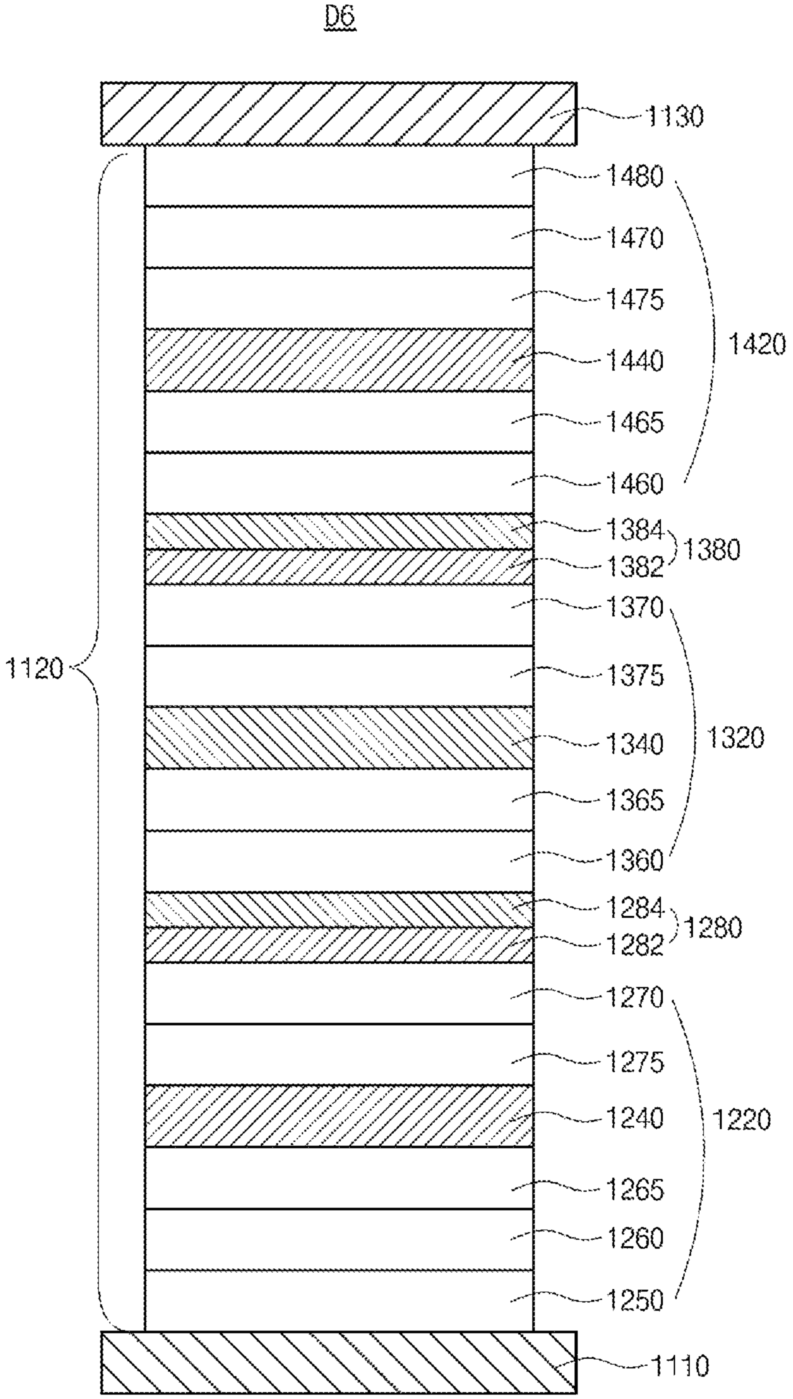
FIG. 16 is a schematic cross-sectional view illustrating an organic light emitting display device in accordance with still another exemplary aspect of the present disclosure.

FIG. 16 is a schematic cross-sectional view illustrating an OLED in accordance with still another exemplary aspect of the present disclosure. As illustrated in FIG. 16, the OLED D6 includes first and second electrodes 1110 and 1130 facing each other and an emissive layer 1120 disposed between the first and second electrodes 1110 and 1130. The first electrode 1110 can be an anode and the second electrode 1130 can be a cathode. For example, the first electrode 1100 can be a transmissive electrode and the second electrode 1130 can be a reflective electrode.

The emissive layer 1120 includes a first emitting part 1220 including a first EML (lower EML, EML1) 1240, a second emitting part 1320 comprising a second EML (middle EML, EML2) 1340 and a third emitting part 1420 comprising a third EML (upper EML, EML3) 1440. In addition, the emissive layer 1120 can further includes a first charge generation layer (CGL1) 1280 disposed between the first emitting part 1220 and the second emitting part 1320 and a second charge generation layer (CGL2) 1380 disposed between the second emitting part 1320 and the third emitting part 1420. Accordingly, the first emitting part 1220, the CGL1 1280, the second emitting part 1320, the CGL2 1380 and the third emitting part 1420 are disposed sequentially on the first electrode 1110.

The first emitting part 1220 can further include at least one of an HIL 1250 disposed between the first electrode 1110 and the EML1 1240, a first HTL (HTL1) 1260 disposed between the EML1 1240 and the HIL 1250 and a first ETL (ETL1) 1270 disposed between the EML1 1240 and the CGL1 1280. Alternatively, the first emitting part 1220 can further include at least one of a first EBL (EBL1) 1265 disposed between the HTL1 1260 and the EML1 1240 and a first HBL (HBL1) 1275 disposed between the EML1 1240 and the ETL1 1270.

The second emitting part 1320 can further include at least one of a second HTL (HTL2) 1360 disposed between the CGL1 1280 and the EML2 1340, a second ETL (ETL2) 1370 disposed between the EML2 1340 and the CGL2 1380. Alternatively, the second emitting part 1320 can further include a second EBL (EBL2) 1365 disposed between the HTL2 1360 and the EML2 1340 and/or a second HBL (HBL2) 1375 disposed between the EML2 1340 and the ETL2 1370.

The third emitting part 1420 can further include at least one of a third HTL (HTL3) 1460 disposed between the CGL2 1380 and the EML3 1440, a third ETL (ETL3) 1470 disposed between the EML3 1440 and the second electrode 1130 and an EIL 1480 disposed between the ETL3 1470 and the second electrode 1130. Alternatively, the third emitting part 1420 can further comprise a third EBL (EBL3) 1465 disposed between the HTL3 1460 and the EML3 1440 and/or a third HBL (HBL3) 1475 disposed between the EML3 1440 and the ETL3 1470.

The CGL1 1280 is disposed between the first emitting part 1220 and the second emitting part 1320. For example, the first emitting part 1220 and the second emitting part 1320 are connected via the CGL1 1280. The CGL1 1280 can be a PN-junction CGL that junctions a first N-type CGL (N-CGL1) 1282 with a first P-type CGL (P-CGL1) 1284.

The N-CGL1 1282 is disposed between the ETL1 1270 and the HTL2 1360 and the P-CGL1 1284 is disposed between the N-CGL1 1282 and the HTL2 1360. The N-CGL1 1282 transports electrons to the EML1 1240 of the first emitting part 1220 and the P-CGL1 1284 transport holes to the EML2 1340 of the second emitting part 1320.

The CGL2 1380 is disposed between the second emitting part 1320 and the third emitting part 1420. For example, the second emitting part 1320 and the third emitting part 1420 are connected via the CGL2 1380. The CGL2 1380 can be a PN-junction CGL that junctions a second N-type CGL (N-CGL2) 1382 with a second P-type CGL (P-CGL2) 1384.

The N-CGL2 1382 is disposed between the ETL2 1370 and the HTL3 1460 and the P-CGL2 1384 is disposed between the N-CGL2 1382 and the HTL3 1460. The N-CGL2 1382 transports electrons to the EML2 1340 of the second emitting part 1320 and the P-CGL2 1384 transport holes to the EML3 1440 of the third emitting part 1420.

In this aspect, one of the first to third EMLs 1240, 1340 and 1440 can be a blue EML, another of the first to third EMLs 1240, 1340 and 1440 can be a green EML and the third of the first to third EMLs 1240, 1340 and 1440 can be a red EML.

As an example, the EML1 1240 can be a blue EML, the EML2 1340 can be a green EML and the EML3 1440 can be a red EML. Alternatively, the EML1 1240 can be a red EML, the EML2 1340 can be a green EML and the EML3 1440 can be a blue EML. Hereinafter, the OLED D3 where the EML1 1240 is a blue EML, the EML2 1340 is a green EML and the EML3 is a red EML will be described.

The EML1 1240 can include a host and a blue dopant. For example, the host in the EML1 1240 can include the fourth compound H, and the blue dopant can include at least one of the blue phosphorescent material, the blue fluorescent material and the blue delayed fluorescent material.

The EML2 1340 can include a host and a green dopant. For example, the host in the EML2 1340 can include the fourth compound H, and the green dopant can include at least one of the green phosphorescent material, the green fluorescent material and the green delayed fluorescent material.

The EML3 1440 can include the first compound DF1 of the first delayed fluorescent material having the structure of Formulae 1 to 2, the second compound DF2 of the second delayed fluorescent material having the structure of Formulae 3 to 4, the third compound FD of the BODIPY-based fluorescent material having the structure of Formulae 5 to 6, and optionally, the fourth compound H of the host. The EML3 1440 including the first to fourth compounds DF1, DF2, FD and H can have a single-layered structure, a double-layered structure (FIG. 6) or a triple-layered structure (FIG. 9). In the EML3 1440, the contents of the fourth compound H can be larger than each of the contents of the first and second compounds DF1 and DF2, and each of the contents of the first and second compound DF1 and DF2 can be larger than the contents of the third compound FD.

The OLED D6 emits white light in each of the first to third pixel regions P1, P2 and P3 and the white light passes though the color filter layer 1020 (FIG. 15) correspondingly disposed in the first to third pixel regions P1, P2 and P3. Accordingly, the organic light emitting display device 1000 (FIG. 15) can implement a full-color image.

Figure 17:
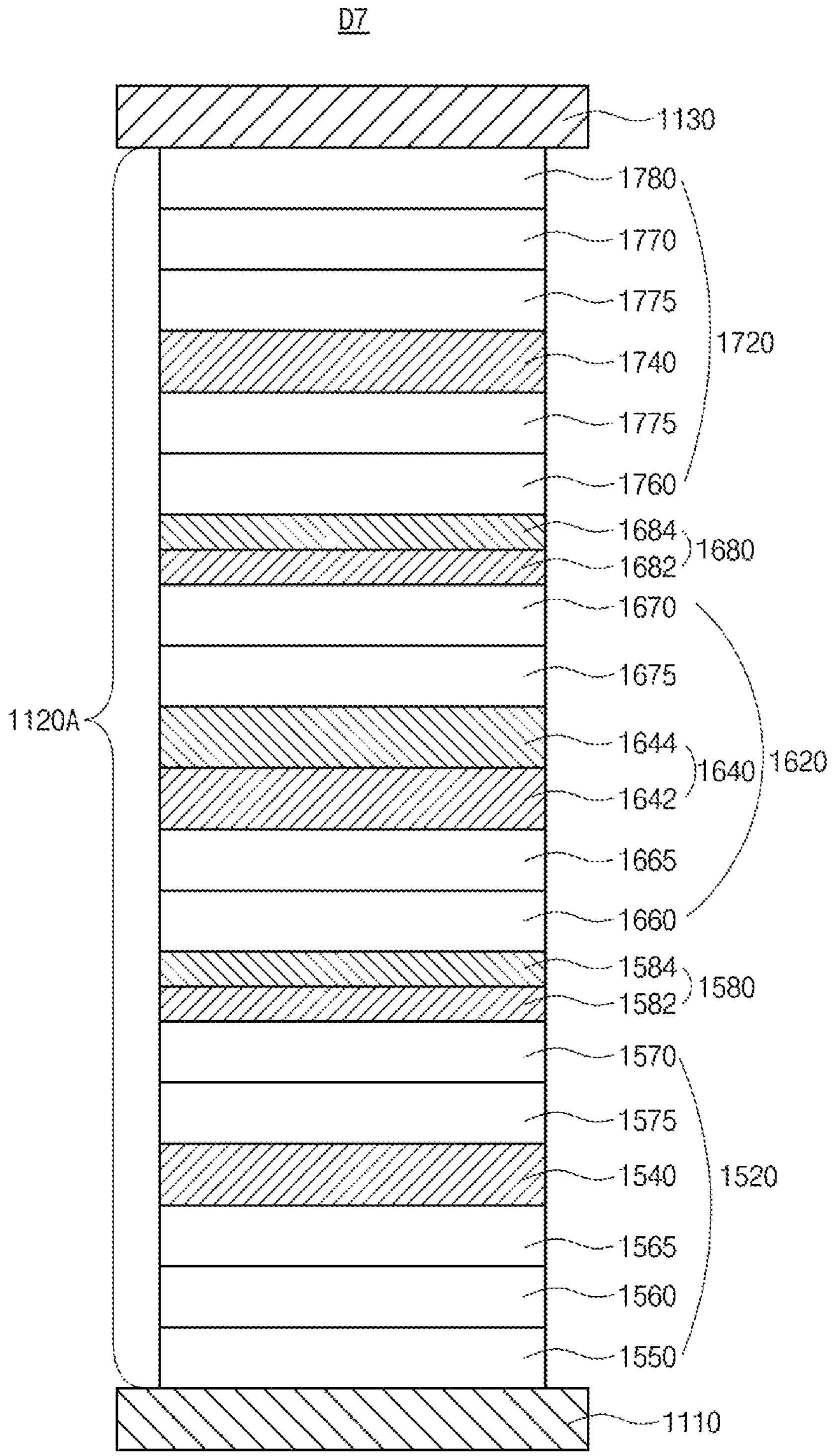
FIG. 17 is a schematic cross-sectional view illustrating an OLED in accordance with still another exemplary aspect of the present disclosure.

FIG. 17 is a schematic cross-sectional view illustrating an OLED in accordance with still another exemplary aspect of the present disclosure. As illustrated in FIG. 17, the OLED D7 includes first and second electrodes 1110 and 1130 facing each other and an emissive layer 1120A disposed between the first and second electrodes 1110 and 1130. The first electrode 1110 can be an anode and the second electrode 1130 can be a cathode. For example, the first electrode 1100 can be a transmissive electrode and the second electrode 1130 can be a reflective electrode.

The emissive layer 1120A includes a first emitting part 1520 comprising an EML1 (lower EML) 1540, a second emitting part 1620 comprising an EML2 (middle EML) 1640 and a third emitting part 1720 comprising an EML3 (upper EML) 1740. In addition, the emissive layer 1120A can further include a CGL1 1580 disposed between the first emitting part 1520 and the second emitting part 1620 and a CGL2 1680 disposed between the second emitting part 1620 and the third emitting part 1720. Accordingly, the first emitting part 1520, the CGL1 1580, the second emitting part 1620, the CGL2 1680 and the third emitting part 1720 are disposed sequentially on the first electrode 1110.

The first emitting part 1520 can further include at least one of an HIL 1550 disposed between the first electrode 1110 and the EML1 1540, an HTL1 1560 disposed between the EML1 1540 and the HIL 1550 and an ETL1 1570 disposed between the EML1 1540 and the CGL1 1580. Alternatively, the first emitting part 1520 can further comprise an EBL1 1565 disposed between the HTL1 1560 and the EML1 1540 and/or an HBL1 1575 disposed between the EML1 1540 and the ETL1 1570.

The EML2 1640 of the second emitting part 1620 includes a middle lower EML (first layer) 1642 and a middle upper EML (second layer) 1644. The middle lower EML 1642 is located adjacently to the first electrode 1110 and the upper middle EML 1644 is located adjacently to the second electrode 1130. In addition, the second emitting part 1620 can further include at least one of an HTL2 1660 disposed between the CGL1 1580 and the EML2 1640, an ETL2 1670 disposed between the EML2 1640 and the CGL2 1680. Alternatively, the second emitting part 1620 can further comprise at least one of an EBL2 1665 disposed between the HTL2 1660 and the EML2 1640 and an HBL2 1675 disposed between the EML2 1640 and the ETL2 1670.

The third emitting part 1720 can further include at least one of an HTL3 1760 disposed between the CGL2 1680 and the EML3 1740, an ETL3 1770 disposed between the EML3 1740 and the second electrode 1130 and an EIL 1780 disposed between the ETL3 1770 and the second electrode 1130. Alternatively, the third emitting part 1720 can further include an EBL3 1765 disposed between the HTL3 1760 and the EML3 1740 and/or an HBL3 1775 disposed between the EML3 1740 and the ETL3 1770.

The CGL1 1580 is disposed between the first emitting part 1520 and the second emitting part 1620. For example, the first emitting part 1520 and the second emitting part 1620 are connected via the CGL1 1580. The CGL1 1580 can be a PN-junction CGL that junctions an N-CGL1 1582 with a P-CGL1 1584. The N-CGL1 1582 is disposed between the ETL1 1570 and the HTL2 1660 and the P-CGL1 1584 is disposed between the N-CGL1 1582 and the HTL2 1560.

The CGL2 1680 is disposed between the second emitting part 1620 and the third emitting part 1720. For example, the second emitting part 1620 and the third emitting part 1720 are connected via the CGL2 1680. The CGL2 1680 can be a PN-junction CGL that junctions an N-CGL2 1682 with a P-CGL2 1684. The N-CGL2 1682 is disposed between the ETL2 1570 and the HTL3 1760 and the P-CGL2 1684 is disposed between the N-CGL2 1682 and the HTL3 1760.

In this aspect, each of the EML1 1540 and the EML3 1740 can be a blue EML. In an exemplary aspect, each of the EML1 1540 and the EML3 1740 can include a host and a blue dopant. The host in each of the EML1 1540 and the EML3 1740 can include the fourth compound H, and the blue dopant in each of the EML1 1540 and the EMI3 1740 can include at least one of the blue phosphorescent material, the blue fluorescent material and the blue delayed fluorescent material. The host and/or the blue dopant in the EML1 1540 can be identical to or different from the host and/or the blue dopant in the EML3 1740. As an example, the blue dopant in the EML1 1540 can have different luminous efficiency and/or emission peak different from the luminous efficiency and/or emission peak of the blue dopant in the EML3 1740.

One of the middle lower EML 1642 and the middle upper EML 1644 of the EML2 1640 can be a green EML and the other of the middle lower EML 1642 and the middle upper EML 1644 of the EML2 1640 can be a red EML. The green EML and the red EML are sequentially disposed to form the EML2 1640. Hereinafter, the EML2 1640 where the middle lower EML 1642 is a red EML and the middle upper EML 1644 is a green EML will be described As an example, the middle lower EML 1642 of the red EML can include the first compound of DF1 of the first delayed fluorescent material having the structure of Formulae 1 to 2, the second compound DF2 of the second delayed fluorescent material having the structure of Formulae 3 to 4, the third compound FD of the fluorescent material having the structure of Formulae 5 to 6, and optionally the fourth compound H of the host having the structure of Formulae 7 to 8. The middle lower EML 1642 can have a single-layered structure, a double-layered structure (FIG. 6) or a triple-layered structure (FIG. 9).

In the middle lower EML 1642, the contents of the fourth compound H can be larger than each of the contents of the first and second compounds DF1 and DF2, and each of the contents of the first and second compound DF1 and DF2 can be larger than the contents of the third compound FD.

The middle upper EML 1644 of the green EML can include a host and a green dopant. The host in the middle upper EML 1644 can include the fourth compound H, and the green dopant in the middle upper EML 1644 can include at least one of the green phosphorescent materials, the green fluorescent materials and the green delayed fluorescent materials as described above.

The OLED D7 emits white light in each of the first to third pixel regions P1, P2 and P3 and the white light passes though the color filter layer 1020 (FIG. 15) correspondingly disposed in the first to third pixel regions P1, P2 and P3. Accordingly, the organic light emitting display device 1000 (FIG. 15) can implement a full-color image.

In FIG. 17, the OLED D7 has a three-stack structure including the first to three emitting parts 1520, 1620 and 1720 which includes the EML1 1540 and the EML3 1740 as a blue EML. Alternatively, the OLED D7 can have a two-stack structure where one of the first emitting part 1520 and the third emitting part 1720 each of which includes the EML1 1540 and the EML3 1740 as a blue EML is omitted.

Example 1 (Ex. 1): Fabrication of OLED

An OLED in which an EML includes Compound 1-1 of Formula 2 (HOMO: −5.9 eV, LUMO: −3.3 eV) as the first compound DF1, Compound 2-1 of Formula 4 (HOMO: −5.8 eV, LUMO: −3.4 eV) as the second compound DF2, Compound 3-1 of Formula 6 (HOMO: −5.5 eV, LUMO: −3.5 eV) as the third compound FD and Compound 4-1 (CBP) of Formula 8 (HOMO: −6.0 eV, LUMO: −2.4 eV) was fabricated. An ITO substrate was washed by UV-treated Ozone before using, and was transferred to a vacuum chamber for depositing emission layer. Subsequently, an anode, an emission layer and a cathode were deposited by evaporation from a heating boat under $10^{-7}$ torr vacuum condition with setting deposition rate of 1 Å/s in the following order:

An anode (ITO, 50 nm); an HIL (HAT-CN, 5 nm); an HTL (NPB, 80 nm); an EBL (TAPC, 10 nm), an EML (Compound 4-1 (49 wt %), Compound 1-1 (25 wt %), Compound 2-1 (25 wt %), Compound 3-1 (1 wt %), 35 nm); an HBL (B3PYMPM, 10 nm); an ETL (TPBi, 35 nm), an EIL (LiF); and a cathode (Al).

The charge injection or transport materials used in the HIL, HTL, EBL, HBL and ETL are indicated below.

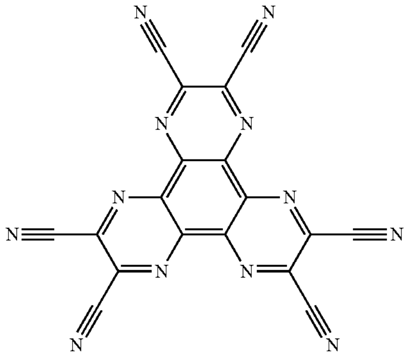

HIL : HAT-CN

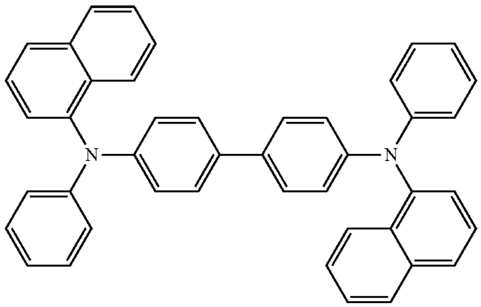

HTL : NPB

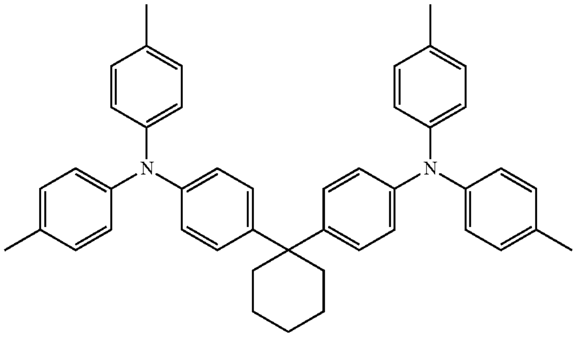

EBL : TAPC

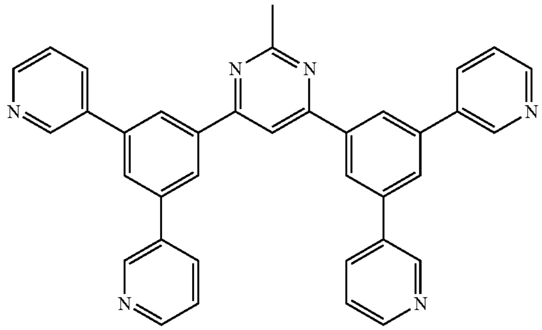

HBL : B3PYMPM

-continued

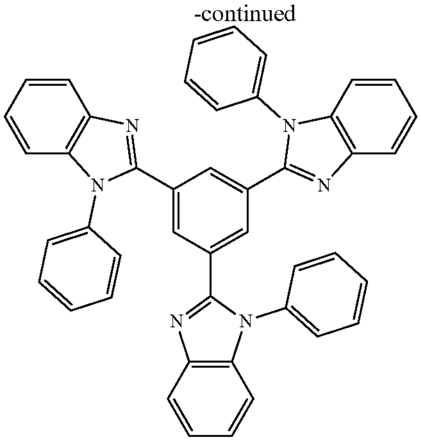

ETL : TPBi

Examples 2-3 (Ex. 2-3): Fabrication of OLED

An OLED was fabricated using the same materials as Example 1, except that each of the contents of the Compound 1-1 and Compound 2-1 in the EML was changed to 10 wt % and 40 wt %, respectively (Ex. 2), or each of the contents of the Compound 1-1 and Compound 2-1 in the EML was changed to 40 wt % and 10 wt %, respectively (Ex. 3).

Example 4 (Ex. 4): Fabrication of OLED

An OLED was fabricated using the same materials as Example 1, except that Compound 3-2 of Formula 6 (HOMO: −5.5 eV, LUMO: −3.5 eV) as the third compound instead of the Compound 3-1 in the EML was used.

Examples 5-6 (Ex. 5-6): Fabrication of OLED

An OLED was fabricated using the same materials as Example 4, except that each of the contents of the Compound 1-1 and Compound 2-1 in the EML was changed to 10 wt % and 40 wt %, respectively (Ex. 5), or each of the contents of the Compound 1-1 and Compound 2-1 in the EML was changed to 40 wt % and 10 wt %, respectively (Ex. 6).

Example 7 (Ex. 7): Fabrication of OLED

An OLED was fabricated using the same materials as Example 1, except that Compound 3-3 of Formula 6 (HOMO: −5.5 eV, LUMO: −3.5 eV) as the third compound instead of the Compound 3-1 in the EML was used.

Examples 8-9 (Ex. 8-9): Fabrication of OLED

An OLED was fabricated using the same materials as Example 7, except that each of the contents of the Compound 1-1 and Compound 2-1 in the EML was changed to 10 wt % and 40 wt %, respectively (Ex. 8), or each of the contents of the Compound 1-1 and Compound 2-1 in the EML was changed to 40 wt % and 10 wt %, respectively (Ex. 9).

Example 10 (Ex. 10): Fabrication of OLED

An OLED was fabricated using the same materials as Example 1, except that Compound 3-4 of Formula 6

(HOMO: −5.6 eV, LUMO: −3.6 eV) as the third compound instead of the Compound 3-1 in the EML was used.

Examples 11-12 (Ex. 11-12): Fabrication of OLED

An OLED was fabricated using the same materials as Example 10, except that each of the contents of the Compound 1-1 and Compound 2-1 in the EML was changed to 10 wt % and 40 wt %, respectively (Ex. 11), or each of the contents of the Compound 1-1 and Compound 2-1 in the EML was changed to 40 wt % and 10 wt %, respectively (Ex. 12).

Example 13 (Ex. 13): Fabrication of OLED

An OLED was fabricated using the same materials as Example 1, except that Compound 2-2 of Formula 4 (HOMO: −5.9 eV, LUMO: −3.5 eV) as the second compound instead of the Compound 2-1 in the EML was used.

Examples 14-15 (Ex. 14-15): Fabrication of OLED

An OLED was fabricated using the same materials as Example 13, except that each of the contents of the Compound 1-1 and Compound 2-1 in the EML was changed to 10 wt % and 40 wt %, respectively (Ex. 14), or each of the contents of the Compound 1-1 and Compound 2-1 in the EML was changed to 40 wt % and 10 wt %, respectively (Ex. 15).

Example 16 (Ex. 16): Fabrication of OLED

An OLED was fabricated using the same materials as Example 1, except that Compound 1-7 of Formula 2 (HOMO: −6.0 eV, LUMO: −3.4 eV, 10 wt %) as the first compound instead of the Compound 1-1, Compound 2-2 (40 wt %) of Formula 4 as the second compound instead of the Compound 2-1 and Compound 3-4 (1 wt %) as the third compound instead of the Compound 3-1 in the EML were used.

Example 17 (Ex. 17): Fabrication of OLED

An OLED was fabricated using the same materials as Example 1, except that Compound 1-8 of Formula 2 (HOMO: −5.9 eV, LUMO: −3.2 eV, 10 wt %) as the first compound instead of the Compound 1-1, Compound 2-1 (40 wt %) as the second compound and Compound 3-4 (1 wt %) as the third compound instead of the Compound 3-1 in the EML were used.

Example 18 (Ex. 18): Fabrication of OLED

An OLED was fabricated using the same materials as Example 17, except that the Compound 2-2 as the second compound instead of the Compound 2-1 in the EML was used.

Example 19 (Ex. 19): Fabrication of OLED

An OLED was fabricated using the same materials as Example 17, except that the Compound 2-5 of Formula 4 as the second compound instead of the Compound 2-1 and the Compound 3-1 of Formula 6 as the third compound instead of the Compound 3-4 in the EML were used.

Example 20 (Ex. 20): Fabrication of OLED

An OLED was fabricated using the same materials as Example 17, except that Compound 1-11 of Formula 2 (HOMO: −5.8 eV, LUMO: −3.2 eV) as the first compound instead of the Compound 1-8 in the EML was used.

Example 21 (Ex. 21): Fabrication of OLED

An OLED was fabricated using the same materials as Example 17, except that the Compound 1-11 of Formula 2 as the first compound instead of the Compound 1-8, the Compound 2-5 of Formula 4 as the second compound instead of the Compound 2-1 and the Compound 3-1 as the third compound instead of the Compound 3-4 in the EML were used.

Example 22 (Ex. 22): Fabrication of OLED

An OLED was fabricated using the same materials as Example 17, except that the Compound 2-2 of Formula 4 as the second compound instead of the Compound 2-1 and the Compound 3-1 of Formula 6 as the third compound instead of the Compound 3-4 were used.

Example 23 (Ex. 23): Fabrication of OLED

An OLED was fabricated using the same materials as Example 17, except that the Compound 2-4 as the second compound instead of the Compound 2-1 and the Compound 3-1 of Formula 6 as the third compound instead of the Compound 3-4 were used.

The following table 1 indicates the first to third compounds and HOMO energy levels and LUMO energy levels of the first to third compounds each of which was used in the EML of the OLEDs fabricated in Examples 1 to 23.

TABLE 1

| | First, Second, Third Compounds in EML | | | | | |
|---|---|---|---|---|---|---|
| | First Compound | | Second Compound | | Third Compound | |
| Sample | | HOMO/LUMO(eV) | | HOMO/LUMO(eV) | | HOMO/LUMO(eV) |
| Ex. 1 | 1-1 | −5.9/−3.3 | 2-1 | −5.8/−3.4 | 3-1 | −5.5/−3.5 |
| Ex. 2 | 1-1 | −5.9/−3.3 | 2-1 | −5.8/−3.4 | 3-1 | −5.5/−3.5 |
| Ex. 3 | 1-1 | −5.9/−3.3 | 2-1 | −5.8/−3.4 | 3-1 | −5.5/−3.5 |
| Ex. 4 | 1-1 | −5.9/−3.3 | 2-1 | −5.8/−3.4 | 3-2 | −5.5/−3.5 |
| Ex. 5 | 1-1 | −5.9/−3.3 | 2-1 | −5.8/−3.4 | 3-2 | −5.5/−3.5 |
| Ex. 6 | 1-1 | −5.9/−3.3 | 2-1 | −5.8/−3.4 | 3-2 | −5.5/−3.5 |
| Ex. 7 | 1-1 | −5.9/−3.3 | 2-1 | −5.8/−3.4 | 3-3 | −5.5/−3.5 |
| Ex. 8 | 1-1 | −5.9/−3.3 | 2-1 | −5.8/−3.4 | 3-3 | −5.5/−3.5 |
| Ex. 9 | 1-1 | −5.9/−3.3 | 2-1 | −5.8/−3.4 | 3-3 | −5.5/−3.5 |
| Ex. 10 | 1-1 | −5.9/−3.3 | 2-1 | −5.8/−3.4 | 3-4 | −5.6/−3.6 |
| Ex. 11 | 1-1 | −5.9/−3.3 | 2-1 | −5.8/−3.4 | 3-4 | −5.6/−3.6 |

TABLE 1-continued

| First, Second, Third Compounds in EML | | | | | | |
|---|---|---|---|---|---|---|
| | First Compound | | Second Compound | | Third Compound | |
| Sample | | HOMO/LUMO(eV) | | HOMO/LUMO(eV) | | HOMO/LUMO(eV) |
| Ex. 12 | 1-1 | −5.9/−3.3 | 2-1 | −5.8/−3.4 | 3-4 | −5.6/−3.6 |
| Ex. 13 | 1-1 | −5.9/−3.3 | 2-2 | −5.9/−3.5 | 3-1 | −5.5/−3.5 |
| Ex. 14 | 1-1 | −5.9/−3.3 | 2-2 | −5.9/−3.5 | 3-1 | −5.5/−3.5 |
| Ex. 15 | 1-1 | −5.9/−3.3 | 2-2 | −5.9/−3.5 | 3-1 | −5.5/−3.5 |
| Ex. 16 | 1-7 | −6.0/−3.4 | 2-2 | −5.9/−3.5 | 3-4 | −5.6/−3.6 |
| Ex. 17 | 1-8 | −5.9/−3.2 | 2-1 | −5.8/−3.4 | 3-4 | −5.6/−3.6 |
| Ex. 18 | 1-8 | −5.9/−3.2 | 2-2 | −5.9/−3.5 | 3-4 | −5.6/−3.6 |
| Ex. 19 | 1-8 | −5.9/−3.2 | 2-5 | −5.7/−3.3 | 3-1 | −5.5/−3.5 |
| Ex. 20 | 1-11 | −5.8/−3.2 | 2-1 | −5.8/−3.4 | 3-4 | −5.6/−3.6 |
| Ex. 21 | 1-11 | −5.8/−3.2 | 2-5 | −5.7/−3.3 | 3-1 | −5.5/−3.5 |
| Ex. 22 | 1-8 | −5.9/−3.2 | 2-2 | −5.9/−3.5 | 3-1 | −5.5/−3.5 |
| Ex. 23 | 1-8 | −5.9/−3.2 | 2-4 | −5.6/−3.2 | 3-1 | −5.5/−3.5 |

Comparative Example 1 (Ref. 1): Fabrication of OLED

An OLED was fabricated using the same materials as Example 1, except that Compound 4-1 of Formula 8 (69 wt %) as the fourth compound, Compound 1-1 of Formula 2 (30 wt %) as the first compound and Compound 3-1 of Formula 6 (1 wt %) as the third compound in the EML without using the second compound were used.

Comparative Example 2 (Ref. 2): Fabrication of OLED

An OLED was fabricated using the same materials as Example 1, except that Compound 4-1 of Formula 8 (49 wt %) as the fourth compound, Compound 1-1 of Formula 2 (50 wt %) as the first compound and Compound 3-1 of Formula 6 (1 wt %) as the third compound in the EML without using the second compound were used.

Comparative Example 3 (Ref. 3): Fabrication of OLED

An OLED was fabricated using the same materials as Example 1, except that Compound 4-1 of Formula 8 (29 wt %) as the fourth compound, Compound 1-1 of Formula 2 (70 wt %) as the first compound and Compound 3-1 of Formula 6 (1 wt %) as the third compound in the EML without using the second compound were used.

Comparative Example 4 (Ref. 4): Fabrication of OLED

An OLED was fabricated using the same materials as Example 1, except that Compound 4-1 of Formula 8 (69 wt %) as the fourth compound, the following Ref. 1 Compound (30 wt %) as the first compound and the following Ref. 4 Compound (1 wt %) as the third compound in the EML without using the second compound were used.

Comparative Example 5 (Ref. 5): Fabrication of OLED

An OLED was fabricated using the same materials as Example 1, except that Compound 4-1 of Formula 8 (49 wt %) as the fourth compound, the following Ref. 1 Compound (50 wt %) as the first compound and the following Ref. 4 Compound (1 wt %) as the third compound in the EML without using the second compound were used.

Comparative Example 6 (Ref. 6): Fabrication of OLED

An OLED was fabricated using the same materials as Example 1, except that Compound 4-1 of Formula 8 (29 wt %) as the fourth compound, the following Ref. 1 Compound (70 wt %) as the first compound and the following Ref. 4 Compound (1 wt %) as the third compound in the EML without using the second compound were used.

Comparative Example 7 (Ref. 7): Fabrication of OLED

An OLED was fabricated using the same materials as Example 1, except that the following Ref 2 Compound as the second compound instead of the Compound 2-1 in the EML was used.

Comparative Examples 8-9 (Ref 8-9): Fabrication of OLED

An OLED was fabricated using the same materials as Comparative Example 7, except that each of the contents of the Compound 1-1 and the Ref. 2 Compound in the EML was changed to 10 wt % and 40 wt %, respectively (Ref. 8), or each of the contents of the Compound 1-1 and the Ref. 2 Compound in the EML was changed to 40 wt % and 10 wt %, respectively (Ref. 9).

Comparative Example 10 (Ref. 10): Fabrication of OLED

An OLED was fabricated using the same materials as Example 1, except that the following Ref. 1 Compound as the first compound instead of the Compound 1-1 in the EML was used.

Comparative Examples 11-13 (Ref. 11-13): Fabrication of OLED

An OLED was fabricated using the same materials as Comparative Example 10, except that the Compound 2-2 of Formula 4 (Ref 11), the following Ref. 2 Compound (Ref. 12) or the following Ref. 3 Compound (Ref. 3) as the second compound instead of the Compound 2-1 in the EML was used.

Comparative Example 14 (Ref. 10): Fabrication of OLED

An OLED was fabricated using the same materials as Example 1, except that the following Ref 4 Compound as the third compound instead of the Compound 3-1 in the EML was used.

Comparative Examples 15-17 (Ref. 15-17): Fabrication of OLED

An OLED was fabricated using the same materials as Comparative Example 14, except that the Compound 2-2 of Formula 4 (Ref 15), the following Ref. 2 Compound (Ref. 16) or the following Ref 3 Compound (Ref. 17) as the second compound instead of the Compound 2-1 in the EML was used.

Comparative Example 18 (Ref. 18): Fabrication of OLED

An OLED was fabricated using the same materials as Comparative Example 14, except that the Compound 1-7 of Formula 2 as the first compound instead of the Compound 1-7 in the EML was used.

Comparative Examples 19-20 (Ref. 19-20): Fabrication of OLED

An OLED was fabricated using the same materials as Comparative Example 18, except that each of the contents of the Compound 1-7 and the Compound 2-1 in the EML was changed to 10 wt % and 40 wt %, respectively (Ref. 19), or each of the contents of the Compound 1-7 and the Compound 2-1 in the EML was changed to 40 wt % and 10 wt %, respectively (Ref. 20).

Comparative Example 21 (Ref. 21): Fabrication of OLED

An OLED was fabricated using the same materials as Comparative Example 18, except that the Compound 2-2 of Formula 4 as the second compound instead of the Compound 2-1 in the EML was used.

Comparative Examples 22-23 (Ref. 22-23): Fabrication of OLED

An OLED was fabricated using the same materials as Comparative Example 21, except that each of the contents of the Compound 1-7 and the Compound 2-2 in the EML was changed to 10 wt % and 40 wt %, respectively (Ref. 22), or each of the contents of the Compound 1-7 and the Compound 2-2 in the EML was changed to 40 wt % and 10 wt %, respectively (Ref. 23).

Comparative Example 24 (Ref. 24): Fabrication of OLED

An OLED was fabricated using the same materials as Comparative Example 18, except that the following Ref 2 Compound as the second compound instead of the Compound 2-1 in the EML was used.

Comparative Examples 25-26 (Ref. 25-26): Fabrication of OLED

An OLED was fabricated using the same materials as Comparative Example 24, except that each of the contents of the Compound 1-7 and the Ref. 2 Compound in the EML was changed to 10 wt % and 40 wt %, respectively (Ref. 25), or each of the contents of the Compound 1-7 and the Ref. 2 Compound in the EML was changed to 40 wt % and 10 wt %, respectively (Ref. 26).

[Reference Compound]

Ref. 1

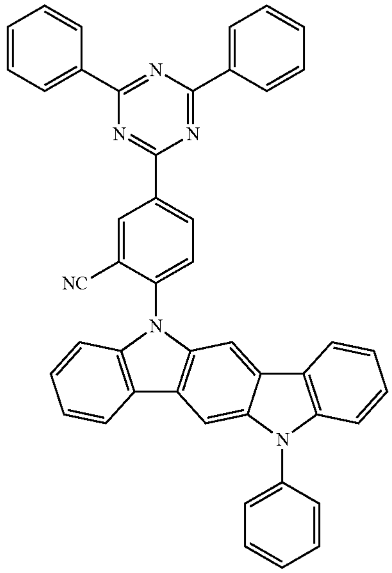

-continued

Ref. 2

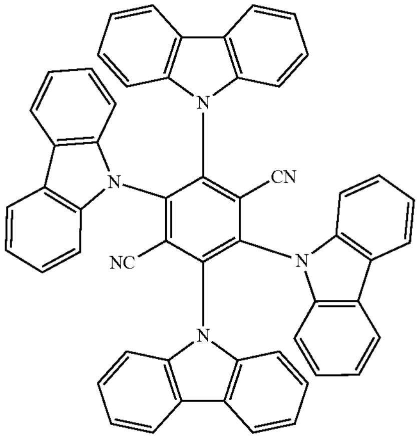

Ref. 3

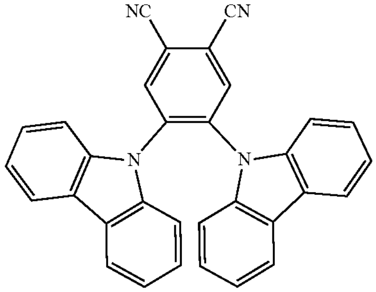

-continued

Ref. 4

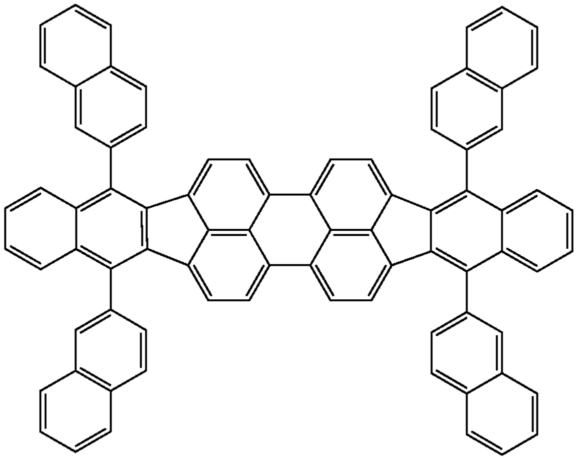

The following table 2 indicates the first to third compounds and HOMO energy levels and LUMO energy levels of the first to third compounds each of which was used in the EML of the OLEDs fabricated in Comparative Examples 1 to 26.

TABLE 2

| First, Second, Third Compounds in EML | | | | | | |
|---|---|---|---|---|---|---|
| | First Compound | | Second Compound | | Third Compound | |
| Sample | | HOMO/LUMO(eV) | | HOMO/LUMO(eV) | | HOMO/LUMO |
| Ref. 1 | 1-1 | −5.9/−3.3 | — | — | 3-1 | −5.5/−3.5 |
| Ref. 2 | 1-1 | −5.9/−3.3 | — | — | 3-1 | −5.5/−3.5 |
| Ref. 3 | 1-1 | −5.9/−3.3 | — | — | 3-1 | −5.5/−3.5 |
| Ref. 4 | Ref. 1 | −5.4/−2.8 | — | — | Ref. 4 | −4.9/−2.8 |
| Ref. 5 | Ref. 1 | −5.4/−2.8 | — | — | Ref. 4 | −4.9/−2.8 |
| Ref. 6 | Ref. 1 | −5.4/−2.8 | — | — | Ref. 4 | −4.9/−2.8 |
| Ref. 7 | 1-1 | −5.9/−3.3 | Ref. 2 | −6.0/−3.8 | 3-1 | −5.5/−3.5 |
| Ref. 8 | 1-1 | −5.9/−3.3 | Ref. 2 | −6.0/−3.8 | 3-1 | −5.5/−3.5 |
| Ref. 9 | 1-1 | −5.9/−3.3 | Ref. 2 | −6.0/−3.8 | 3-1 | −5.5/−3.5 |
| Ref. 10 | Ref. 1 | −5.4/−2.8 | 2-1 | −5.8/−3.4 | 3-1 | −5.5/−3.5 |
| Ref. 11 | Ref. 1 | −5.4/−2.8 | 2-2 | −5.9/−3.5 | 3-1 | −5.5/−3.5 |
| Ref. 12 | Ref. 1 | −5.4/−2.8 | Ref. 2 | −6.0/−3.8 | 3-1 | −5.5/−3.5 |
| Ref. 13 | Ref. 1 | −5.4/−2.8 | Ref. 3 | −5.8/−3.0 | 3-1 | −5.5/−3.5 |
| Ref. 14 | 1-1 | −5.9/−3.3 | 2-1 | −5.8/−3.4 | Ref. 4 | −4.9/−2.8 |
| Ref. 15 | 1-1 | −5.9/−3.3 | 2-2 | −5.9/−3.5 | Ref. 4 | −4.9/−2.8 |
| Ref. 16 | 1-1 | −5.9/−3.3 | Ref. 2 | −6.0/−3.8 | Ref. 4 | −4.9/−2.8 |
| Ref. 17 | 1-1 | −5.9/−3.3 | Ref. 3 | −5.8/−3.0 | Ref. 4 | −4.9/−2.8 |
| Ref. 18 | 1-7 | −6.0/−3.4 | 2-1 | −5.8/−3.4 | Ref. 4 | −4.9/−2.8 |
| Ref. 19 | 1-7 | −6.0/−3.4 | 2-1 | −5.8/−3.4 | Ref. 4 | −4.9/−2.8 |
| Ref. 20 | 1-7 | −6.0/−3.4 | 2-1 | −5.8/−3.4 | Ref. 4 | −4.9/−2.8 |
| Ref. 21 | 1-7 | −6.0/−3.4 | 2-2 | −5.9/−3.5 | Ref. 4 | −4.9/−2.8 |
| Ref. 22 | 1-7 | −6.0/−3.4 | 2-2 | −5.9/−3.5 | Ref. 4 | −4.9/−2.8 |
| Ref. 23 | 1-7 | −6.0/−3.4 | 2-2 | −5.9/−3.5 | Ref. 4 | −4.9/−2.8 |
| Ref. 24 | 1-7 | −6.0/−3.4 | Ref. 2 | −6.0/−3.8 | Ref. 4 | −4.9/−2.8 |
| Ref. 25 | 1-7 | −6.0/−3.4 | Ref. 2 | −6.0/−3.8 | Ref. 4 | −4.9/−2.8 |
| Ref. 26 | 1-7 | −6.0/−3.4 | Ref. 2 | −6.0/−3.8 | Ref. 4 | −4.9/−2.8 |

Experimental Example 1: Measurement of Luminous Properties of OLED

Each of the OLED fabricated in Ex. 1-23 and Ref. 1-26 was connected to an external power source and then luminous properties for all the diodes were evaluated using a constant current source (KEITHLEY) and a photometer PR650 at room temperature. In particular, hole trap, electron trap, driving voltage (V), external quantum efficiency (EQE, %) and lifespan ($LT_{95}$) at 15.4 mA/$cm^2$ current density of the OLEDs were measured. The measurement results for the OLEDs fabricated in Examples are shown in the following Table 3 and the measurement results for the OLEDs fabricated in Comparative Examples are shown in the following Table 4:

TABLE 3

| Luminous Properties of OLED | | | | | |
|---|---|---|---|---|---|
| | Hole | Electron | @ 15.4 mA/$cm^2$ | | |
| Sample | trap | trap | V | EQE (%) | $T_{95}$Chr) |
| Ex. 1 | N | N | 4.08 | 17.6 | 472 |
| Ex. 2 | N | N | 4.05 | 18.0 | 488 |
| Ex. 3 | N | N | 4.26 | 16.9 | 435 |
| Ex. 4 | N | N | 4.07 | 16.8 | 367 |
| Ex. 5 | N | N | 4.01 | 17.0 | 379 |
| Ex. 6 | N | N | 4.19 | 16.5 | 315 |
| Ex. 7 | N | N | 4.25 | 16.0 | 350 |
| Ex. 8 | N | N | 4.11 | 16.3 | 368 |
| Ex. 9 | N | N | 4.93 | 15.1 | 312 |
| Ex. 10 | N | N | 4.32 | 15.4 | 322 |
| Ex. 11 | N | N | 4.24 | 15.9 | 339 |
| Ex. 12 | N | N | 4.98 | 14.7 | 305 |
| Ex. 13 | N | N | 4.49 | 13.1 | 113 |
| Ex. 14 | N | N | 4.38 | 13.4 | 101 |
| Ex. 15 | N | N | 4.43 | 12.6 | 142 |
| Ex. 16 | N | N | 4.13 | 16.0 | 303 |
| Ex. 17 | N | N | 4.09 | 16.4 | 333 |
| Ex. 18 | N | N | 4.39 | 15.2 | 297 |
| Ex. 19 | N | N | 4.27 | 17.1 | 390 |
| Ex. 20 | N | N | 4.08 | 15.7 | 371 |
| Ex. 21 | N | N | 4.10 | 17.3 | 399 |
| Ex. 22 | N | N | 4.14 | 15.6 | 350 |
| Ex. 23 | N | N | 4.40 | 14.5 | 300 |

TABLE 4

| Luminous Properties of OLED | | | | | |
|---|---|---|---|---|---|
| | Hole | Electron | @ 15.4 mA/$cm^2$ | | |
| Sample | trap | trap | V | EQE (%) | $T_{95}$Chr) |
| Ref. 1 | N | N | 4.12 | 13.5 | 33 |
| Ref. 2 | N | N | 4.26 | 13.3 | 95 |
| Ref. 3 | N | N | 4.40 | 13.1 | 237 |
| Ref. 4 | Y | N | 4.43 | 11.6 | 150 |
| Ref. 5 | Y | N | 4.49 | 10.2 | 82 |
| Ref. 6 | Y | N | 4.67 | 10.1 | 150 |
| Ref. 7 | N | Y | 4.85 | 12.2 | 80 |
| Ref. 8 | N | Y | 4.80 | 12.6 | 77 |
| Ref. 9 | N | Y | 4.89 | 11.6 | 95 |
| Ref. 10 | Y | Y | 4.88 | 9.3 | 53 |
| Ref. 11 | Y | Y | 4.80 | 8.4 | 67 |
| Ref. 12 | Y | Y | 4.65 | 8.5 | 95 |
| Ref. 13 | Y | N | 4.35 | 11.5 | 107 |
| Ref. 14 | N | Y | 4.87 | 10.6 | 52 |
| Ref. 15 | N | Y | 4.54 | 10.9 | 61 |
| Ref. 16 | N | Y | 4.60 | 9.4 | 70 |
| Ref. 17 | Y | N | 4.55 | 10.0 | 68 |
| Ref. 18 | Y | N | 4.42 | 12.9 | 151 |
| Ref. 19 | Y | N | 4.40 | 13.5 | 133 |
| Ref. 20 | Y | N | 4.69 | 11.0 | 162 |

TABLE 4-continued

| Luminous Properties of OLED | | | | | |
|---|---|---|---|---|---|
| | Hole | Electron | @ 15.4 mA/$cm^2$ | | |
| Sample | trap | trap | V | EQE (%) | $T_{95}$Chr) |
| Ref. 21 | Y | N | 4.61 | 12.4 | 147 |
| Ref. 22 | Y | N | 4.45 | 13.1 | 140 |
| Ref. 23 | Y | N | 4.70 | 11.4 | 155 |
| Ref. 24 | Y | N | 4.58 | 11.9 | 120 |
| Ref. 25 | Y | N | 4.97 | 9.7 | 89 |
| Ref. 26 | Y | N | 4.36 | 12.4 | 112 |

As indicated in Tables 3 and 4, in the OLEDs fabricated in Examples where the HOMO energy level of the first compound of the first delayed fluorescent material was designed to be identical to or lower than the HOMO energy level of the second compound of the second delayed fluorescent material, the HOMO energy level of the second compound was designed to be identical to or lower than the HOMO energy level of the third compound of the fluorescent material, the LUMO energy level of the first compound was designed to be identical or higher than the LUMO energy level of the second compound, and the LUMO energy level of the second compound was designed to be identical or higher than the LUMO energy level of the third compound, optical properties were improved extremely.

On the contrary, in the OLEDs fabricated in Ref 7-26 wherein the HOMO and/or LUMO energy levels among the delayed fluorescent materials and fluorescent materials are not regulated with suing two delayed fluorescent materials, optical properties were reduced owing to hole traps and/or electron traps.

More particularly, compared to the OLEDs fabricated in Ref. 1-6 where one delayed fluorescent material and one fluorescent material were applied in the EML, the OLED fabricated in Ex. 1-26 reduced its driving voltage by maximally 14.1% and improved its EQE and lifespan ($LT_{95}$) by maximally 78.2% and 13.8 times, respectively. In addition, compared to the OLEDs fabricated in Ref. 7-26, the OLED fabricated in Ex. 1-26 reduced its driving voltage by maximally 19.3% and improved its EQE and lifespan by maximally 114.3% and 9.4 times.

It will be apparent to those skilled in the art that various modifications and variations can be made in the OLED and the organic light emitting device including the OLED of the present disclosure without departing from the technical idea or scope of the disclosure. Thus, it is intended that the present disclosure cover the modifications and variations of this disclosure provided they come within the scope of the appended claims and their equivalents.

What is claimed is:

1. An organic light emitting diode comprising:

a first electrode;

a second electrode facing the first electrode; and an emissive layer disposed between the first and second electrodes and including at least one emitting material layer, wherein the at least one emitting material layer includes a first compound, a second compound and a third compound, wherein a content of each of the first compound and the second compound in the at least one emitting material layer is 10 wt % to 40 wt %, and a content of the third compound in the at least one emitting material layer is 0.5 wt % to 5 wt %, wherein the content of the first compound in the at least one emitting material layer is lower than the content of the second compound in the at least one emitting material layer, and wherein the first compound has the following structure of Formula 1 or a structure formed by linking two structures of Formula 1 via a direct bond, the second compound has the following structure of Formula 3 and the third compound has the following structure of Formula 5:

[Formula 1]

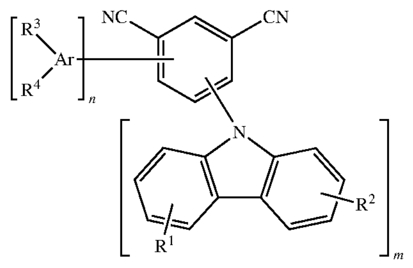

wherein, in Formula 1, each of $R^1$ and $R^2$ is independently hydrogen, deuterium, tritium, unsubstituted or substituted $C_1$-$C_{20}$ alkyl, an unsubstituted or substituted $C_6$-$C_{30}$ aromatic group or an unsubstituted or substituted $C_3$-$C_{30}$ hetero aromatic group;

each of $R^3$ and $R^4$ is independently an unsubstituted or substituted carbazolyl group;

Ar is an unsubstituted or substituted $C_6$-$C_{30}$ aromatic ring or an unsubstituted or substituted $C_3$-$C_{30}$ hetero aromatic group;

m is an integer of 1 to 4; and n is an integer of 0 to 1, wherein m plus n is an integer of 1 to 4,

[Formula 3]

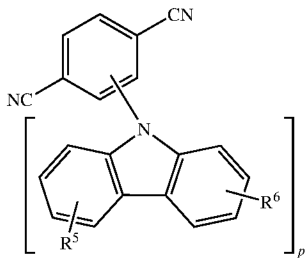

wherein, in Formula 3, each of $R^5$ and $R^6$ is independently hydrogen, deuterium, tritium, unsubstituted or substituted $C_1$-$C_{20}$ alkyl, an unsubstituted or substituted $C_6$-$C_{30}$ aromatic group or an unsubstituted or substituted $C_3$-$C_{30}$ hetero aromatic group, wherein at least one of $R^5$ and $R^6$ is an unsubstituted or substituted C1-$C_{20}$ alkyl, an unsubstituted or substituted $C_6$-$C_{30}$ aromatic group or an unsubstituted or substituted $C_3$-$C_{30}$ hetero aromatic group; and p is an integer of 1 to 4,

[Formula 5]

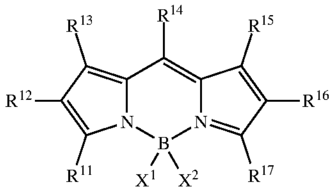

wherein, in Formula 5, each of $R^{11}$ to $R^{17}$ is independently hydrogen, deuterium, tritium, an unsubstituted or substituted $C_1$-$C_{20}$ alkyl, an unsubstituted or substituted $C_6$-$C_{30}$ aromatic group or an unsubstituted or substituted $C_3$-$C_{30}$ hetero aromatic group; and each of $X^1$ and $X^2$ is independently a halogen atom.

2. The organic light emitting diode of claim 1, wherein a Highest Occupied Molecular Orbital (HOMO) energy level of the first compound is identical to or lower than a HOMO energy level of the second compound, and wherein the HOMO energy level of the second compound is identical to or lower than a HOMO energy level of the third compound.

3. The organic light emitting diode of claim 1, wherein a HOMO energy level of the first compound and a HOMO energy level of the second compound satisfy the following relationship in Equation (1), and wherein the HOMO energy level of the second compound and a HOMO energy level of the third compound satisfy the following relationship in Equation (2):

$$-0.3\text{ eV} \leq HOMO^{DF1} - HOMO^{DF2} \leq 0\text{ eV}; \quad (1)$$

$$-0.4\text{ eV} \leq HOMO^{DF2} - HOMO^{FD} \leq 0\text{ eV}, \quad (2)$$

wherein $HOMO^{DF1}$ indicates a HOMO energy level of the first compound, $HOMO^{DF2}$ indicates a HOMO energy level of the second compound and $HOMO^{FD}$ indicates a HOMO energy level of the third compound.

4. The organic light emitting diode of claim 1, wherein a Lowest Unoccupied Molecular Orbital (LUMO) energy level of the first compound is identical to or higher than a LUMO energy level of the second compound, and wherein the LUMO energy level of the second compound is identical to or higher than a LUMO energy level of the third compound.

5. The organic light emitting diode of claim 1, wherein a LUMO energy level of the first compound and a LUMO energy level of the second compound satisfy the following relationship in Equation (3), and wherein the LUMO energy level of the second compound and a LUMO energy level of the third compound satisfy the following relationship in Equation (4):

$$0\text{ eV} \leq LUMO^{DF1} - LUMO^{DF2} \leq 0.3\text{ eV}; \quad (3)$$

$$0\text{ eV} \leq LUMO^{DF2} - LUMO^{FD} \leq 0.3\text{ eV}, \quad (4)$$

wherein $LUMO^{DF1}$ indicates a LUMO energy level of the first compound, $LUMO^{DF2}$ indicates a LUMO energy level of the second compound and $LUMO^{FD}$ indicates a LUMO energy level of the third compound.
6. The organic light emitting diode of claim 1, wherein the first compound is selected from:
1-1
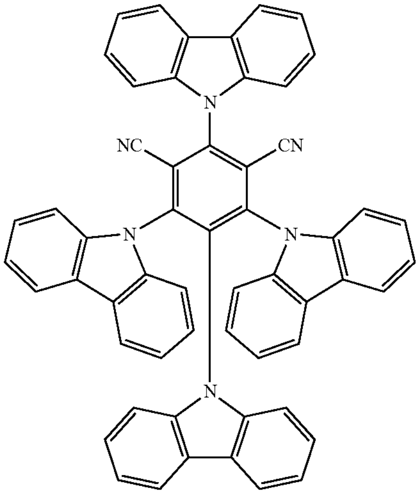
1-2
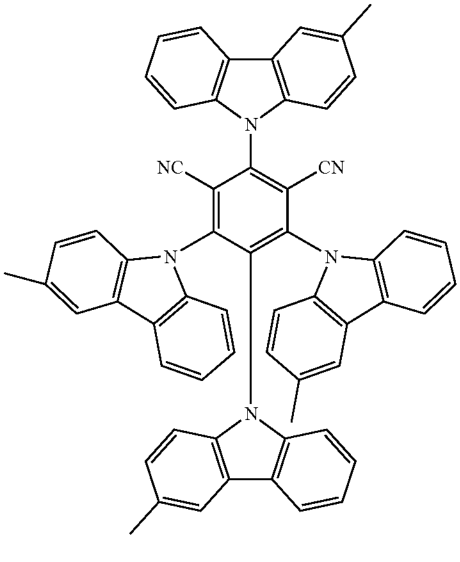
-continued
1-3
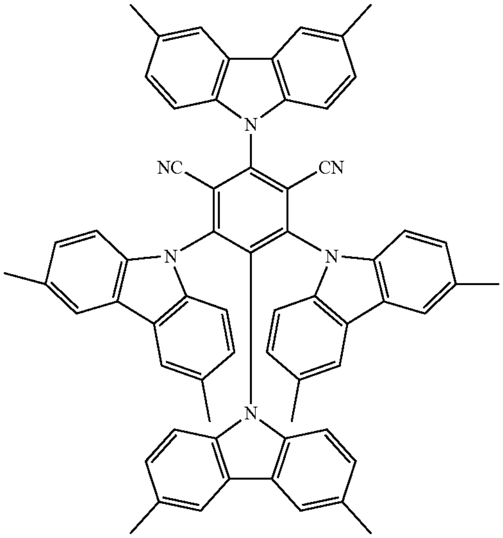
1-4
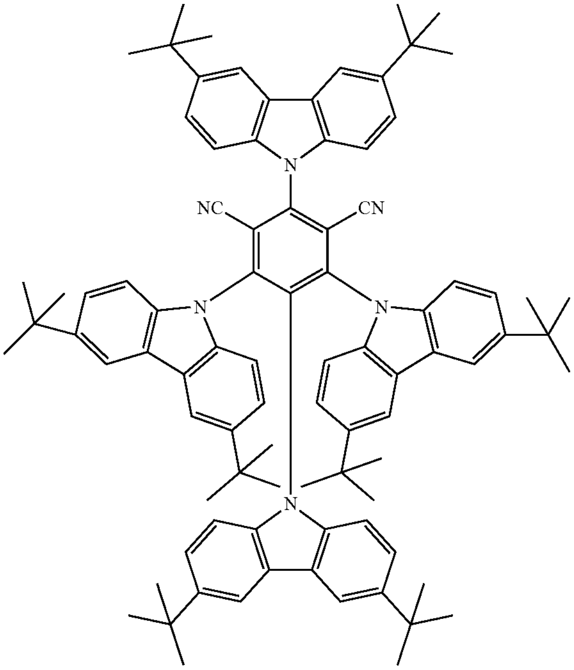

-continued
1-5
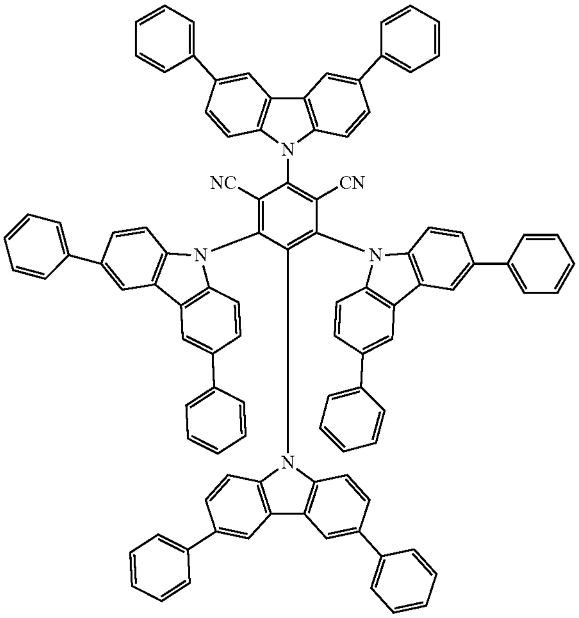
1-6
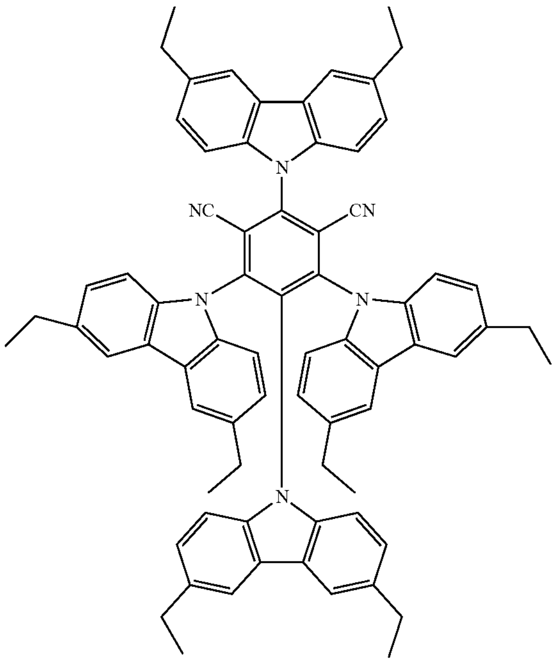
1-7
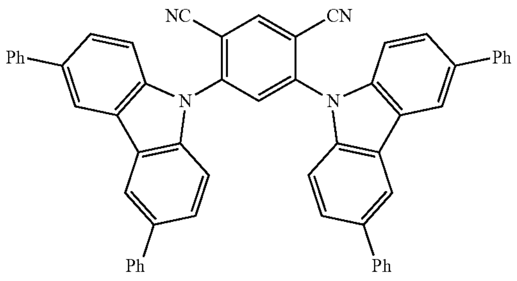
-continued
1-8
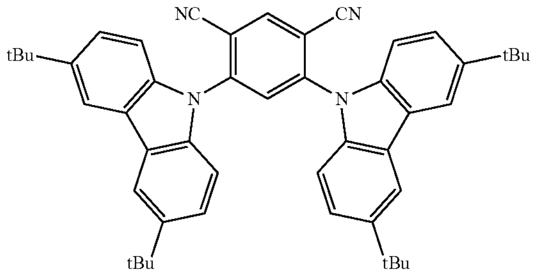
1-9
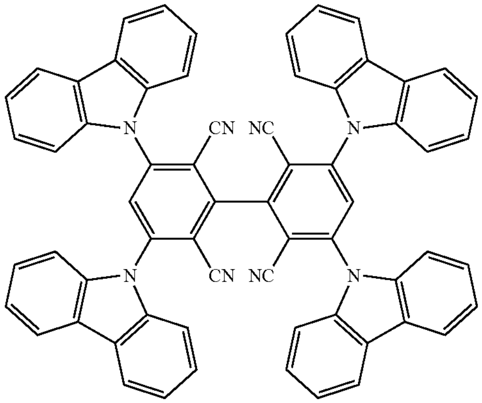
1-10
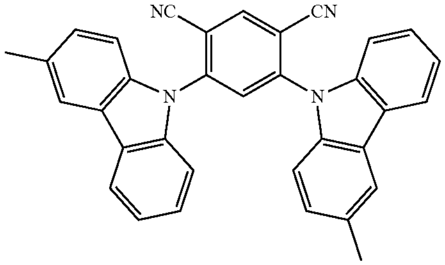
1-11
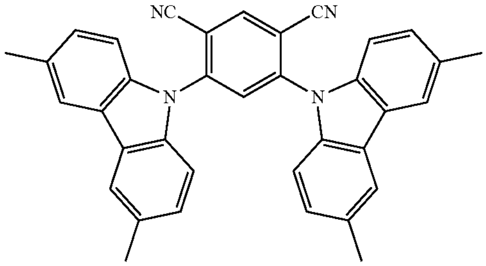
1-12
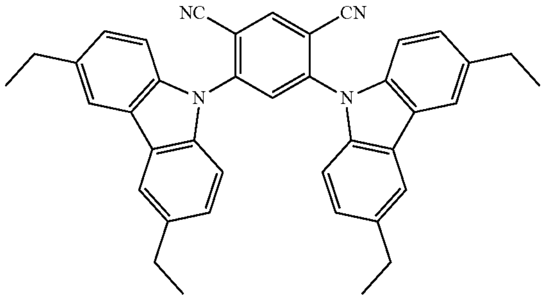

-continued
1-13
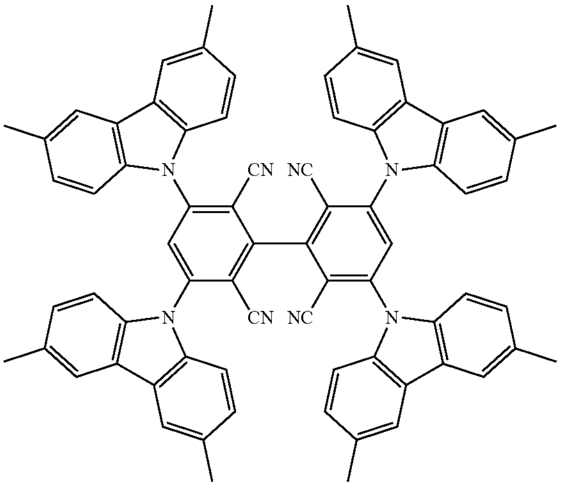
1-14
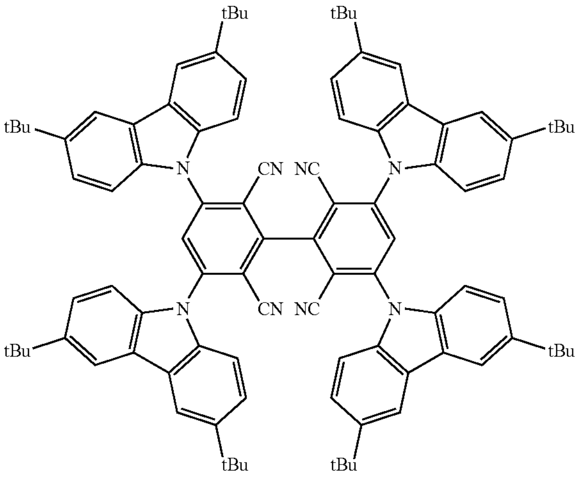
1-15
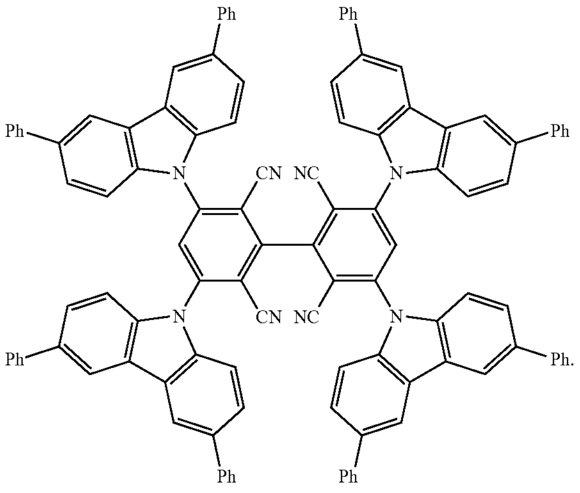
7. The organic light emitting diode of claim 1, wherein the second compound is selected from:
2-1
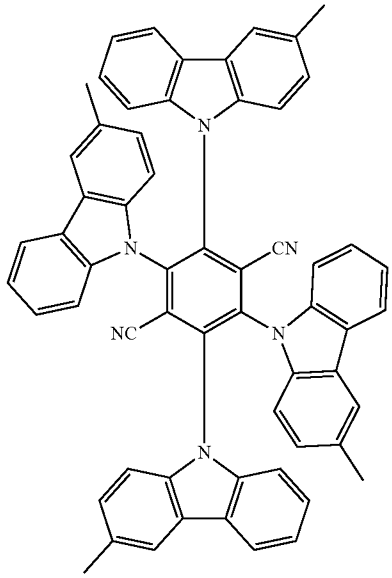
2-2
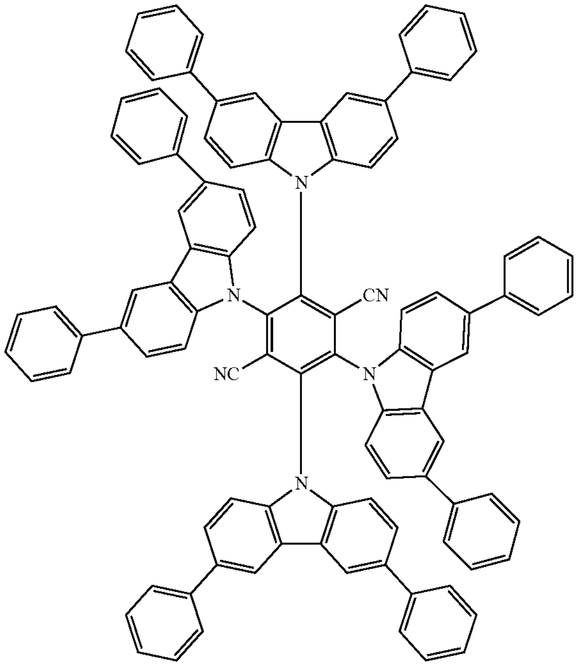

-continued
2-3
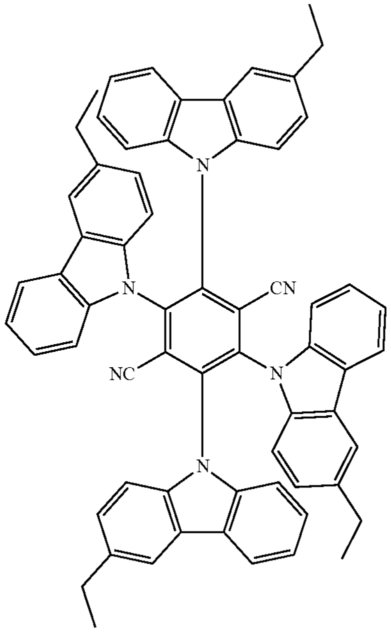
2-7
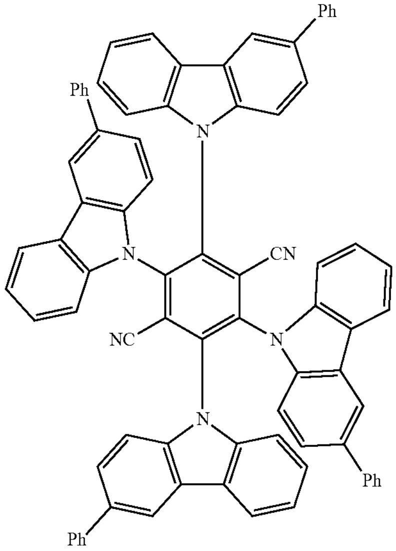
-continued
2-8
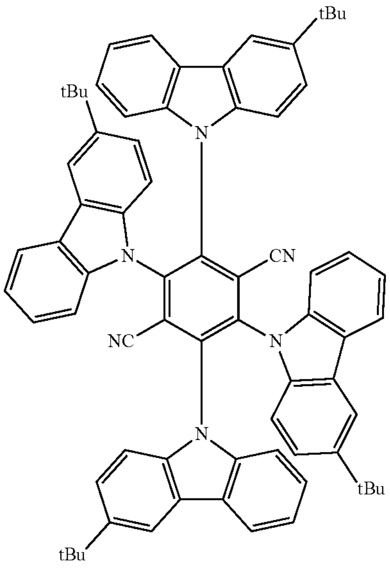
2-9
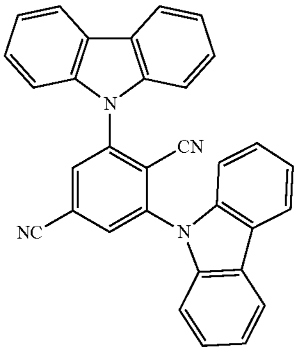
2-10
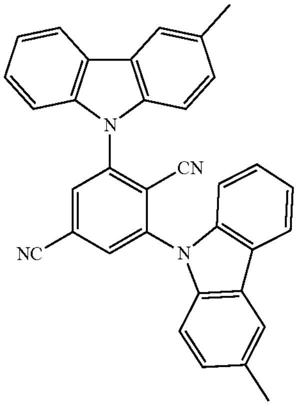

-continued
2-11
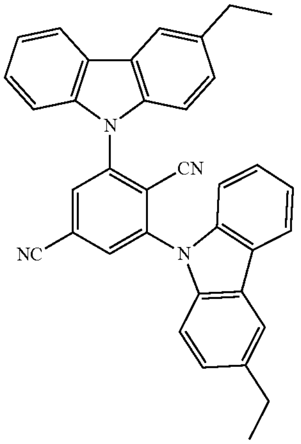
2-12
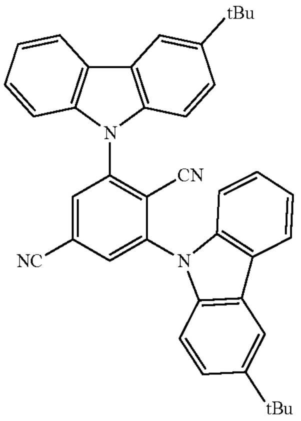
2-13
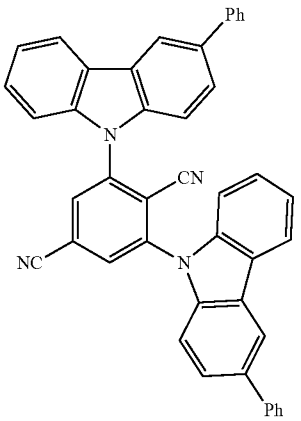
-continued
2-14
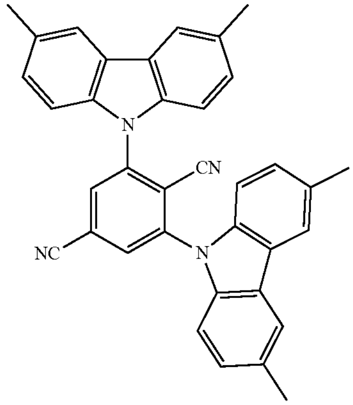
2-15
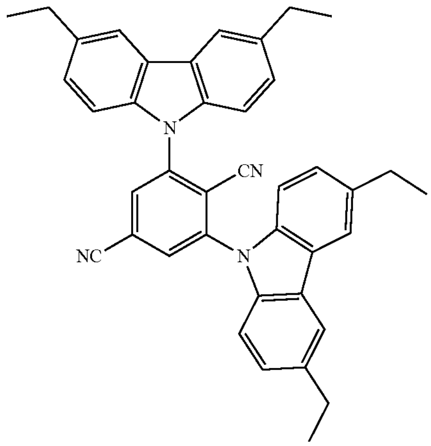
2-16
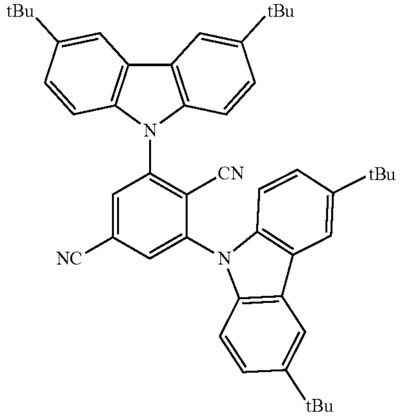

-continued 2-17

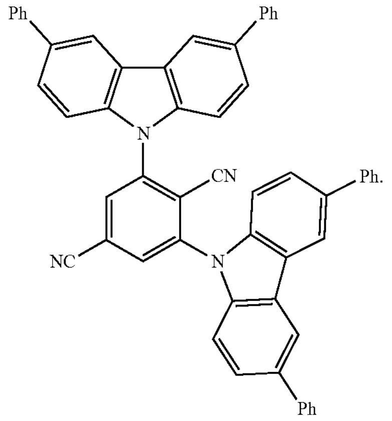

8. The organic light emitting diode of claim 1, wherein each of $R^{11}$, $R_{13}$, $R^{14}$, $R^{15}$ and $R^{17}$ is independently an unsubstituted or substituted $C_6$-$C_{30}$ aryl or an unsubstituted or substituted $C_3$-$C_{30}$ hetero aryl, and wherein each of $R^{12}$ and $R^{16}$ is independently hydrogen, deuterium, tritium or unsubstituted or substituted $C_1$-$C_{20}$ alkyl.

9. The organic light emitting diode of claim 1, wherein the third compound is selected from:

3-1

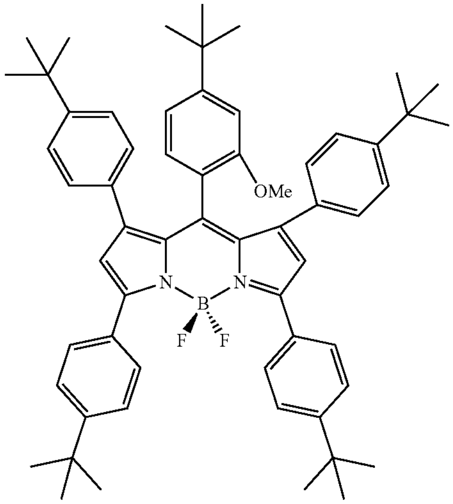

3-2

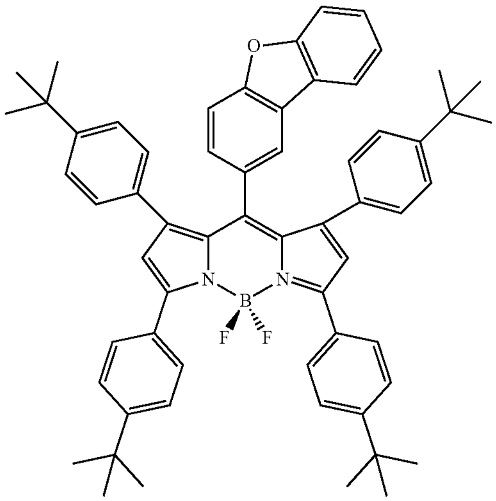

-continued 3-3

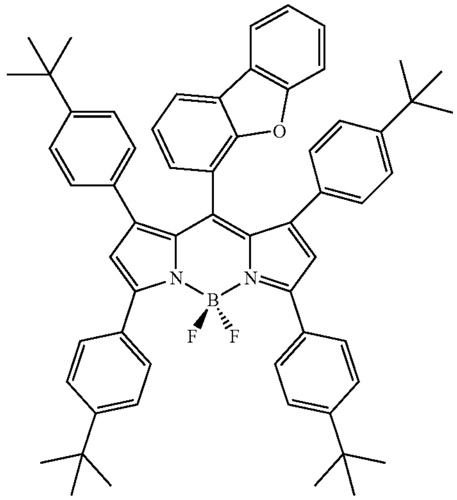

3-4

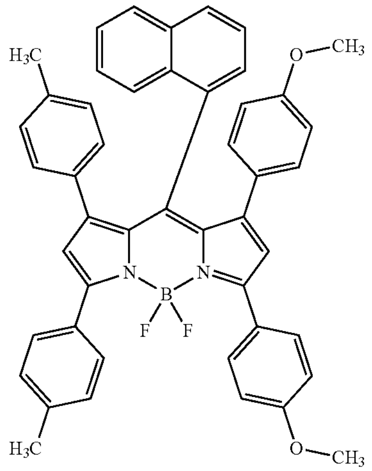

3-5

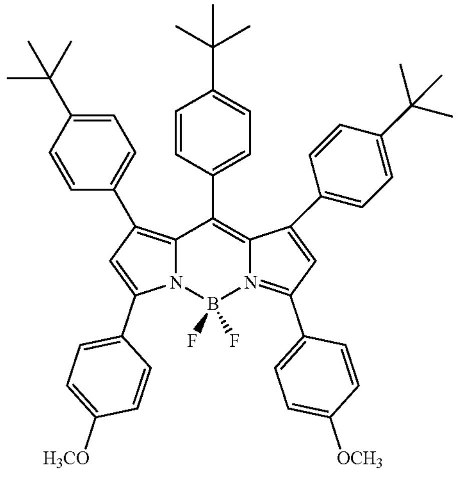

-continued
3-6
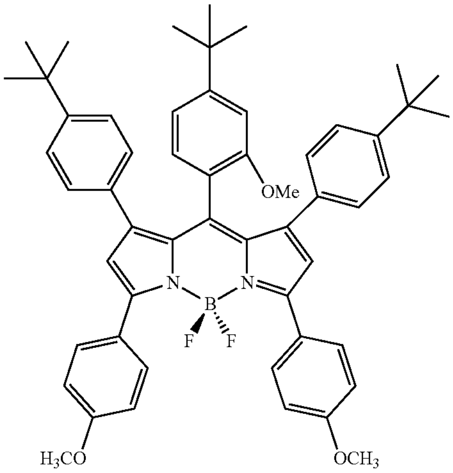
3-7
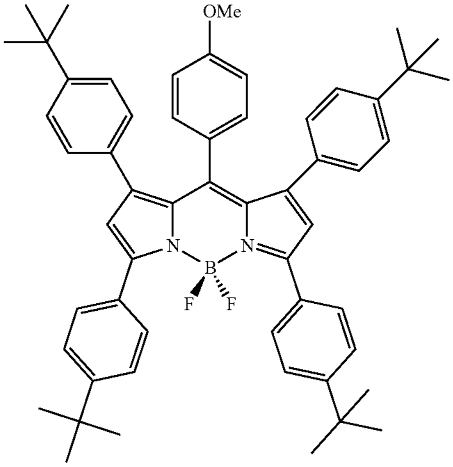
3-8
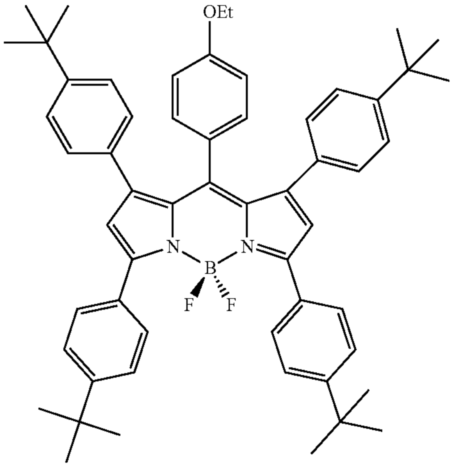
-continued
3-9
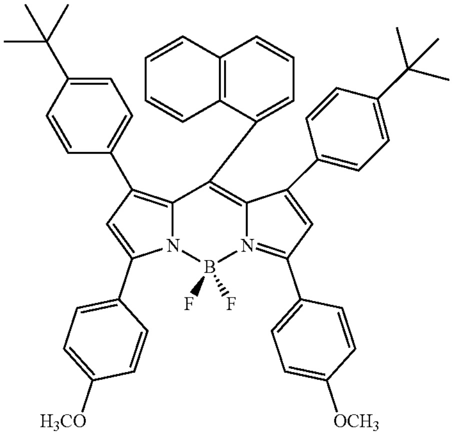
3-10
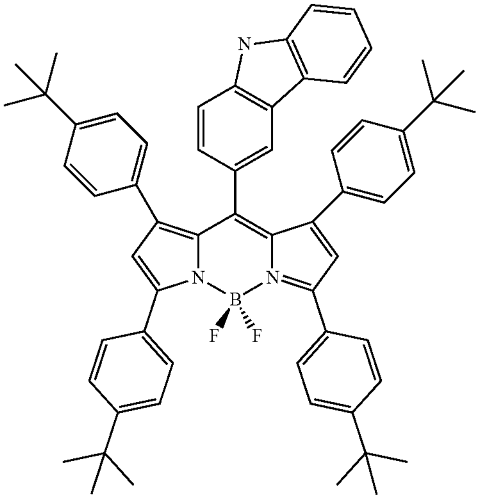
3-11
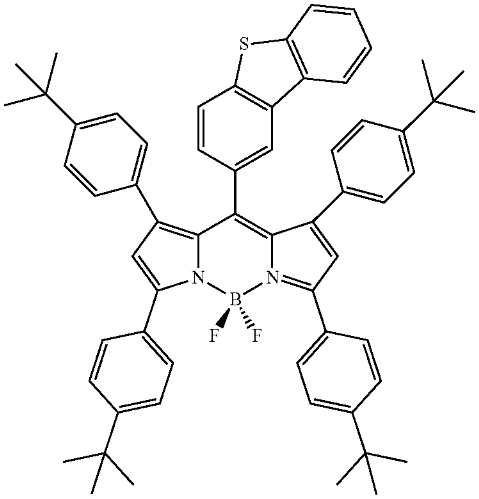

-continued 3-12

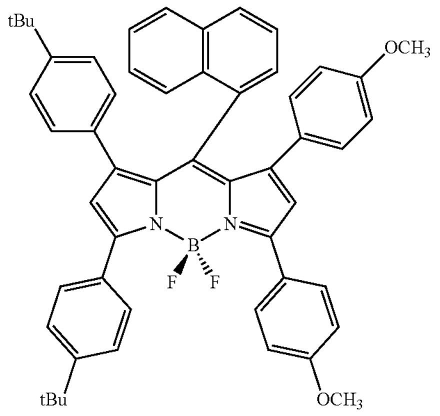

3-13

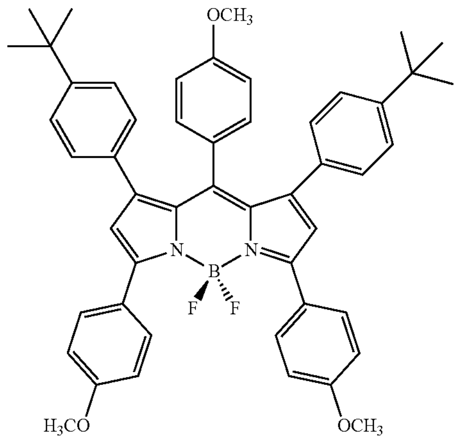

3-14

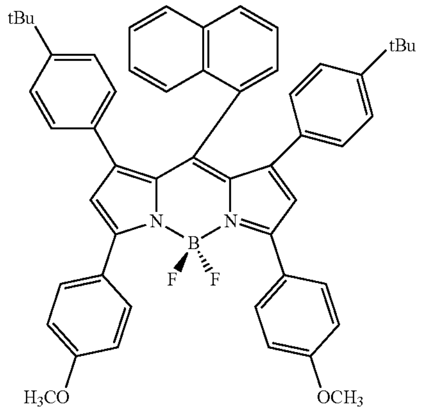

-continued 3-15

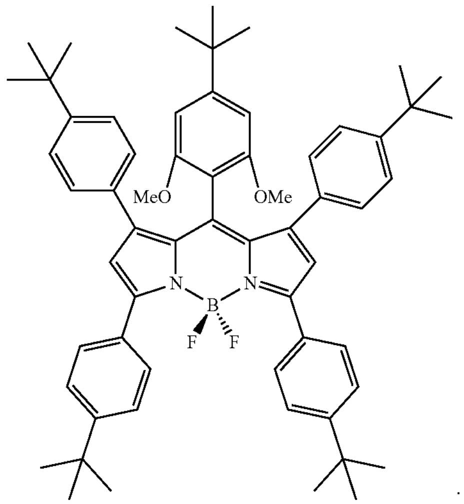

10. The organic light emitting diode of claim 1, wherein the at least one emitting material layer includes a single-layered emitting material layer.

11. The organic light emitting diode of claim 10, the single-layered emitting material layer further includes a fourth compound, and wherein each of an excited singlet energy level and an excited triplet energy level of the fourth compound is higher than each of an excited singlet energy level and an excited triplet energy level of the first compound, respectively.

12. The organic light emitting diode of claim 1, wherein the at least one emitting material layer includes a first emitting material layer disposed between the first and second electrodes and a second emitting material layer disposed between the first electrode and the first emitting material layer or between the first emitting material layer and the second electrode, and wherein the first emitting material layer includes the first compound and the second compound and the second emitting material layer includes the third compound.

13. The organic light emitting diode of claim 12, wherein the first emitting material layer further includes a fourth compound and the second emitting material layer further includes a fifth compound, wherein each of an excited singlet energy level and an excited triplet energy level of the fourth compound is higher than each of an excited singlet energy level and an excited triplet energy level of the first compound, respectively, and wherein an excited singlet energy level of the fifth compound is higher than an excited singlet energy level of the third compound.

14. The organic light emitting diode of claim 12, wherein the at least one emitting material layer further includes a third emitting material layer disposed oppositely to the second emitting material layer with respect to the first emitting material layer.

15. The organic light emitting diode of claim 14, wherein the third emitting material layer includes a sixth compound and a seventh compound, and wherein the sixth compound includes the organic compound having the structure of Formula 5.

16. The organic light emitting diode of claim 15, wherein an excited singlet energy level of the seventh compound is higher than an excited singlet energy level of the sixth compound.

17. The organic light emitting diode of claim 1, wherein the emissive layer includes a first emitting part disposed between the first and second electrodes, a second emitting part disposed between the first emitting part and the second electrode and a charge generation layer disposed between the first and second emitting parts, and wherein at least one of the first emitting part and the second emitting part includes the at least one emitting material layer.

18. The organic light emitting diode of claim 17, wherein the first emitting part emits blue light and the second emitting part includes the at least one emitting material layer.

19. The organic light emitting diode of claim 17, the emissive layer further includes a third emitting part disposed between the second emitting part and the second electrode and a second charge generation layer disposed between the second and third emitting parts.

20. The organic light emitting diode of claim 19, wherein each of the first emitting part and the third emitting part emits blue light, and the second emitting part includes the at least one emitting material layer.

21. An organic light emitting device, including:

a substrate; and the organic light emitting diode according to claim 1 and disposed over the substrate.

* * * * *